US009624234B2

(12) United States Patent
McCarthy et al.

(10) Patent No.: US 9,624,234 B2
(45) Date of Patent: Apr. 18, 2017

(54) HETEROCYCLIC COMPOUNDS AND METHODS FOR THEIR USE

(71) Applicant: Novartis AG, Basel (CH)

(72) Inventors: Thomas David McCarthy, Old Greenwich, CT (US); Alan Naylor, Royston (GB)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/373,357

(22) PCT Filed: Jan. 25, 2013

(86) PCT No.: PCT/AU2013/000062
§ 371 (c)(1),
(2) Date: Jul. 19, 2014

(87) PCT Pub. No.: WO2013/110135
PCT Pub. Date: Aug. 1, 2013

(65) Prior Publication Data
US 2015/0218180 A1 Aug. 6, 2015

(30) Foreign Application Priority Data
Jan. 25, 2012 (AU) .............................. 2012900285

(51) Int. Cl.
C07D 491/056 (2006.01)
C07D 471/04 (2006.01)
C07D 491/048 (2006.01)
C07D 495/04 (2006.01)
C07D 211/60 (2006.01)
C07D 401/04 (2006.01)

(52) U.S. Cl.
CPC ........ *C07D 491/056* (2013.01); *C07D 211/60* (2013.01); *C07D 401/04* (2013.01); *C07D 471/04* (2013.01); *C07D 491/048* (2013.01); *C07D 495/04* (2013.01)

(58) Field of Classification Search
None
See application file for complete search history.

(56) References Cited

U.S. PATENT DOCUMENTS

| 4,404,206 | A | 9/1983 | Vincent et al. |
| 4,624,962 | A | 11/1986 | Henning et al. |
| 5,236,934 | A | 8/1993 | VanAtten |
| 5,612,360 | A | 3/1997 | Boyd et al. |
| 6,743,373 | B1 | 6/2004 | Delplanche et al. |
| 2009/0281310 | A1 | 11/2009 | Kimura et al. |

FOREIGN PATENT DOCUMENTS

| DE | 3302126 A1 | 7/1984 |
| JP | S5692270 A | 7/1981 |
| JP | S5855451 A | 4/1983 |
| JP | S6216466 A | 1/1987 |
| JP | H80892207 A | 4/1996 |
| JP | 2000327594 A | 11/2000 |
| JP | 2008101015 A | 5/2008 |
| WO | WO95/22525 A1 | 8/1995 |
| WO | WO2006/055951 A2 | 5/2006 |
| WO | WO2011/088504 A1 | 7/2011 |

OTHER PUBLICATIONS

Chakrabarty, Endocrinology, 2008, 149(7); 3452-3460.
Clere, Int'l J. Cancer, 2010, 127: 2279-2291.
Izu, J. Biol. Chem., 2009, 248(4): 4857-4864.
Steckelings, Peptides, 2005, 26: 1401-1409.
Wallinder, Biorg & Med. Chem., 2008, 16: 6841-6849.
Wan, J. Med. Chem., 2004, 47: 5995-6008.
Wexler, J. Med. Chem., 1996, 39(3): 625-656.
Mills, Biorg. Med. Chem. Lett., 1995, 5(6):599-604.
Clark-Lewis, et al., J. Chem. Soc., 1961, 189-201.
International Search Report for related application PCT/AU2013/000062, filed on Jan. 25, 2013 and mailed on Feb. 15, 2013.
CAS Reg. No. 1292911-09-1.
CAS Reg. No. 1286930-77-5.
CAS Reg. No. 1286885-25-3.
CAS Reg. No. 1286779-87-0.
CAS Reg. No. 1286642-08-7.
CAS Reg. No. 1286606-92-5.
CAS Reg. No. 1286557-29-6.
CAS Reg. No. 1286466-26-9.
CAS Reg. No. 1286454-96-3.
CAS Reg. No. 1286077-86-8.
CAS Reg. No. 1286065-36-8.
CAS Reg. No. 1276521-37-9.
Database Registry Chemical Abstracts Service, Columbus, Ohio, Accession No. RN 178866-91-6, Entered STN: Jul. 25, 1996.
Ito et al., "A medium-term rat liver bioassay for rapid in vivo detection of carcinogenic potential of chemicals," Cancer Sci. Jan. 2003;94(1):3-8.
Stanton et al., "Angiotensin converting enzyme inhibitors: N-substituted monocyclic and bicyclic amino acid derivatives," J Med Chem. Sep. 1983;26(9):1267-77.
Veeraraghavan et al., "Reissert Compound Studies. XLII. Synthesis and Reactions of the 3,4-Dihydro-beta-carboline Reissert Compound and Observations on alpha, beta, and gamma-Carbolines," J. Heterocyclic Chem., Aug. 1981, 18:909-15.

*Primary Examiner* — Heidi Reese
(74) *Attorney, Agent, or Firm* — Sophie Binet Cross

(57) ABSTRACT

The present invention relates to heterocyclic compounds useful for antagonizing angiotensin II Type 2 ($AT_2$) receptor. More particularly the invention relates to piperidine compounds, compositions containing them and their use in methods of treating or preventing disorders or diseases associated with $AT_2$ receptor function including neuropathic pain, inflammatory pain, conditions associated with neuronal hypersensitivity, impaired nerve conduction velocity, cell proliferation disorders, disorders associated with an imbalance between bone resorption and bone formation and disorders associated with aberrant nerve regeneration.

6 Claims, No Drawings

HETEROCYCLIC COMPOUNDS AND METHODS FOR THEIR USE

PRIORITY DATA AND INCORPORATION BY REFERENCE

This is a National Stage Application under 35 U.S.C §371 of International Application No. PCT/AU2013/000062, filed Jan. 25, 2013, which claims the benefit of priority to Australian Application No. 2012900285, filed on Jan. 25, 2012, the entireties of which are hereby incorporated by reference.

FIELDS OF THE INVENTION

The present invention relates generally to compounds that are useful in antagonizing the angiotensin II type 2 ($AT_2$) receptor. More particularly, the invention relates to heterocyclic compounds of formula (I) and their use as $AT_2$ receptor antagonists. Pharmaceutical compositions comprising the compounds and their use in modulating the $AT_2$ receptor and therapies that require modulation of the $AT_2$ receptor are described.

BACKGROUND OF THE INVENTION

Although the $AT_2$ receptor has been known since the 1980s, much less is known about its biological function than the angiotensin II type 1 ($AT_1$) receptor, which has been studied for its functional effects on vasoconstriction, aldosterone release and cardiovascular growth [Wexler et al., 1996]. However, more recently the $AT_2$ receptor has been implicated in the differentiation and regeneration of neuronal tissue [Steckelings et al., 2005; Chakrabarty et al., 2008], cell proliferation and angiogenesis [Clere et al., 2010] and maintenance of bone mass [Izu et al., 2009].

$AT_2$ receptor antagonists have also recently been associated with the treatment of pain, particularly inflammatory pain [WO 2007/106938] and neuropathic pain [WO 2006/066361], two types of pain which are difficult to treat or relieve. Impaired nerve conduction velocity is also associated with nerve damage and has been implicated in peripheral neuropathies, Carpel Tunnel Syndrome, ulnar neuropathy, Guillian-Barré Syndrome, fascioscapulohumeral muscular dystrophy and spinal disc herneation. Impaired nerve conduction velocity can result in diminished reflex responses and altered peripheral sensation such as parathesia and in some cases pain and $AT_2$ receptor antagonists have been shown to restore nerve conduction velocity [WO 2011/088504].

While there are effective therapies for treating nociceptive pain, inflammatory and neuropathic pain are often resistant to these therapies. In addition, current therapies of neuropathic pain, inflammatory pain, impaired nerve conduction velocity and other types of pain that are difficult to treat, have serious side effects, for example, cognitive changes, sedation, nausea and in the case of narcotic drugs, tolerance and dependence. There is a need for further therapies that treat or prevent neuropathic pain, inflammatory pain, impaired nerve conduction velocity and other painful conditions that are currently difficult to treat.

Cell proliferation and angiogenesis are important biological functions in normal tissue. However, uncontrolled cell proliferation and angiogenesis can lead to tumors and other proliferative disorders. While there are some effective chemotherapies available for tumors, many result in unpleasant side effects and/or have high toxicity for normal cells.

Further therapies for reducing or preventing abnormal cell proliferation in a controlled manner are required and $AT_2$ receptor antagonists have been shown to have antiproliferative activity [Clere et al., 2010].

Osteoporosis is a significant problem in older populations, especially in post-menopausal women. Current therapies for osteoporosis rely on calcium supplementation. However, the control of bone formation and bone resorption is complex and further therapies for improving bone mass are required and $AT_2$ receptor antagonists have been shown to increase bone mass [Izu et al., 2009].

The role of the $AT_2$ receptor in modulating neuronal outgrowth and associated effects of $AT_2$ receptor antagonists on reducing neuronal outgrowth, indicates that $AT_2$ receptor antagonists may be useful therapeutics in diseases characterized by aberrant nerve regeneration [Chakrabarty et al., 2008].

The present invention is predicated in part on the discovery of heterocyclic azetidine and pyrrolidine compounds that have $AT_2$ receptor antagonist activity.

SUMMARY OF THE INVENTION

In a first aspect of the present invention there is provided a compound of formula (I):

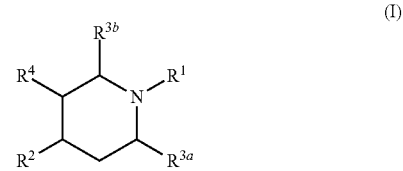

wherein $R^1$ is $—C(=O)CHR^6R^7$, $—C(=O)NR^6R^7$, $—C(=O)CH_2CHR^6R^7$, $—C(=O)CH=CR^6R^7$, $—C(=S)CHR^6R^7$, $—C(=S)NR^6R^7$, $—C(=S)CH_2CHR^6R^7$, $—C(=S)CH=CR^6R^7$, $—C(=NR^8)CHR^6R^7$, $—C(=NR^8)NR^6R^7$, $—C(=NR^8)CH_2CHR^6R^7$ and $—C(=NR^8)CH=CR^6R^7$;

$R^2$ is $—C_{1-6}$alkyl, $—C_{2-6}$alkenyl, $—C_{2-6}$alkynyl, $—OR^8$, $—SR^8$, $—N(R^8)_2$, $—C(=O)R^8$, $—C(=O)N(R^8)_2$, $—N(R^8)C(=O)R^8$, $—N(R^8)C(=O)N(R^8)_2$, $—N(R^8)SO_2R^8$, $—SO_2N(R^8)_2$, $—N(R^8)SO_2N(R^8)_2$, —W-cycloalkyl, —W-cycloalkenyl, —W-aryl, —W-heterocyclyl, —W-heteroaryl, —W—Z—W-cycloalkyl, —W—Z—W-cycloalkenyl, —W—Z—W-aryl, —W—Z—W-heterocyclyl or —W—Z—W-heteroaryl, $=CH—C(=O)$-J-$R^{10}$, $=CHC(=O)NH$-J-$R^{10}$, $—OCH_2CHR^{10}CH_2R^{10}$ or $—OCH_2C(R^{10})=CHR^{10}$;

one of $R^{3a}$ and $R^{3b}$ is hydrogen and the other is a carboxylic acid, $—CH_2CO_2H$, $—C(=O)NH_2$, $—CH_2C(=O)NH_2$, $—CN$, $—CH_2CN$, $—C(=O)C(=O)OH$, $—CH_2OH$, a carboxylic acid bioisostere or a $—CH_2$-carboxylic acid bioisostere;

$R^4$ is hydrogen, $—C_{1-6}$alkyl, $—C_{2-6}$alkenyl, $—C_{2-6}$alkynyl, $—OR^8$, $—SR^8$, $—N(R^8)_2$, $—C(=O)R^8$, $—C(=O)N(R^8)_2$, $—N(R^8)C(=O)R^8$, $—N(R^8)C(=O)N(R^8)_2$, $—N(R^8)SO_2R^8$, $—SO_2N(R^8)_2$, $—N(R^8)SO_2N(R^8)_2$, —W-cycloalkyl, —W-cycloalkenyl, —W-aryl, —W-heterocyclyl, —W-heteroaryl, —W—Z—W-cycloalkyl, —W—Z—W-cycloalkenyl, —W—Z—W-aryl, —W—Z—W-heterocyclyl or —W—Z—W-heteroaryl, $=CH—C(=O)$-J-$R^{10}$, $=CHC(=O)NH$-J-$R^{10}$, $—OCH_2CHR^{10}CH_2R^{10}$ or $—OCH_2C(R^{10})=CHR^{10}$ or $R^4$ and $R^2$ taken together form a fused heterocyclyl or heteroaryl ring system selected from indolyl, pyridinyl, pyrimidinyl, piperidinyl, pyrazolyl, pyridazinyl, indazolyl, coumaranyl, furanyl, benzofuranyl, benzodioxanyl, benzodioxanbenzene, tetrahydrofuranyl, benzotetrahydrofuranyl, thiophenyl, tetrahydrothiophenyl, pyrrolidinyl, pyrrolinyl, pyrrolyl, 1,3-dioxolanyl, pyrazolinyl, thiazolyl, pyranyl, dioxanyl, piperazinyl, pyrazinyl, 1,3-oxazinyl, 1,4-oxazinyl, morpholinyl, thiomorpholinyl, isobenzofuranyl, benzothiophenyl, indolinyl, benzimidazolyl, benzisoxazolyl, benzoxazolyl, benzothiazolyl, benzopyranyl, quinolinyl, isoquinolinyl, quinoxalinyl, naphthyridinyl, carbazolyl, xanthenyl, acridinyl, phenazinyl, phenothiazinyl, phenoxazinyl, azepinyl, oxepinyl and thiepinyl optionally substituted with one or more $R^5$;

$R^5$ is selected from —$C_{1-6}$alkyl, —$C_{2-6}$alkenyl, —$C_{2-6}$alkynyl, cycloalkyl, cycloalkenyl, aryl, heterocyclyl, heteroaryl, —$C_{1-6}$alkyleneR$^{10}$, —$C_{2-6}$alkenyleneR$^{10}$, —$C_{2-6}$alkynyleneR$^{10}$, —$OCF_3$, —$OCHF_2$, —$OR^9$, $NHR^9$, —$OC_{1-6}$alkyleneR$^{10}$, —$OC_{2-6}$alkenyleneR$^{10}$, —$OC_{2-6}$alkynyleneR$^{10}$, —$SO_2NHR^9$, —$NHSO_2R^9$, —NHC(=O)NHR$^9$, —NHC(=O)OR$^9$, —CH(OH)CH(OH)R$^9$, halogen, —$CF_3$, —$CHF_2$, —$CH_2F$ or —CN;

$R^6$ and $R^7$ are independently hydrogen, —$C_{1-6}$alkyl, cycloalkyl, cycloalkenyl, aryl, heterocyclyl, heteroaryl, —$CH_2$aryl, —$CH_2$cycloalkyl, —$CH_2$cycloalkenyl, —$CH_2$heterocyclyl or —$CH_2$heteroaryl; provided that $R^6$ and $R^7$ are not both hydrogen;

$R^8$ is hydrogen, —$C_{1-8}$alkyl, —$C_{2-8}$alkenyl, —$C_{2-8}$alkynyl, aryl, —$C_{1-8}$alkylenearyl, —$C_{2-8}$alkenylenearyl, —$C_{2-8}$alkynylenearyl, —$C_{1-8}$alkylenecycloalkyl, —$C_{1-8}$alkylenecycloalkenyl, —$C_{1-8}$alkyleneheterocyclyl, —$C_{1-8}$alkyleneheteroaryl, —$C_{1-8}$alkyleneCF$_3$, —$C_{2-8}$alkenylenecycloalkyl, —$C_{2-8}$alkenylenecycloalkenyl, —$C_{2-8}$alkenyleneheterocyclyl, —$C_{2-8}$alkenyleneheterocyclyl, —$C_{2-8}$alkenyleneCF$_3$, —$C_{2-8}$alkynylenecycloalkyl, —$C_{2-8}$alkynylenecycloalkenyl, —$C_{2-8}$alkynyleneheterocyclyl, —$C_{2-8}$alkynyleneheteroaryl and $C_{2-8}$alkynyleneCF$_3$;

$R^9$ is —$C_{1-6}$alkyl, —$C_{2-6}$alkenyl, —$C_{2-6}$alkynyl, cycloalkyl, cycloalkenyl, aryl, heterocyclyl, heteroaryl, arylcycloalkyl-, arylcycloalkenyl-, arylaryl-, arylheterocyclyl- or arylheteroaryl-;

W is a covalent bond, —O—, —S—, —SO—, —$SO_2$—, —N(R$^8$)—, —C(=O)—, —N(R$^8$)C(=O)—, —C(=O)N(R$^8$)—, —$C_{1-4}$alkylene-, —$C_{2-4}$alkenylene-, —$C_{2-4}$alkynylene-, —$C_{1-4}$alkyleneQC$_{1-3}$ alkylene-, -QC$_{1-4}$alkylene-, -QC$_{2-4}$alkenylene-, -QC$_{2-4}$alkynylene-, —$C_{1-4}$alkyleneQ-, —$C_{2-4}$alkenyleneQ-, —$C_{2-4}$alkynyleneQ- -QC$_{1-4}$alkyleneQ-, -QC$_{2-4}$alkenyleneQ- or —OC$_{2-4}$alkynyleneQ-;

Q is —O—, —S—, —SO—, —$SO_2$— —N(R$^8$)—, —C(=O)—, —N(R$^8$)C(=O)—, —C(=O)N(R$^8$)—,

Z is -cycloalkyl-, -cycloalkenyl-, -aryl-, -heterocyclyl- or -heteroaryl-;

J is a covalent bond or —$C_{1-6}$alkylene-, —$C_{2-6}$alkenylene- or —$C_{2-6}$alkynylene, in which one —$CH_2$— group in the alkylene, alkenylene or alkynylene group may be replaced by —O—, —S—, —S(O)—, —S(O)$_2$— —N(R$^8$)—, —C(=O)—, —C(=O)NH— or —NHC(=O)—;

$R^{10}$ is cycloalkyl, cycloalkenyl, aryl, heterocyclyl or heteroaryl; and wherein each cycloalkyl, cycloalkenyl, aryl, heterocyclyl and heteroaryl may be optionally substituted;

or a pharmaceutically acceptable salt thereof.

In another aspect, the present invention provides a pharmaceutical composition comprising the compounds of formula (I) or a pharmaceutically acceptable salt thereof and a pharmaceutically acceptable carrier.

In a further aspect of the invention, there is provided a method of treating or preventing neuropathic pain in a subject comprising administering a compound of formula (I) or a pharmaceutically acceptable salt thereof.

In yet a further aspect of the invention there is provided a method of treating or preventing a condition characterized by neuronal hypersensitivity in a subject comprising administering a compound of formula (I) or a pharmaceutically acceptable salt thereof.

In yet another aspect of the invention, there is provided a method of treating or preventing inflammatory pain in a subject comprising administering a compound of formula (I) or a pharmaceutically acceptable salt thereof.

In a further aspect, the present invention provides a method of treating or preventing impaired nerve conduction velocity in a subject comprising administering a compound of formula (I) or a pharmaceutically acceptable salt thereof.

In yet a further aspect of the invention there is provided a method of producing analgesia in a subject comprising administering a compound of formula (I) or a pharmaceutically acceptable salt thereof.

In still another aspect of the invention there is provided a method of treating or preventing a cell proliferative disorder in a subject comprising administering a compound of formula (I) or a pharmaceutically acceptable salt thereof.

In a further aspect the present invention provides a method of treating or preventing a disorder associated with an imbalance between bone resorption and bone formation in a subject comprising administering a compound of formula (I) or a pharmaceutically acceptable salt thereof.

In yet another aspect the present invention provides a method of treating a disorder associated with aberrant nerve regeneration in a subject comprising administering a compound of formula (I) or a pharmaceutically acceptable salt thereof.

DESCRIPTION OF THE INVENTION

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size, or amount that varies by as much as 30%, 25%, 20%, 15% or 10% to a reference quantity, level, value, dimension, size, or amount.

As used herein, the term "$AT_2$ receptor" means an angiotensin II type 2 ($AT_2$) receptor polypeptide that can bind angiotensin II and/or one or more other ligands. The term "$AT_2$ receptor" encompasses vertebrate homologs of $AT_2$ receptor family members, including, but not limited to, mammalian, reptilian and avian homologs. Representative mammalian homologs of $AT_2$ receptor family members include, but are not limited to, murine and human homologs.

The term "antagonist" as used herein refers to a compound that decreases or inhibits the biological activity and/or function of an $AT_2$ receptor, including binding to the $AT_2$ receptor and blocking access to angiotensin II, inhibiting a gene that expresses $AT_2$ receptor, or inhibiting an expression product of that gene. By the term "selective", is meant that the compound binds to and/or inhibits $AT_2$ receptor activity to a greater extent than binding and inhibition of the $AT_1$ receptor. In some instances, selective refers to binding and/or inhibition of the $AT_2$ receptor with little or no binding at the $AT_1$ receptor.

The term "allodynia" as used herein refers to the pain that results from a non-noxious stimulus i.e. pain due to a stimulus that does not normally provoke pain. Examples of allodynia include, but are not limited to, cold allodynia, tactile allodynia (pain due to light pressure or touch), and the like.

The term "analgesia" is used herein to describe states of reduced pain perception, including absence from pain sensations as well as states of reduced or absent sensitivity to noxious stimuli. Such states of reduced or absent pain perception are induced by the administration of a pain-controlling agent or agents and occur without loss of consciousness, as is commonly understood in the art. The term analgesia encompasses the term "antinociception", which is used in the art as a quantitative measure of analgesia or reduced pain sensitivity in animal models.

The term "anti-allodynia" is used herein to describe states of reduced pain perception, including absence from pain sensations as well as states of reduced or absent sensitivity to non-noxious stimuli. Such states of reduced or absent pain perception are induced by the administration of a pain-controlling agent or agents and occur without loss of consciousness, as is commonly understood in the art.

The term "causalgia" as used herein refers to the burning pain, allodynia, and hyperpathia after a traumatic nerve lesion, often combined with vasomotor and sudomotor dysfunction and later trophic changes.

By "complex regional pain syndromes" is meant the pain that includes, but is not limited to, reflex sympathetic dystrophy, causalgia, sympathetically maintained pain, and the like.

By "condition characterized by neuronal hypersensitivity" is meant conditions that have symptoms of pain related to neuronal hypersensitivity and/or allodynia. Examples of this type of condition include fibromyalgia and irritable bowel syndrome.

By "disorder associated with aberrant nerve regeneration" is meant disorders in which there is abnormal axon outgrowth in neurons. This abnormal outgrowth may be associated with painful conditions including breast pain, interstitial cystitis, vulvodynia and cancer chemotherapy-induced neuropathies.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "hyperalgesia" is meant an increased response to a stimulus that is normally painful. A hyperalgesia condition is one that is associated with pain caused by a stimulus that is not normally painful.

By "neuropathic pain" is meant any pain syndrome initiated or caused by a primary lesion or dysfunction in the peripheral or central nervous system. Examples of neuropathic pain include, but are not limited to, thermal or mechanical hyperalgesia, thermal or mechanical allodynia, diabetic pain, entrapment pain, and the like.

The term "nociceptive pain" refers to the normal, acute pain sensation evoked by activation of nociceptors located in non-damaged skin, viscera and other organs in the absence of sensitization.

As used herein "inflammatory pain" refers to pain induced by inflammation. Such types of pain may be acute or chronic and can be due to any number of conditions characterized by inflammation including, without limitation, burns including chemical, frictional or thermal burns, autoimmune diseases such as rheumatoid arthritis, osteoarthritis and inflammatory bowel disease including Crohn's disease and colitis, as well as other inflammatory diseases including carditis, dermatitis, myositis, neuritis and collagen vascular diseases.

The term "pain" as used herein is given its broadest sense and includes an unpleasant sensory and emotional experience associated with actual or potential tissue damage, or described in terms of such damage and includes the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (Dorland's Illustrated Medical Dictionary, $28^{th}$ Edition, W. B. Saunders Company, Philadelphia, Pa.). The goal of treatment of pain is to reduce the degree of severity of pain perceived by a treatment subject.

By the phrases "impaired NCV" or "impaired nerve conduction velocity" and the like is meant any nerve conduction demonstrably abnormal in any one of the parameters assessed for normal nerve signal conduction. Whether the various parameters of NCV are normal is typically an assessment made by the relevant trained clinician. General background, terminology and procedures known to those in the art for evaluating NCV are described in "Proper performance and interpretation of electrodiagnostic studies' Muscle Nerve. (2006) 33(3):436-439 and "Electrodiagnostic medicine listing of sensory, motor, and mixed nerves." Appendix J of Current Procedural Terminology (CPT) 2007, authored by The American Association of Neuromuscular & Electrodiagnostic Medicine and published by the American Medical Association. Impaired or abnormal nerve conduction velocity is a symptom of nerve dysfunction or damage and may be causal to or a symptom of a large number of diseases or disorders, particularly diseases or disorders that exhibit diminished reflex responses and altered peripheral sensation including paresthesia. As used herein, "paresthesia" refers to a sensation of tingling, prickling, weakness or numbness in a subject's skin. It is also known as "pins and needles" or a limb "falling asleep". Paresthesia may be transient, acute or chronic and may occur alone or be accompanied by other symptoms such as pain.

As used herein, the term "cell proliferative disorder" refers to diseases or conditions where unwanted or damaged cells are not removed by normal cellular process, or diseases or conditions in which cells undergo aberrant, unwanted or inappropriate proliferation. Disorders characterized by inappropriate cell proliferation include, for example, inflammatory conditions such as inflammation arising from acute tissue injury including, for example, acute lung injury, cancer including cancers characterized by tumors, autoimmune disorders, tissue hypertrophy and the like.

The term "disorder associated with an imbalance between bone resorption and bone formation" includes disorders where there is insufficient development of bone mass, excessive bone resorption and insufficient bone formation during remodelling. An exemplary disorder associated with an imbalance between bone resorption and bone formation is osteoporosis.

As used herein, the term "alkyl" refers to a straight chain or branched saturated hydrocarbon group having 1 to 10 carbon atoms. Where appropriate, the alkyl group may have a specified number of carbon atoms, for example, $C_{1-6}$alkyl which includes alkyl groups having 1, 2, 3, 4, 5 or 6 carbon atoms in a linear or branched arrangement. Examples of suitable alkyl groups include, but are not limited to, methyl, ethyl, n-propyl, i-propyl, n-butyl, i-butyl, t-butyl, n-pentyl, 2-methylbutyl, 3-methylbutyl, 4-methylbutyl, n-hexyl, 2-methylpentyl, 3-methylpentyl, 4-methylpentyl, 5-methylpentyl, 2-ethylbutyl, 3-ethylbutyl, heptyl, octyl, nonyl and decyl.

As used herein, the term "alkenyl" refers to a straight-chain or branched hydrocarbon group having one or more double bonds between carbon atoms and having 2 to 10 carbon atoms. Where appropriate, the alkenyl group may have a specified number of carbon atoms. For example, $C_2$-$C_6$ as in "$C_2$-$C_6$alkenyl" includes groups having 2, 3, 4, 5 or 6 carbon atoms in a linear or branched arrangement. Examples of suitable alkenyl groups include, but are not limited to, ethenyl, propenyl, isopropenyl, butenyl, butadienyl, pentenyl, pentadienyl, hexenyl, hexadienyl, heptenyl, octenyl, nonenyl and decenyl.

As used herein, the term "alkynyl" refers to a straight-chain or branched hydrocarbon group having one or more triple bonds and having 2 to 10 carbon atoms. Where appropriate, the alkynyl group may have a specified number of carbon atoms. For example, $C_2$-$C_6$ as in "$C_2$-$C_6$alkynyl" includes groups having 2, 3, 4, 5 or 6 carbon atoms in a linear or branched arrangement. Examples of suitable alkynyl groups include, but are not limited to ethynyl, propynyl, butynyl, pentynyl and hexynyl.

As used herein, the term "cycloalkyl" refers to a saturated cyclic hydrocarbon. The cycloalkyl ring may include a specified number of carbon atoms. For example, a 3 to 8 membered cycloalkyl group includes 3, 4, 5, 6, 7 or 8 carbon atoms. Examples of suitable cycloalkyl groups include, but are not limited to, cyclopropyl, cyclobutyl, cyclopentyl, cyclohexyl, cycloheptyl and cyclooctyl.

As used herein, the term "cycloalkenyl" refers to an unsaturated cyclic hydrocarbon. The cycloalkenyl ring may include a specified number of carbon atoms. For example, a 5 to 8 membered cycloalkenyl group includes 5, 6, 7 or 8 carbon atoms. The cycloalkenyl group has one or more double bonds and when more than one double bond is present, the double bonds may be unconjugated or conjugated, however the cycloalkenyl group is not aromatic. Examples of suitable cycloalkenyl groups include, but are not limited to, cyclopentenyl, cyclohexenyl, cyclohexadienyl, cycloheptenyl, cycloheptadienyl, cycloheptatrienyl, cyclooctenyl, cyclooctadienyl and cyclooctatrienyl rings.

As used herein, the term "aryl" is intended to mean any stable, monocyclic, bicyclic or tricyclic carbon ring system of up to 7 atoms in each ring, wherein at least one ring is aromatic. Examples of such aryl groups include, but are not limited to, phenyl, naphthyl, tetrahydronaphthyl, indanyl, fluorenyl, phenanthrenyl, biphenyl and binaphthyl.

As used herein, the term "alkylene" refers to a divalent saturated hydrocarbon chain having 1 to 8 carbon atoms. Where appropriate, the alkylene group may have a specified number of carbon atoms, for example, $C_{1-6}$alkylene includes alkylene groups having 1, 2, 3, 4, 5 or 6 carbon atoms in a linear arrangement. Examples of suitable alkylene groups include, but are not limited to, —$CH_2$—, —$CH_2CH_2$—, —$CH_2CH_2CH_2$—, —$CH_2CH_2CH_2CH_2$—, —$CH_2CH_2CH_2CH_2CH_2$— and —$CH_2CH_2CH_2CH_2CH_2CH_2$—.

As used herein, the term "alkenylene" refers to a divalent unsaturated hydrocarbon chain having 2 to 8 carbon atoms and at least one double bond. Where appropriate, the alkenylene group may have a specified number of carbon atoms, for example, $C_{2-6}$alkenylene includes alkenylene groups having 2, 3, 4, 5 or 6 carbon atoms in a linear arrangement. The double bonds may, be in either E or Z configuration. Examples of suitable alkenylene groups include, but are not limited to, —CH═CH—, —CH═CHCH$_2$—, —CH$_2$CH═CH—, —CH═CHCH$_2$CH$_2$—, —CH$_2$CH═CHCH$_2$—, —CH$_2$CH$_2$CH═CH—, —CH═CHCH$_2$CH$_2$CH$_2$—, —CH$_2$CH═CHCH$_2$CH$_2$—, —CH$_2$CH$_2$CH═CHCH$_2$—, —CH$_2$CH$_2$CH$_2$CH═CH—, —CH═CHCH$_2$CH$_2$CH$_2$CH$_2$— —CH$_2$CH═CHCH$_2$CH$_2$CH$_2$—, —CH$_2$CH$_2$CH═CHCH$_2$CH$_2$—, —CH$_2$CH$_2$CH$_2$CH═CHCH$_2$— and —CH$_2$CH$_2$CH$_2$CH$_2$CH═CH—.

As used herein, the term "alkynylene" refers to a divalent unsaturated hydrocarbon chain having 2 to 8 carbon atoms and at least one triple bond. Where appropriate, the alkynylene group may have a specified number of carbon atoms, for example, $C_{2-6}$alkynylene includes alkynylene groups having 2, 3, 4, 5 or 6 carbon atoms in a linear arrangement. Examples of suitable alkynylene groups include, but are not limited to, —C≡C—, —C≡CCH$_2$—, —CH$_2$C≡C—, C≡CCH$_2$CH$_2$—, —CH$_2$C≡CCH$_2$—, —CH$_2$CH$_2$C≡C—, —C≡CCH$_2$CH$_2$CH$_2$—, —CH$_2$C≡CCH$_2$CH$_2$—, —CH$_2$CH$_2$C≡CCH$_2$—, —CH$_2$CH$_2$CH$_2$C≡C—, —C≡CCH$_2$CH$_2$CH$_2$CH$_2$— —CH$_2$C≡CCH$_2$CH$_2$CH$_2$—, —CH$_2$CH$_2$C≡CCH$_2$CH$_2$—, —CH$_2$CH$_2$CH$_2$C≡CCH$_2$— and —CH$_2$CH$_2$CH$_2$CH$_2$C≡C—.

In some embodiments, one or more "—CH$_2$—" groups in an alkylene, alkenylene or alkynylene group may be replaced by a heteroatom or a group containing a heteroatom including —O—, —S—, —NH—, —NR—, —S(O)—, —S(O)$_2$—, —C(═O)—, —C(═O)NH— and —NHC(═O)—.

The term "benzyl" where used herein refers to a phenylmethylene group, $C_6H_5CH_2$—.

As used herein, the term "halogen" or "halo" refers to fluorine (fluoro), chlorine (chloro), bromine (bromo) and iodine (iodo).

The term "heterocyclic" or "heterocyclyl" as used herein, refers to a cyclic hydrocarbon in which one to four carbon atoms have been replaced by heteroatoms independently selected from the group consisting of N, N(R), S, S(O), S(O)$_2$ and O. A heterocyclic ring may be saturated or unsaturated but not aromatic. A heterocyclic group may also be part of a spirocyclic group containing 1, 2 or 3 rings, two of which are in a "spiro" arrangement. Examples of suitable heterocyclyl groups include azetidine, tetrahydrofuranyl, tetrahydrothiophenyl, pyrrolidinyl, 2-oxopyrrolidinyl, pyrrolinyl, pyranyl, dioxolanyl, piperidinyl, 2-oxopiperidinyl, pyrazolinyl, thiazolinyl, dithiolyl, oxathiolyl, dioxanyl, dioxinyl, dioxazolyl, oxathiozolyl, oxazolonyl, piperazinyl, morpholino, thiomorpholinyl, 3-oxomorpholinyl, dithianyl, trithianyl and oxazinyl.

The term "heteroaryl" as used herein, represents a stable monocyclic, bicyclic or tricyclic ring of up to 7 atoms in each ring, wherein at least one ring is aromatic and at least one ring contains from 1 to 4 heteroatoms selected from the group consisting of O, N and S. Heteroaryl groups within the scope of this definition include, but are not limited to, acridinyl, carbazolyl, cinnolinyl, quinoxalinyl, quinazolinyl, pyrazolyl, indolyl, isoindolyl, 1H,3H-1-oxoisoindolyl, benzotriazolyl, furanyl, thienyl, thiophenyl, benzothienyl, benzofuranyl, benzodioxane, benzodioxin, quinolinyl, isoquinolinyl, oxazolyl, isoxazolyl, imidazolyl, pyrazinyl, pyridazinyl, pyridinyl, pyrimidinyl, pyrrolyl, tetrahydroquinolinyl, thiazolyl, isothiazolyl, 1,2,3-triazolyl, 1,2,4-triazolyl, 1,2,4-oxadiazolyl, 1,2,4-thiadiazolyl, 1,3,5-triazinyl, 1,2,4-triazinyl, 1,2,4,5-tetrazinyl, tetrazolyl, carbazolyl, xanthenyl, acridinyl, phenazinyl, phenothiazinyl, phenoxazinyl, azepinyl, oxepinyl and thiepinyl. Particular heteroaryl groups have 5- or 6-membered rings, such as pyrazolyl, furanyl, thienyl, oxazolyl, indolyl, isoindolyl, 1H,3H-1-oxoisoindolyl, isoxazolyl, imidazolyl, pyrazinyl, pyridazinyl, pyridinyl, pyrimidinyl, pyrrolyl, thiazolyl, isothiazolyl, 1,2,3-triazolyl, 1,2,4-triazolyl and 1,2,4-oxadiazolyl and 1,2,4-thiadiazolyl.

Each alkyl, alkenyl, alkynyl, cycloalkyl, cycloalkenyl, aryl, heterocyclyl and heteroaryl whether an individual entity or as part of a larger entity may be optionally substituted with one or more optional substituents selected from the group consisting of $C_{1-6}$alkyl, $C_{2-6}$-alkenyl, $C_{3-6}$cycloalkyl, oxo (=O), —OH, —SH, $C_{1-6}$alkylO—, $C_{2-6}$alkenylO—, $C_{3-6}$cycloalkylO—, $C_{1-6}$alkylS—, $C_{2-6}$alkenylS—, $C_{3-6}$cycloalkylS—, —$CO_2$H, —$CO_2C_{1-6}$alkyl, —$NH_2$, —NH($C_{1-6}$alkyl), —N($C_{1-6}$alkyl)$_2$, —NH(phenyl), —N(phenyl)$_2$, oxo, —CN, —$NO_2$, -halogen, —$CF_3$, —$OCF_3$, —$SCF_3$, —$CHF_2$, —$OCHF_2$, —$SCHF_2$, -phenyl, -heterocyclyl, -heteroaryl, —Oheteroaryl, —Oheterocyclyl, —Ophenyl, —C(O)phenyl, —C(O)$C_{1-6}$alkyl. Examples of suitable substituents include, but are not limited to, methyl, ethyl, propyl, isopropyl, butyl, sec-butyl, tert-butyl, vinyl, methoxy, ethoxy, propoxy, isopropoxy, butoxy, methylthio, ethylthio, propylthio, isopropylthio, butylthio, hydroxy, hydroxymethyl, hydroxyethyl, hydroxypropyl, hydroxybutyl, fluoro, chloro, bromo, iodo, cyano, nitro, —$CO_2$H, —$CO_2CH_3$, trifluoromethyl, trifluoromethoxy, trifluoromethylthio, difluoromethyl, difluoromethoxy, difluoromethylthio, morpholino, amino, methylamino, dimethylamino, phenyl, phenoxy, phenylcarbonyl, benzyl and acetyl.

The term "carboxylic acid bioisotere" refers to a group which is physiochemically or topologically similar to carboxylic acid or carboxylate group. Examples of suitable carboxylic acid or carboxylate isosteres include, but are not limited to, tetrazole, tetrazolate, —CONH-tetrazole, oxadiazole, phosphate (—$PO_3H_2$), —C(OH)($CF_3$)$_2$, N-(aryl or heteroaryl)-sulfonamides, acylsulfonamides and sulfonic acid (—$SO_3$H) [See Patani and LaVoie, 1996]. Examples of sulfonamide isosteric equivalents of carboxy groups include —C(=O)NHSO$_2$R$^a$, —C(=O)NHSO$_2$NH(R$^a$), —C(=O)NHSO$_2$N(R$^a$)$_2$, —SO$_2$NHC(=O)R$^a$, —SO$_2$NHC(=O)NHR$^a$, —SO$_2$NHR$^a$ and —NHSO$_2$R$^a$, where R$^a$ is selected from the group consisting of $C_{1-6}$alkyl, $C_{2-6}$alkenyl, $C_{3-8}$cycloalkyl, aryl, heterocyclyl, heteroaryl and —$CF_3$.

The compounds of the invention may be in the form of pharmaceutically acceptable salts. It will be appreciated however that non-pharmaceutically acceptable salts also fall within the scope of the invention since these may be useful as intermediates in the preparation of pharmaceutically acceptable salts or may be useful during storage or transport. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, toluenesulphonic, benezenesulphonic, salicylic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

Basic nitrogen-containing groups may be quaternized with such agents as lower alkyl halide, such as methyl, ethyl, propyl, and butyl chlorides, bromides and iodides; dialkyl sulfates like dimethyl and diethyl sulfate; and others.

It will also be recognised that compounds of the invention may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution. The compounds of the invention may exist as geometric isomers. The invention also relates to compounds in substantially pure cis (Z) or trans (E) or mixtures thereof.

Compounds of the Invention

In a first aspect of the present invention there is provided a compound of formula (I):

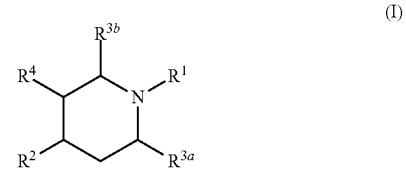

(I)

wherein $R^1$ is —C(=O)CHR$^6$R$^7$, —C(=O)NR$^6$R$^7$, —C(=O)CH$_2$CHR$^6$R$^7$, —C(=O)CH=CR$^6$R$^7$, —C(=S)CHR$^6$R$^7$, —C(=S)NR$^6$R$^7$, —C(=S)CH$_2$CHR$^6$R$^7$, —C(=S)CH=CR$^6$R$^7$, —C(=NR$^8$)CHR$^6$R$^7$, —C(=NR$^8$)NR$^6$R$^7$, —C(=NR$^8$)CH$_2$CHR$^6$R$^7$ and —C(=NR$^8$)CH=CR$^6$R$^7$;

$R^2$ is —$C_{1-6}$alkyl, —$C_{2-6}$alkenyl, —$C_{2-6}$alkynyl, —OR$^8$, —SR$^8$, —N(R$^8$)$_2$, —C(=O)R$^8$, —C(=O)N(R$^8$)$_2$, —N(R$^8$)C(=O)R$^8$, —N(R$^8$)C(=O)N(R$^8$)$_2$, —N(R$^8$)SO$_2$R$^8$, —SO$_2$N(R$^8$)$_2$, —N(R$^8$)SO$_2$N(R$^8$)$_2$, —W-cycloalkyl, —W-cycloalkenyl, —W-aryl, —W-heterocyclyl, —W-heteroaryl, —W—Z—W-cycloalkyl, —W—Z—W-cycloalkenyl, —W—Z—W-aryl, —W—Z—W-heterocyclyl or —W—Z—W-heteroaryl, =CH—C(=O)-J-R$^{10}$, =CHC(=O)NH-J-R$^{10}$, —OCH$_2$CHR$^{10}$CH$_2$R$^{10}$ or —OCH$_2$C(R$^{10}$)=CHR$^{10}$;

one of $R^{3a}$ and $R^{3b}$ is hydrogen and the other is a carboxylic acid, —CH$_2$CO$_2$H, —C(=O)NH$_2$, —CH$_2$C(=O)NH$_2$, —CN, —CH$_2$CN, —C(=O)C(=O)OH, —CH$_2$OH, a carboxylic acid bioisostere or a —CH$_2$-carboxylic acid bioisostere;

$R^4$ is hydrogen, —$C_{1-6}$alkyl, —$C_{2-6}$alkenyl, —$C_{2-6}$alkynyl, —OR$^8$, —SR$^8$, —N(R$^8$)$_2$, —C(=O)R$^8$, —C(=O)N(R$^8$)$_2$, —N(R$^8$)C(=O)R$^8$, —N(R$^8$)C(=O)N(R$^8$)$_2$, —N(R$^8$)SO$_2$R$^8$, —SO$_2$N(R$^8$)$_2$, —N(R$^8$)SO$_2$N(R$^8$)$_2$, —W-cycloalkyl, —W-cycloalkenyl, —W-aryl, —W-heterocyclyl, —W-heteroaryl, —W—Z—W-cycloalkyl, —W—Z—W-cycloalkenyl, —W—Z—W-aryl, —W—Z—W-heterocyclyl or —W—Z—W-heteroaryl, =CH—C(=O)-J-R¹⁰, =CHC(=O)NH-J-R¹⁰, —OCH₂CHR¹⁰CH₂R¹⁰ or —OCH₂C(R¹⁰)=CHR¹⁰ or R⁴ and R² taken together form a fused heterocyclyl or heteroaryl ring system selected from indolyl, pyridinyl, pyrimidinyl, piperidinyl, pyrazolyl, pyridazinyl, indazolyl, coumaranyl, furanyl, benzofuranyl, benzodioxanyl, benzodioxanbenzene, tetrahydrofuranyl, benzotetrahydrofuranyl, thiophenyl, tetrahydrothiophenyl, pyrrolidinyl, pyrrolinyl, pyrrolyl, 1,3-dioxolanyl, pyrazolinyl, thiazolyl, pyranyl, dioxanyl, piperazinyl, pyrazinyl, 1,3-oxazinyl, 1,4-oxazinyl, morpholinyl, thiomorpholinyl, isobenzofuranyl, benzothiophenyl, indolinyl, benzimidazolyl, benzisoxazolyl, benzoxazolyl, benzothiazolyl, benzopyranyl, quinolinyl, isoquinolinyl, quinoxalinyl, naphthyridinyl, carbazolyl, xanthenyl, acridinyl, phenazinyl, phenothiazinyl, phenoxazinyl, azepinyl, oxepinyl and thiepinyl optionally substituted with one or more R⁵;

R⁵ is selected from —C₁₋₆alkyl, —C₂₋₆alkenyl, —C₂₋₆alkynyl, cycloalkyl, cycloalkenyl, aryl, heterocyclyl, heteroaryl, —C₁₋₆alkyleneR¹⁰, —C₂₋₆alkenyleneR¹⁰, —C₂₋₆alkynyleneR¹⁰, —OCF₃, —OCHF₂, —OR⁹, NHR⁹, —OC₁₋₆alkyleneR¹⁰, —OC₂₋₆alkenyleneR¹⁰, —OC₂₋₆alkynyleneR¹⁰, —SO₂NHR⁹, —NHSO₂R⁹, —NHC(=O)NHR⁹, —NHC(=O)OR⁹, —CH(OH)CH(OH)R⁹, halogen, —CF₃, —CHF₂, —CH₂F or —CN;

R⁶ and R⁷ are independently hydrogen, —C₁₋₆alkyl, cycloalkyl, cycloalkenyl, aryl, heterocyclyl, heteroaryl, —CH₂aryl, —CH₂cycloalkyl, —CH₂cycloalkenyl, —CH₂heterocyclyl or —CH₂heteroaryl; provided that R⁶ and R⁷ are not both hydrogen;

R⁸ is hydrogen, —C₁₋₈alkyl, —C₂₋₈alkenyl, —C₂₋₈alkynyl, aryl, —C₁₋₈alkylenearyl, —C₂₋₈alkenylenearyl, —C₂₋₈alkynylenearyl, —C₁₋₈alkylenecycloalkyl, —C₁₋₈alkylenecycloalkenyl, —C₁₋₈alkyleneheterocyclyl, —C₁₋₈alkyleneheteroaryl, —C₁₋₈alkyleneCF₃, —C₂₋₈alkenylenecycloalkyl, —C₂₋₈alkenylenecycloalkenyl, —C₂₋₈alkenyleneheterocyclyl, —C₂₋₈alkenyleneheterocyclyl, —C₂₋₈alkenyleneCF₃, —C₂₋₈alkynylenecycloalkyl, —C₂₋₈alkynylenecycloalkenyl, —C₂₋₈alkynyleneheterocyclyl, —C₂₋₈alkynyleneheteroaryl and C₂₋₈alkynyleneCF₃;

R⁹ is —C₁₋₆alkyl, —C₂₋₆alkenyl, —C₂₋₆alkynyl, cycloalkyl, cycloalkenyl, aryl, heterocyclyl, heteroaryl, arylcycloalkyl-, arylcycloalkenyl-, arylaryl-, arylheterocyclyl- or arylheteroaryl-;

W is a covalent bond, —O—, —S—, —SO—, —SO₂— —N(R⁸)—, —C(=O)—, —N(R⁸)C(=O)—, —C(=O)N(R⁸)—, —C₁₋₄alkylene-, —C₂₋₄alkenylene-, —C₂₋₄alkynylene-, —C₁₋₃alkyleneQC₁₋₃alkylene-, -QC₁₋₄alkylene-, -QC₂₋₄alkenylene-, -QC₂₋₄alkynylene-, —C₁₋₄alkyleneQ-, —C₂₋₄alkenyleneQ-, —C₂₋₄alkynyleneQ-, -QC₁₋₄alkyleneQ-, -QC₂₋₄alkenyleneQ- or —OC₂₋₄alkynyleneQ-;

Q is —O—, —S—, —SO—, —SO₂— —N(R⁸)—, —C(=O)—, —N(R⁸)C(=O)—, —C(=O)N(R⁸)—,

Z is -cycloalkyl-, -cycloalkenyl-, -aryl-, -heterocyclyl- or -heteroaryl-;

J is a covalent bond or —C₁₋₆alkylene-, —C₂₋₆alkenylene- or —C₂₋₆alkynylene, in which one —CH₂— group in the alkylene, alkenylene or alkynylene group may be replaced by —O—, —S—, —S(O)—, —S(O)₂— —N(R⁸)—, —C(=O)—, —C(=O)NH— or —NHC(=O)—;

R¹⁰ is cycloalkyl, cycloalkenyl, aryl, heterocyclyl or heteroaryl; and wherein each cycloalkyl, cycloalkenyl, aryl, heterocyclyl and heteroaryl may be optionally substituted;

or a pharmaceutically acceptable salt thereof.

In some embodiments of the present invention, the compound of formula (I) is a compound of formula (IA):

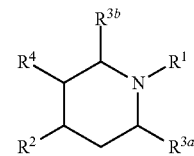

(IA)

wherein R¹ is —C(=O)CHR⁶R⁷, —C(=O)NR⁶R⁷, —C(=O)CH₂CHR⁶R⁷, —C(=O)CH=CR⁶R⁷, —C(=S)CHR⁶R⁷, —C(=S)NR⁶R⁷, —C(=S)CH₂CHR⁶R⁷, —C(=S)CH=CR⁶R⁷, —C(=NR⁸)CHR⁶R⁷, —C(=NR⁸)NR⁶R⁷, —C(=NR⁸)CH₂CHR⁶R⁷ and —C(=NR⁸)CH=CR⁶R⁷;

R² is —C₁₋₆alkyl, —C₂₋₆alkenyl, —C₂₋₆alkynyl, —OR⁸, —SR⁸, —N(R⁸)₂, —C(=O)R⁸, —C(=O)N(R⁸)₂, —N(R⁸)C(=O)R⁸, —N(R⁸)C(=O)N(R⁸)₂, —N(R⁸)SO₂R⁸, —SO₂N(R⁸)₂, —N(R⁸)SO₂N(R⁸)₂, —W-cycloalkyl, —W-cycloalkenyl, —W-aryl, —W-heterocyclyl, —W-heteroaryl, —W—Z—W-cycloalkyl, —W—Z—W-cycloalkenyl, —W—Z—W-aryl, —W—Z—W-heterocyclyl or —W—Z—W-heteroaryl, =CH—C(=O)-J-R¹⁰, =CHC(=O)NH-J-R¹⁰, —OCH₂CHR¹⁰CH₂R¹⁰ or —OCH₂C(R¹⁰)=CHR¹⁰;

one of R³ᵃ and R³ᵇ is hydrogen and the other is a carboxylic acid, —CH₂CO₂H, —C(=O)C(=O)OH or a carboxylic acid bioisostere;

R⁴ is hydrogen, —C₁₋₆alkyl, —C₂₋₆alkenyl, —C₂₋₆alkynyl, —OR⁸, —SR⁸, —N(R⁸)₂, —C(=O)R⁸, —C(=O)N(R⁸)₂, —N(R⁸)C(=O)R⁸, —N(R⁸)C(=O)N(R⁸)₂, —N(R⁸)SO₂R⁸, —SO₂N(R⁸)₂, —N(R⁸)SO₂N(R⁸)₂, —W-cycloalkyl, —W-cycloalkenyl, —W-aryl, —W-heterocyclyl, —W-heteroaryl, —W—Z—W-cycloalkyl, —W—Z—W-cycloalkenyl, —W—Z—W-aryl, —W—Z—W-heterocyclyl or —W—Z—W-heteroaryl, =CH—C(=O)-J-R¹⁰, =CHC(=O)NH-J-R¹⁰, —OCH₂CHR¹⁰CH₂R¹⁰ or —OCH₂C(R¹⁰)=CHR¹⁰ or R⁴ and R² taken together form a fused heterocyclyl or heteroaryl ring system selected from indolyl, pyridinyl, pyrimidinyl, piperidinyl, pyrazolyl, pyridazinyl, indazolyl, coumaranyl, benzofuranyl, benzodioxanyl, benzodioxanbenzene, tetrahydrofuranyl, thiophenyl, tetrahydrothiophenyl, pyrrolidinyl, pyrrolinyl, pyrrolyl, 1,3-dioxolanyl, pyrazolinyl, thiazolyl, pyranyl, dioxanyl, piperazinyl, pyrazinyl, 1,3-oxazinyl, 1,4-oxazinyl, morpholinyl, thiomorpholinyl, isobenzofuranyl, benzothiophenyl, indolinyl, benzimidazolyl, benzisoxazolyl, benzoxazolyl, benzothiazolyl, benzopyranyl, quinolinyl, isoquinolinyl, quinoxalinyl, naphthyridinyl, carbazolyl, xanthenyl, acridinyl, phenazinyl, phenothiazinyl, phenoxazinyl, azepinyl, oxepinyl and thiepinyl optionally substituted with R⁵;

R⁵ is selected from —C₁₋₆alkyl, —C₂₋₆alkenyl, —C₂₋₆alkynyl, cycloalkyl, cycloalkenyl, aryl, heterocyclyl, heteroaryl, —C₁₋₆alkyleneR¹⁰, —C₂₋₆alkenyleneR¹⁰, —C₂₋₆alkynyleneR¹⁰, —OCF₃, —OCHF₂, —OR⁹, —NHR⁹, —OC₁₋₆alkyleneR¹⁰, —OC₂₋₆alkenyleneR¹⁰, —OC₂₋₆alkynyleneR¹⁰, —SO₂NHR⁹, —NHSO₂R⁹, —NHC(=O)NHR⁹, —NHC(=O)OR⁹, —CH(OH)CH(OH)R⁹, halogen, —CF₃, —CHF₂, —CH₂F or —CN;

R⁶ and R⁷ are independently hydrogen, —C₁₋₆alkyl, cycloalkyl, cycloalkenyl, aryl, heterocyclyl, heteroaryl, —CH₂aryl, —CH₂cycloalkyl, —CH₂cycloalkenyl, —CH₂heterocyclyl or —CH₂heteroaryl; provided that R⁶ and R⁷ are not both hydrogen;

R⁸ is hydrogen, —C₁₋₆alkyl, aryl or —C₁₋₆alkylenearyl;

R⁹ is —C₁₋₆alkyl, —C₂₋₆alkenyl, —C₂₋₆alkynyl, cycloalkyl, cycloalkenyl, aryl, heterocyclyl, heteroaryl, arylcycloalkyl-, arylcycloalkenyl-, arylaryl-, arylheterocyclyl- or arylheteroaryl-;

W is a covalent bond, —O—, —S—, —SO—, —SO₂— —N(R⁸)—, —C(=O)—, —N(R⁸)C(=O)—, —C(=O)N(R⁸)—, —C₁₋₄alkylene-, —C₂₋₄alkenylene-, —C₂₋₄alkynylene-, —C₁₋₃alkyleneQC₁₋₃alkylene-, -QC₁₋₄alkylene-, -QC₂₋₄alkenylene-, -QC₂₋₄alkynylene-, —C₁₋₄alkyleneQ-, —C₂₋₄alkenyleneQ-, —C₂₋₄alkynyleneQ- -QC₁₋₄alkyleneQ-, -QC₂₋₄alkenyleneQ- or —OC₂₋₄alkynyleneQ-;

Q is —O—, —S—, —SO—, —SO₂— —N(R⁸)—, —C(=O)—, —N(R⁸)C(=O)—, —C(=O)N(R⁸)—,

Z is -cycloalkyl-, -cycloalkenyl-, -aryl-, -heterocyclyl- or -heteroaryl-;

J is a covalent bond or —C₁₋₆alkylene-, —C₂₋₆alkenylene- or —C₂₋₆alkynylene, in which one —CH₂— group in the alkylene, alkenylene or alkynylene group may be replaced by —O—, —S—, —S(O)—, —S(O)₂— —N(R⁸)—, —C(=O)—, —C(=O)NH— or —NHC(=O)—;

R¹⁰ is cycloalkyl, cycloalkenyl, aryl, heterocyclyl or heteroaryl; and wherein each cycloalkyl, cycloalkenyl, aryl, heterocyclyl and heteroaryl may be optionally substituted;

or a pharmaceutically acceptable salt thereof.

In particular embodiments of formula (I), one or more of the following applies:

R¹ is —C(=O)CHR⁶R⁷, —C(=O)NR⁶R⁷, especially —C(=O)CH(aryl)(aryl), —C(=O)CH(aryl)(cycloalkyl), —C(=O)CH(cycloalkyl)(cycloalkyl), —C(=O)CH(aryl)(alkyl), —C(=O)N(aryl)(aryl), —C(=O)N(aryl)(cycloalkyl), —C(=O)N(cycloalkyl)(cycloalkyl) or —C(=O)N(aryl)(alkyl), where each aryl or cycloalkyl group is optionally substituted; more especially —C(=O)CH(phenyl)(phenyl), —C(=O)CH(phenyl)(cyclohexyl), —C(=O)N(phenyl)(phenyl) or —C(=O)N(phenyl)(cyclohexyl), wherein each phenyl or cyclohexyl group is optionally substituted with one or more substituents selected from —C₁₋₃alkyl, —OC₁₋₃alkyl and halo, especially methyl, methoxy and fluoro; most especially where R¹ is —C(=O)CH(phenyl)(phenyl) and —C(=O)N(phenyl)(phenyl);

R² is —C₁₋₆alkyl, —C₂₋₆alkenyl, —C₂₋₆alkynyl, cycloalkyl, cycloalkenyl, aryl, heterocyclyl, heteroaryl, heterocyclylaryl, -heterocyclylC₁₋₃alkylenearyl, -heteroarylC₁₋₄alkylenearyl, —C₁₋₄alkylenecycloalkyl, —C₁₋₄alkylenecycloalkenyl, —C₁₋₄alkylenearyl, —C₁₋₄ alkyleneheterocyclyl, —C₁₋₄alkyleneheteroaryl, —C₂₋₄alkenylenecycloalkyl, —C₂₋₄alkenylenecycloalkenyl, —C₂₋₄alkenylenearyl, —C₂₋₄alkenyleneheterocyclyl, —C₂₋₄alkenyleneheteroaryl, C₂₋₄alkynylenecycloalkyl, —C₂₋₄alkynylenecycloalkenyl, —C₂₋₄alkynylenearyl, —C₂₋₄alkynyleneheterocyclyl, —C₂₋₄alkynyleneheteroaryl, —Ocycloalkyl, —Ocycloalkenyl, —Oaryl, —Oheterocyclyl, —Oheteroaryl, —OC₁₋₃alkylenecycloalkyl, —OC₁₋₃alkylenecycloalkenyl, —OC₁₋₃alkylenearyl, —OC₁₋₃alkyleneheterocyclyl, —OC₁₋₃alkyleneheteroaryl, —OC₂₋₃alkenylenecycloalkyl, —OC₂₋₃alkenylenecycloalkenyl, —OC₂₋₃alkenylenearyl, —OC₂₋₃alkenyleneheterocyclyl, —OC₂₋₃alkenyleneheteroaryl, —OC₂₋₃alkynylenecycloalkyl, —OC₂₋₃alkynylenecycloalkenyl, —OC₂₋₃alkynylenearyl, —OC₂₋₃alkynyleneheterocyclyl, —OC₂₋₃alkynyleneheteroaryl, —C₁₋₃alkyleneOcycloalkyl, —C₁₋₃alkyleneOcycloalkenyl, —C₁₋₃alkyleneOaryl, —C₁₋₃alkyleneOheterocyclyl, —C₁₋₃alkyleneOheteroaryl, —OC₁₋₃alkylenecycloalkylaryl, —OarylOaryl, —OarylOC₁₋₃alkylenearyl, —NHcycloalkyl, —NHcycloalkenyl, —NHaryl, —NHheterocyclyl, —NHheteroaryl, —NHC₁₋₃alkylenecycloalkyl, —NHC₁₋₃alkylenecycloalkenyl, —NHC₁₋₃alkylenearyl, —NHC₁₋₃alkyleneheterocyclyl, —NHC₁₋₃alkyleneheteroaryl, —NHC₂₋₃alkenylenecycloalkyl, —NHC₂₋₃alkenylenecycloalkenyl, —NHC₂₋₃alkenylenearyl, —NHC₂₋₃alkenyleneheterocyclyl, —NHC₂₋₃alkenyleneheteroaryl, —NHC₂₋₃alkynylenecycloalkyl, —NHC₂₋₃alkynylenecycloalkenyl, —NHC₂₋₃alkynylenearyl, —NHC₂₋₃alkynyleneheterocyclyl, —NHC₂₋₃alkynyleneheteroaryl, —N(CH₃)(C₁₋₈alkyl), —N(CH₃)(C₂₋₈alkenyl), —N(CH₃)(C₂₋₈alkynyl), —N(CH₃)(C₁₋₃alkyleneCF₃), —N(CH₃)(C₂₋₈alkenylCF₃), —N(CH₃)(C₂₋₃alkynyleneCF₃), —N(CH₃)cycloalkyl, —N(CH₃)cycloalkenyl, —N(CH₃)aryl, —N(CH₃)heterocyclyl, —N(CH₃)heteroaryl, —N(CH₃)C₁₋₃alkylenecycloalkyl, —N(CH₃)C₁₋₃alkylenecycloalkenyl, —N(CH₃)C₁₋₃alkylenearyl, —N(CH₃)C₁₋₃alkyleneheterocycyl, —N(CH₃)C₁₋₃alkyleneheteroaryl, —N(CH₃)C₂₋₃alkenylenecycloalkyl, —N(CH₃)C₂₋₃alkenylenecycloalkenyl, —N(CH₃)C₂₋₃alkenylenearyl, —N(CH₃)C₂₋₃alkenyleneheterocyclyl, —N(CH₃)C₂₋₃alkenyleneheteroaryl, —N(CH₃)C₂₋₃alkynylenecycloalkyl, —N(CH₃)C₂₋₃alkynylenecycloalkenyl, —N(CH₃)C₂₋₃alkynylenearyl, —N(CH₃)C₂₋₃alkynyleneheterocyclyl, —N(CH₃)C₂₋₃alkynyleneheteroaryl, —OCH₂CH(phenyl)CH₂(phenyl), —OCH₂C(phenyl)=CH(phenyl), —CHC(=O)NHCH₂cycloalkyl, —CHC(=O)NHCH₂cycloalkenyl, —CHC(=O)NHCH₂aryl, —CHC(=O)NHCH₂heterocyclyl, —CHC(=O)NHCH₂heteroaryl, —C(=O)NHC₁₋₃alkylenecycloalkyl, —C(=O)NHC₁₋₃alkylenecycloalkenyl, —C(=O)NHC₁₋₃alkylenearyl, —C(=O)NHC₁₋₃alkyleneheterocyclyl, —C(=O)NHC₁₋₃alkyleneheteroaryl, —CH₂SO₂C₁₋₃alkylenecycloalkyl, —CH₂SO₂C₁₋₃alkylenecycloalkenyl, —CH₂SO₂C₁₋₃alkylenearyl, —CH₂SO₂C₁₋₃alkyleneheterocyclyl, —CH₂SO₂C₁₋₃alkyleneheteroaryl, —CH₂OC₁₋₃alkylenecycloalkyl, —CH₂OC₁₋₃alkylenecycloalkenyl, —CH₂OC₁₋₃alkylenearyl, —CH₂OC₁₋₃alkyleneheterocyclyl, —CH₂OC₁₋₃alkyleneheteroaryl or —NHC(=O)N(aryl)₂, especially —CH₂phenyl, —CH₂CH₂phenyl, —CH₂CH₂CH₂phenyl, —OCH₂phenyl, —OCH₂CH₂phenyl, —OCH₂CH₂CH₂phenyl, —CH₂CH=CHphenyl, —OCH₂CH=CHphenyl, —OCH₂C≡Cphenyl, —CH₂C≡Cphenyl, —CH₂OCH₂phenyl, —CH₂Ophenyl, —N(CH₃)(2-phenylpropyl), —N(CH₃)(3-phenylpropyn-1-yl), —N(CH₃)(phenethyl), -3-benzylmorpholine, —N(CH₃)(benzyl), —N(CH₃)(CH₂C≡CCH₃), —N(CH₃)(CH₂C≡CCH(CH₃)₂, —N(CH₃)(CH₂C≡C-4-fluorophenyl), —N(CH₃)(CH₂-4-phenyl-tetrazolyl), —N(CH₃)(CH₂-2-phenyl-1-cyclopent-1-enyl), —OCH₂C≡C-4-fluorophenyl, —N(CH₃)(CH₂C≡CCF₃), —N(CH₃)(CH₂C≡C—C(CH₃)₃, -3-phenylpiperidine, —N(CH₃)(CH₂C≡Cphenyl); aryl or alkylaryl substituted oxazolyl such as 2-(5-phenyl)oxazolyl and 2-(5-benzyl)oxazolyl;

one of R³ᵃ and R³ᵇ is hydrogen and the other is —CO₂H, —CH₂CO₂H, —C(=O)NH₂, —CH₂C(=O)NH₂—CN, —CH₂CN, —C(=O)C(=O)OH, —C(=O)NHSO₂N(C₁₋₆alkyl)₂, —C(=O)NHSO₂C₁₋₆alkyl, —C(=O)NHSO₂phenyl, —C(=O)NHSO₂CF₃, tetrazolyl, —CH₂tetrazolyl, —SO₃H or —PO₃H₂, especially —CO₂H, —CH₂CO₂H, —C(=O)NH₂, —CN, tetrazolyl, —C(=O)NHSO₂C₁₋₄alkyl, —C(=O)NHSO₂N(C₁₋₄alkyl)₂, —C(=O)NHSO₂phenyl or —C(=O)NHSO₂CF₃, more especially —CO₂H; especially where R³ᵇ is hydrogen and R³ᵃ is —CO₂H, —CH₂CO₂H, —C(=O)C(=O)OH, —C(=O)NH₂, —CH₂C(=O)NH₂, —CN, —C(=O)NHSO₂C₁₋₆alkyl, —C(=O)NHSO₂N(C₁₋₆alkyl)₂, —C(=O)NHSO₂phenyl, —C(=O)NHSO₂CF₃, —C(=O)

NHSO$_2$N(CH$_3$)$_2$, —C(=O)NHSO$_2$N(CH$_3$)$_2$, tetrazolyl, —CH$_2$tetrazolyl —SO$_3$H or —PO$_3$H$_2$, especially —CO$_2$H, —CH$_2$CO$_2$H, tetrazolyl, —C(=O)NHSO$_2$C$_{1-4}$alkyl, —C(=O)NHSO$_2$N(C$_{1-4}$alkyl)$_2$, —C(=O)NHSO$_2$phenyl, —C(=O)NHSO$_2$CF$_3$, —C(=O)NHSO$_2$N(CH$_3$)$_2$, —C(=O)NH$_2$ or —CN, more especially —CO$_2$H;

R$^4$ is hydrogen or together with R$^2$ forms an aryl, heteroaryl or heterocyclyl ring selected from:

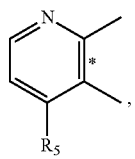

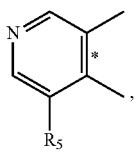

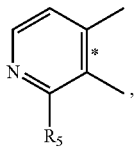

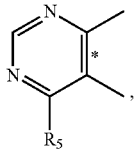

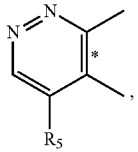

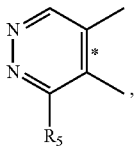

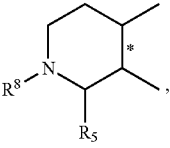

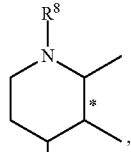

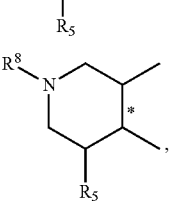

-continued

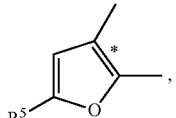

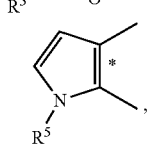

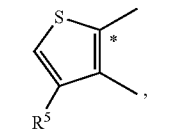

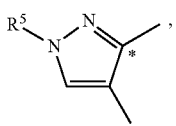

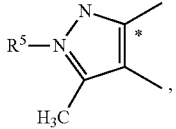

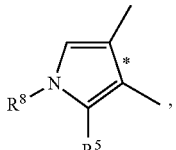

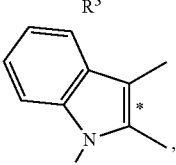

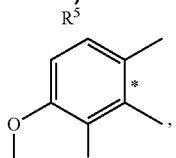

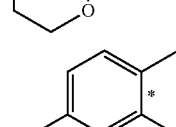

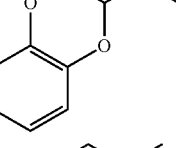

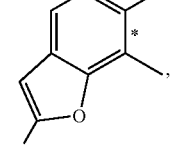

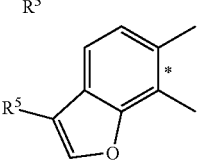

where * indicates the fused bond and $R^5$ is selected from aryl, —$C_{1-3}$alkylenearyl, —Oaryl, —O$C_{1-3}$alkylenearyl, —$C_{1-3}$alkyleneOaryl, —$C_{1-3}$ alkyleneO$C_{1-3}$alkylenearyl, -heterocyclyl, -heterocyclylaryl, -heterocyclyl$C_{1-3}$alkylenearyl, -heteroaryl, -heteroarylaryl and -heteroaryl$C_{1-3}$alkylenearyl, especially phenyl, benzyl, phenoxy, benzyloxy, —$CH_2CH_2$phenyl, —$CH_2CH_2CH_2$phenyl, —$CH_2OCH_2$phenyl, —$OCH_2CH_2$phenyl, —$CH_2O$phenyl, 2-(5-phenyl)oxazole and 2-(5-benzyl)oxazole;

$R^6$ and $R^7$ are independently selected from phenyl and cyclohexyl, especially where both $R^6$ and $R^7$ are phenyl; and $R^8$ is hydrogen, methyl, ethyl, phenyl, -propylphenyl, -propynylphenyl, -ethylphenyl, —$CH_2$phenyl, -butynyl, -4-methylpropyn-2-yl, -propynyl-4-fluorophenyl, —$CH_2$-(4-phenyl-tetrazolyl), —$CH_2$-(2-phenylcyclopentenyl), —$CH_2C\equiv C-CF_3$ or —$CH_2C\equiv C-C(CH_3)_2$.

In some embodiments, especially when $R^{3a}$ a carboxylic acid, —$CH_2CO_2H$, —C(=O)C(=O)OH, —$CONH_2$, —CN or a carboxylic acid bioisostere, $R^{3a}$ has an S stereochemistry.

Particular compounds of formula (II) are:

| Compound | $R^1$ | $R^2$ | $R^{3a}$ | Relative Stereochem $R^3/R^{3a}$ | $R^{3b}$ | $R^4$ | $R^2/R^4$ |
|---|---|---|---|---|---|---|---|
| 1 | —C(O)CH(phenyl)$_2$ | — | —CO$_2$H (S) | — | H | — | 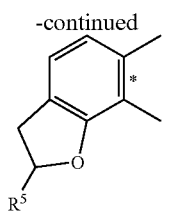 |
| 2 | —C(O)CH(phenyl)$_2$ | — | —CO$_2$H (S) | — | H | — | |
| 3 | —C(O)CH(phenyl)$_2$ | — | —CO$_2$H (S) | — | H | — | |

-continued
| Compound | R¹ | R² | R³ᵃ | Relative Stereochem R³/R³ᵃ | R³ᵇ | R⁴ | R²/R⁴ |
|---|---|---|---|---|---|---|---|
| 4 | —C(O)CH(phenyl)₂ | — | —CO₂H (S) | — | H | — | 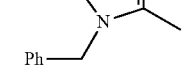 |
| 5 | —C(O)CH(phenyl)₂ | — | —CO₂H (S) | — | H | — | 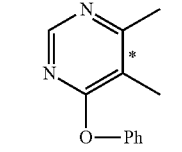 |
| 6 | —C(O)CH(phenyl)₂ | — | —CO₂H (S) | — | H | — | 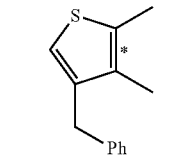 |
| 7 | —C(O)CH(phenyl)₂ | — | —CO₂H (S) | — | H | — | 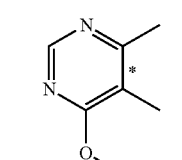 |
| 8 | —C(O)CH(phenyl)₂ | — | —CO₂H (S) | — | H | — | 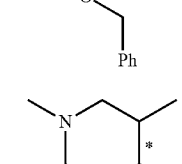 |
| 9 | —C(O)CH(phenyl)₂ | — | —CO₂H (S) | — | H | — | 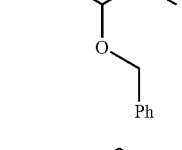 |
| 10 | —C(O)CH(phenyl)₂ | — | —CO₂.H (S) | — | H | — | 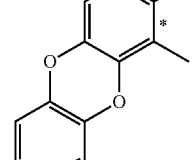 |
| 11 | —C(O)CH(phenyl)₂ | — | —CO₂H (S) | — | H | — | 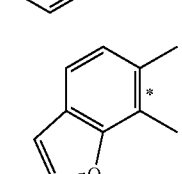 |

-continued

| Compound | R¹ | R² | R³ᵃ | Relative Stereochem R³/R³ᵃ | R³ᵇ | R⁴ | R²/R⁴ |
|---|---|---|---|---|---|---|---|
| 12 | —C(O)CH(phenyl)₂ | — | —CO₂H (S) | — | H | — | 2-benzyl-6,7-dimethylbenzofuran |
| 13 | —C(O)CH(phenyl)₂ | — | —CO₂H (S) | — | H | — | 1-phenyl-4,5-dimethylindazole |
| 14 | —C(O)CH(phenyl)₂ | — | —CO₂H (S) | — | H | — | 1-benzyl-4,5-dimethylindazole |
| 15 | —C(O)CH(phenyl)₂ | — | —CO₂H (S) | — | H | — | 2-phenyl-6,7-dimethyl-2,3-dihydrobenzofuran |
| 16 | —C(O)CH(phenyl)₂ | — | —CO₂H (S) | — | H | — | 3-phenyl-6,7-dimethyl-2,3-dihydrobenzofuran |
| 17 | —C(O)CH(phenyl)₂ | — | H | — | CO₂H (S) | — | 5-phenyl-2,3-dimethylfuran |
| 18 | —C(O)CH(phenyl)₂ | — | H | — | —CO₂H (S) | — | 5-benzyl-2,3-dimethylfuran |
| 19 | —C(O)CH(phenyl)₂ | — | H | — | —CO₂H (S) | — | 1-phenyl-3,4-dimethylpyrazole |
| 20 | —C(O)CH(phenyl)₂ | — | H | — | —CO₂H (S) | — | 1-benzyl-3,4,5-trimethylpyrazole |
| 21 | —C(O)CH(phenyl)₂ | —CH₂CH₂CH₂phenyl | —CO₂H (S) | cis/trans | H | H | — |
| 22 | —C(O)CH(phenyl)₂ | —CH₂CH₂phenyl | —CO₂H (S) | cis/trans | H | H | — |
| 23 | —C(O)CH(phenyl)₂ | —CH₂OCH₂phenyl | —CO₂H (S) | cis/trans | H | H | — |
| 24 | —C(O)CH(phenyl)₂ | —OCH₂CH₂phenyl | —CO₂H (S) | cis/trans | H | H | — |
| 25 | —C(O)CH(phenyl)₂ | —CH₂Ophenyl | —CO₂H (S) | cis/trans | H | H | — |

-continued

| Compound | R$^1$ | R$^2$ | R$^{3a}$ | Relative Stereochem R$^3$/R$^{3a}$ | R$^{3b}$ | R$^4$ | R$^2$/R$^4$ |
|---|---|---|---|---|---|---|---|
| 26 | —C(O)CH(phenyl)$_2$ | —OCH$_2$phenyl | —CO$_2$H (S) | cis/trans (1:9) | H | H | — |
| 27 | —C(O)CH(phenyl)$_2$ | -2-(5-phenyl)-oxazole | —CO$_2$H (S) | cis/trans | H | H | — |
| 28 | —C(O)CH(phenyl)$_2$ | -2-(5-benzyl)-oxazole | —CO$_2$H (S) | cis/trans | H | H | — |
| 29 | —C(O)CH(phenyl)$_2$ | —OCH$_2$phenyl | —CO$_2$H (S) | trans | H | H | — |
| 30 | —C(O)CH(phenyl)$_2$ | —OCH$_2$phenyl | —CO$_2$H (S) | cis/trans (7:3) | H | H | — |
| 31 | —C(O)CH(phenyl)$_2$ | —N(CH$_3$)(2-phenylpropyl) | —CO$_2$H (S) | cis | H | H | — |
| 32 | —C(O)CH(phenyl)$_2$ | —N(CH$_3$)(3-phenyl-2-propyn-1-yl) | —CO$_2$H (S) | cis | H | H | — |
| 33 | —C(O)CH(phenyl)$_2$ | —N(CH$_3$)(3-phenyl-2-propyn-1-yl) | —CO$_2$H (S) | trans | H | H | — |
| 34 | —C(O)CH(phenyl)$_2$ | —N(CH$_3$)(phenethyl) | —CO$_2$H (S) | cis | H | H | — |
| 35 | —C(O)CH(phenyl)$_2$ | —N(CH$_3$)(phenethyl) | —CO$_2$H (S) | trans | H | H | — |
| 36 | —C(O)CH(phenyl)$_2$ | -3-benzylmorpholine | —CO$_2$H (S) | cis | H | H | — |
| 37 | —C(O)CH(phenyl)$_2$ | -3-benzylmorpholine | —CO$_2$H (S) | trans | H | H | — |
| 38 | —C(O)CH(phenyl)$_2$ | —N(CH$_3$)(benzyl) | —CO$_2$H (S) | cis | H | H | — |
| 39 | —C(O)CH(phenyl)$_2$ | —N(CH$_3$)(benzyl) | —CO$_2$H (S) | trans | H | H | — |
| 40 | —C(O)CH(phenyl)$_2$ | —OCH$_2$C≡Cphenyl | —CO$_2$H (S) | cis | H | H | — |
| 41 | —C(O)CH(phenyl)$_2$ | —OCH$_2$CH$_2$CH$_2$phenyl | —CO$_2$H (S) | cis | H | H | — |
| 42 | —C(O)CH(phenyl)$_2$ | —N(CH$_3$)(CH$_2$C≡CCH$_3$) | —CO$_2$H (S) | cis | H | H | — |
| 43 | —C(O)CH(phenyl)$_2$ | —N(CH$_3$)(CH$_2$C≡CCH$_3$) | —CO$_2$H (S) | trans | H | H | — |
| 44 | —C(O)CH(phenyl)$_2$ | —N(CH$_3$)(CH$_2$C≡CCH(CH$_3$)$_2$) | —CO$_2$H (S) | cis | H | H | — |
| 45 | —C(O)CH(phenyl)$_2$ | —N(CH$_3$)(CH$_2$C≡CCH(CH$_3$)$_2$) | —CO$_2$H (S) | trans | H | H | — |
| 46 | —C(O)CH(phenyl)$_2$ | —N(CH$_3$)(CH$_2$C≡C-4-fluorophenyl) | —CO$_2$H (S) | cis | H | H | — |
| 47 | —C(O)CH(phenyl)$_2$ | —N(CH$_3$)(CH$_2$C≡C-4-fluorophenyl) | —CO$_2$H (S) | trans | H | H | — |
| 48 | —C(O)CH(phenyl)$_2$ | —N(CH$_3$)(CH$_2$-4-phenyl-5-tetrazolyl) | —CO$_2$H (S) | cis | H | H | — |
| 49 | —C(O)CH(phenyl)$_2$ | —N(CH$_3$)(CH$_2$-2-phenyl-1-cyclopent-1-enyl) | —CO$_2$H (S) | cis | H | H | — |
| 50 | —C(O)CH(phenyl)$_2$ | -5-benzyl-2-oxazolyl | —CO$_2$H (S) | cis | H | H | — |
| 51 | —C(O)CH(phenyl)$_2$ | -5-phenyl-2-oxazolyl | —CO$_2$H (S) | cis | H | H | — |
| 52 | —C(O)CH(phenyl)$_2$ | —OCH$_2$C≡C-4-fluorophenyl | —CO$_2$H (S) | cis | H | H | — |
| 53 | —C(O)CH(phenyl)$_2$ | —N(CH$_3$)(CH$_2$C≡CCF$_3$) | —CO$_2$H (S) | cis | H | H | — |
| 54 | —C(O)CH(phenyl)$_2$ | —N(CH$_3$)(CH$_2$C≡C—C(CH$_3$)$_3$) | —CO$_2$H (S) | cis | H | H | — |
| 55 | —C(O)CH(phenyl)$_2$ | -3R-phenylpiperidine | —CO$_2$H (S) | cis | H | H | — |
| 56 | —C(O)CH(phenyl)$_2$ | -3R-phenylpiperidine | —CO$_2$H (S) | trans | H | H | — |
| 57 | —C(O)CH(phenyl)$_2$ | -3S-phenylpiperidine | —CO$_2$H (S) | cis | H | H | — |
| 58 | —C(O)CH(phenyl)$_2$ | -3S-phenylpiperidine | —CO$_2$H (S) | trans | H | H | — |
| 59 | —C(O)CH(phenyl)$_2$ | —N(CH$_3$)(CH$_2$C≡Cphenyl) | —CONH$_2$(S) | cis | H | H | — |
| 60 | —C(O)CH(phenyl)$_2$ | —N(CH$_3$)(CH$_2$C≡Cphenyl) | —CN (S) | cis | H | H | — |
| 61 | —C(O)CH(phenyl)$_2$ | —N(CH$_3$)(CH$_2$C≡Cphenyl) | -tetrazolyl(S) | cis | H | H | — |
| 62 | —C(O)CH(phenyl)$_2$ | —N(CH$_3$)(CH$_2$C≡Cphenyl) | —CONHSO$_2$N(CH$_3$)$_2$ (S) | cis | H | H | — |

Particular compounds of the formula (II) include compounds 1, 9, 26, 30, 32, 35, 40, 41, 44, 45, 46, 52, 54, 55, 56 and 58, especially 30, 35, 41 and 54.

In some embodiments, the compounds of formula (I) are selective AT$_2$ receptor antagonists. In particular embodiments, the selective AT$_2$ receptor antagonists have an IC$_{50}$ at the AT$_2$ receptor of ≤100 nM and an IC$_{50}$ at the AT$_1$ receptor of >100,000 nM (10 μM) using the assay methodologies described in Biological Examples 1 and 2.

The compounds of the invention are made by methods known in the art from commercially available starting materials.

Compounds of formula (I) in which R$^2$ and R$^4$ form a fused heteroaryl ring system can be prepared by building a piperidine ring onto the heteroaryl or heterocyclyl group. For example, the heterocyclyl or heteroaryl group may be derivatized at an appropriate position to include an aldehyde group. This may be done by oxidation from a primary alcohol or reduction of a carboxylic acid as known in the art or the aldehyde may be introduced directly on an aryl ring, for example, by treatment with n-butyl lithium and dimethyl formaldehyde.

The nitrogen atom of the piperidine ring together with the carboxylic acid group, may be introduced by reaction of the aldehyde with a suitable phosphoronic or phosphonate ylide using a Wittig reaction or Horner-Emmons reaction. The resulting double bond may be stereoselectively reduced using chiral catalysts in the presence of hydrogen. Suitable chiral ligands and catalysts include BoPhoz™, P-Phos, Xylyl-P-Phos, Xylyl-phanePhos, Me-BoPhoz, which are available in both R and S configurations, Rh(COD)$_2$BF$_4$, (S)-paraphos RuCl$_2$ (R,R)-DPEN, (R)-Xylyl-P-Phos RuCl$_2$ (R,R)-DPEN, [(S)-Paraphos Rh(NBD)]BF$_4$ and (R)—P-Phos Ru (acac)$_2$. Selection of an appropriate chiral ligand and catalyst can be used to determine the stereochemistry of the carboxylic acid group on the piperidine ring.

Finally, the piperidine ring may be formed from a salt of the amino group by reaction with formaldehyde in acidic solution, for example, in the presence of phosphoric acid. This reaction inserts a —CH$_2$— group between the piperidine nitrogen atom and the heterocyclyl or heteroaryl group.

Substituted piperidines may be prepared from suitably protected substituted piperidines that are commercially available or synthesized by known literature procedures. For example, a 4-oxo substituted 2-carboxymethyl N-Boc-piperidine may be prepared and the keto group used to introduce $R^2$ or $R^4$.

For example, the keto group can be reduced to a hydroxy group and subsequently arylated or alkylated by methods known in the art. In one approach, alkyl or aryl groups may be introduced at $R^2$ or $R^4$ by reaction of the hydroxy group with a suitable alcohol such as phenol, in the presence of triphenylphosphine ($PPh_3$) and DBAD. In another approach the hydroxy group may be activated, such as by formation of a mesylate or the hydroxy group may be replaced with a halide atom and reaction with a suitable alkyl or aryl group is undertaken. In some cases, where epimerization of a group adjacent to the carboxylic acid is a problem, silver oxide mediated alkylation may be used. The keto group can be treated with phosphorus or phosphonate ylids to introduce a functionalized group attached to the ring with a double bond, which may be optionally reduced. Amino substituents may be introduced by formation of an imine, iminium salt, oxime or hydrazone from the keto group and subsequent reaction to provide an amino group, substituted amino group, amide, sulphonamide and the like.

$R^1$ may be introduced either before the introduction of $R^2$ or $R^4$ or after the introduction of $R^2$ or $R^4$, or after formation of the fused piperidinyl ring. If $R^2$ is introduced prior to the introduction of $R^1$, it may be necessary to protect the ring nitrogen during the alkylation reaction. Suitable nitrogen protecting groups are known in the art, for example, in Greene & Wutz, Protective Groups in Organic Synthesis, Third Edition, John Wiley & Sons, 1999. A suitable nitrogen protecting group is t-butoxycarbonyl (Boc).

$R^1$ may be introduced by amide formation with a suitable carboxylic acid and the ring nitrogen. Amide formation is well known in the art and may involve the activation of the carboxylic acid, for example, the carboxy group is activated by formation of an acid chloride, carbodiimide, triazole or a uronium or phosphonium salt of a non-nucleophilic anion. Suitable activating groups are well known in the art including dicyclohexylcarbodiimide (DCC), diisopropylcarbodiimide (DIC), 1-ethyl-3-(dimethylaminopropyl)carbodiimide (EDCI), 1-hydroxybenzotriazole (HOBt), 1-hydroxy-7-azabenzotriazole (HOAt), ethyl-2-cyano-2-cyano-2-(hydroxyimino)acetate (Oxyma Pure), O-benzotriazole-N,N,N',N'-tetramethyluronium hexafluorophosphate (HBTU), O-(7-azabenzotriazol-1-yl)-N,N,N',N'-tetramethyluronium hexafluorophosphate (HATU), O-(6-chloro-1H-benzotriazol-1-yl)-1,1,3,3-tetramethyluronium tetrafluorophosphate (HCTU), O-benzotriazol-1-yl-N,N,N'N'-tetramethyluronium tetrafluoroborate (TBTU), (benzotriazol-1-yloxy) tripyrrolidinophosphonium hexafluorophosphate (PyBOP); (benzotriazol-1-yloxy)-tris-(dimethylamino)phosphonium hexafluorophosphate (BOP), (1-cyano-2-ethoxy-2-oxoethylidenaminooxy)-dimethylamino-morpholino-carbenium hexafluorophosphate (COMU) and O-[(ethoxycarbonyl)-cyanomethyleneamino]-N,N,N',N'-tetramethyluronium tetrafluoroborate (TOTU).

During any synthetic procedure, reactive functional groups may require protecting to avoid unwanted reaction and to ensure reaction at a specified site. Suitable protecting groups are known in the art and may be found in Greene & Wutz, ibid.

Methods of the Invention

In one aspect of the present invention, there is provided a method of treating or preventing the symptoms of a neuropathic condition in a subject comprising administering a compound of formula (I) or a pharmaceutically acceptable salt thereof.

The compounds of formula (I) are effective in the prevention or attenuation of the symptoms of neuropathic conditions including primary and secondary neuropathic conditions. In accordance with the present invention, the compounds of formula (I) can act to treat, prevent or attenuate one or more symptoms associated with neuropathic conditions including, but not limited to, hyperesthesia, hyperalgesia, allodynia and/or spontaneous burning pain. In some embodiments, the compound of formula (I) is used to prevent or attenuate one or more symptoms associated with peripheral neuropathic conditions, illustrative examples of which include numbness, weakness, burning pain, shooting pain, and loss of reflexes. The pain may be severe and disabling. In some embodiments, the symptom, which is the subject of the prevention and/or attenuation, is neuropathic pain. Accordingly, in a related aspect, the invention provides methods for preventing and/or attenuating neuropathic pain in an individual, comprising administering to the individual a pain-preventing or -attenuating effective amount of an $AT_2$ receptor antagonist, which is suitably in the form of a pharmaceutical composition.

There are many possible causes of neuropathy and neuropathic pain and it will be understood that the present invention contemplates the treatment or prevention of symptoms of any neuropathic condition regardless of the cause. In some embodiments, the neuropathic conditions are a result of diseases of the nerves (primary neuropathy) and neuropathy that is caused by systemic disease (secondary neuropathy) such as but not limited to: diabetic neuropathy; Herpes Zoster (shingles)-related neuropathy; uremia-associated neuropathy; amyloidosis neuropathy; HIV sensory neuropathies; hereditary motor and sensory neuropathies (HMSN); hereditary sensory neuropathies (HSNs); hereditary sensory and autonomic neuropathies; hereditary neuropathies with ulcero-mutilation; nitrofurantoin neuropathy; tomaculous neuropathy; neuropathy caused by nutritional deficiency, neuropathy caused by kidney failure and complex regional pain syndrome. Other causes include repetitive activities such as typing or working on an assembly line, medications known to cause peripheral neuropathy such as several anti-retroviral drugs (ddC (zalcitabine) and ddI (didanosine), antibiotics (metronidazole, an antibiotic used for Crohn's disease, isoniazid used for tuberculosis), gold compounds (used for rheumatoid arthritis), some chemotherapy drugs (such as vincristine and others) and many others. Chemical compounds are also known to cause peripheral neuropathy including alcohol, lead, arsenic, mercury and organophosphate pesticides. Some peripheral neuropathies are associated with infectious processes (such as Guillian-Barre syndrome). In certain embodiments, the neuropathic condition is a peripheral neuropathic condition, which is suitably pain secondary to mechanical nerve injury or painful diabetic neuropathy (PDN) or related condition.

The neuropathic condition may be acute or chronic and, in this connection, it will be understood by persons of skill in the art that the time course of a neuropathy will vary, based on its underlying cause. With trauma, the onset of symptoms may be acute, or sudden; however, the most severe symptoms may develop over time and persist for years. Inflammatory and some metabolic neuropathies have a subacute course extending over days to weeks. A chronic course over weeks to months usually indicates a toxic or metabolic neuropathy. A chronic, slowly progressive neuropathy over many years such as occurs with painful diabetic neuropathy or with most hereditary neuropathies or with a condition termed chronic inflammatory demyelinating polyradiculoneuropathy (CIDP). Neuropathic conditions with symptoms that relapse and remit include the Guillian-Barré syndrome.

In another aspect of the invention there is provided a method of treating or preventing a condition characterized by neuronal hypersensitivity in a subject comprising administering a compound of formula (I) or a pharmaceutically acceptable salt thereof.

In some embodiments, the condition characterized by neuronal hypersensitivity is a hyperalgesic condition such as fibromyalgia. In other embodiments, the condition is irritable bowel syndrome which is characterized by neuronal hypersensitivity in the gut.

In another aspect of the invention there is provided a method of treating or preventing a disorder associated with aberrant nerve regeneration comprising administering a compound of formula (I) or a pharmaceutically acceptable salt thereof.

In some embodiments, the disorder associated with aberrant nerve regeneration also includes neuronal hypersensitivity. Examples of disorders associated with aberrant nerve regeneration are breast pain, interstitial cystitis and vulvodynia. In other embodiments, the disorder is a cancer chemotherapy-induced neuropathy.

In another aspect of the invention, there is provided a method of treating or preventing inflammatory pain in a subject comprising administering a compound of formula (I) or a pharmaceutically acceptable salt thereof.

Pain related to inflammation may be acute or chronic and can be due to a number of conditions that are characterized by inflammation including, without limitation, burns such as chemical, frictional or chemical burns, autoimmune diseases such as rheumatoid arthritis and osteoarthritis, inflammatory bowel disease such as Crohn's disease and colitis, and other inflammatory diseases such as inflammatory bowel disease, carditis, dermatitis, myositis, neuritis and collagen vascular diseases.

In a further aspect, the present invention provides a method of treating or preventing impaired nerve conduction velocity in a subject comprising administering a compound of formula (I) or a pharmaceutically acceptable salt thereof.

Impaired neuronal conduction velocity is a symptom of nerve dysfunction or damage and may be present as a symptom of a large number of diseases or disorders, particularly diseases or disorders that exhibit paresthesia as a symptom. In some embodiments, the impaired nerve conduction velocity is associated with a neuropathic condition as described above. In other embodiments, the impaired nerve conduction velocity is associated with Carpel Tunnel Syndrome, ulnar neuropathy, Guillian-Barré Syndrome, fascioscapulohumeral muscular dystrophy and spinal disc herneation.

Nerve conduction velocity is assessed by evaluating the electrical conduction of motor and sensory nerves in the body. Motor nerve conduction velocity is measured by stimulation of a peripheral nerve and measuring the time taken for the electrical impulse to be detected in the muscle associated with the nerve. The time taken is measured in milliseconds and is converted to a velocity (m/s) by taking into account the distance traveled. Sensory nerve conduction is assessed in a similar manner with stimulation of a peripheral nerve and recording at a sensory site such as a finger or paw pad.

In yet a further aspect of the invention there is provided a method of producing analgesia in a subject comprising administering a compound of formula (I) or a pharmaceutically acceptable salt thereof.

In some embodiments, the subject is a subject having a neuropathic condition, an inflammatory condition, impaired nerve conduction velocity, a condition characterized by neuronal hypersensitivity or a disorder associated with aberrant nerve regeneration. In other embodiments, the subject is a subject at risk of developing neuropathic pain, inflammatory pain, pain related to impaired nerve conduction velocity, a condition characterized by neuronal hypersensitivity or a disorder associated with aberrant nerve regeneration.

In still another aspect of the invention there is provided a method of treating or preventing a cell proliferative disorder in a subject comprising administering a compound of formula (I) or a pharmaceutically acceptable salt thereof.

In some embodiments, the cell proliferative disorder is a cancer, especially where the cancer is selected from leukaemia, melanoma, prostate cancer, breast cancer, ovarian cancer, basal cell carcinoma, squamous cell carcinoma, sarquoides, fibrosarcoma, colon cancer, lung cancer and other solid tumour cancers.

In other embodiments, the cell proliferative disorder is a non-cancerous proliferative disorder. Examples of such non-cancerous proliferative disorders include dermatological disorders such as warts, keloids, psoriasis, proud flesh disorder and also the reduction in scar tissue and cosmetic remodelling.

In a further aspect the present invention provides a method of treating or preventing a disorder associated with an imbalance between bone resorption and bone formation in a subject comprising administering a compound of formula (I) or a pharmaceutically acceptable salt thereof.

In some embodiments, the disorder associated with an imbalance between bone resorption and bone formation is osteoporosis.

The subjects, individuals or patients to be treated are mammalian subjects including but not limited to humans, primates, livestock animals such as sheep, cattle, pigs, horses, donkeys and goats; laboratory test animals such as mice, rats, rabbits and guinea pigs; companion animals such as cats and dogs or captive wild animals such as those kept in zoos. In a particular embodiment, the subject is a human.

An "effective amount" means an amount necessary at least partly to attain the desired response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials. An effective amount in relation to a human patient, for example, may lie in the range of about 0.1 ng per kg of body weight to 1 g per kg of body weight per dosage. The dosage is preferably in the range of 1 µg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another embodiment, the dosage is in the range of 1 mg to 100 mg per kg of body weight per dosage, such as up to 50 mg per kg of body weight per dosage. In yet another embodiment, the dosage is in the range of 1 µg to 1 mg per kg of body weight per dosage. Dosage regimes may be adjusted to provide the optimum therapeutic response. For example, several divided doses may be administered daily, weekly, monthly or other suitable time intervals, or the dose may be proportionally reduced as indicated by the exigencies of the situation.

Reference herein to "treatment" and "prevention" is to be considered in its broadest context. The term "treatment" does not necessarily imply that a subject is treated until total recovery. "Treatment" may also reduce the severity of an existing condition. The term "prevention" does not necessarily mean that the subject will not eventually contract a disease condition. The term "prevention" may be considered to include delaying the onset of a particular condition. Accordingly, treatment and prevention include amelioration of the symptoms of a particular condition or preventing or otherwise reducing the risk of developing a particular condition.

In some embodiments, the compounds of formula (I) or their pharmaceutically acceptable salts thereof may be administered together with another therapy. Administration may be in a single composition or in separate compositions simultaneously or sequentially such that both compounds or therapies are active at the same time in the body.

In some embodiments, the compounds of formula (I) or their pharmaceutically acceptable salts are administered together with another therapy to treat neuropathic or inflammatory pain or the underlying condition that is causing the neuropathic or inflammatory pain or another therapy to treat conditions characterized by neuronal hypersensitivity, disorders associated with aberrant nerve regeneration, proliferative disorders or disorders associated with an imbalance between bone resorption and bone formation. In some embodiments, the amount of the second drug may be reduced when administration is together with a compound of formula (I) or a pharmaceutically acceptable salt thereof.

Suitable additional drugs to treat pain include opiates such as morphine, codeine, dihydrocodeine, hydrocodone, acetyldihydrocodeine, oxycodone, oxymorphone and buprenorphine, and non-steroidal anti-inflammatory drugs (NSAIDs) such as aspirin, ibuprofen, naproxen, acetaminophen, diflunisal, salsalate, phenacetin, fenoprofen, ketoprofen, flurbiprofen, oxaprozin, loxoprofen, indomethacin, sulindac, etodolac, ketorolac, diclofenac, nabumetone, mefenamic acid, meclofenamic acid, flufenamic acid, tolfenamic acid, celecoxib, parecoxib, lumaricoxib, etoricoxib, firocoxib, rimesulide and licofelone.

Examples of drugs to treat neuropathies include duloxetine, pregabalin, gabapentin, phenytoin, carbamazebine, levocarnitine, tricyclic antidepressants such as amitryptiline and sodium channel blockers such as lidocaine.

Examples of chemotherapy drugs for proliferative disorders include cisplatin, carboplatin, camptothecin, carmustine, cyclophosphamide, dactinomycin, daunorubicin, dexamethasone, docetaxel, doxorubicin, etoposide, epirubicin, everolimus, gemcitibine, goserelin, trastuzumab (Herceptin®), idarubicin, interferon-alfa, irinotecan, methotrexate, mitomycin, oxaliplatin, paclitaxel, raloxifene, streptozocin, tamoxifen, topotecan, vinblastine, vincristine, abiraterone, fluorouracil, denosumab, imatinib, geftinib, lapatinib, pazopanib, rituximab, sunitinib, erlotinib and vorinistat.

Examples of drugs to treat disorders associated with an imbalance between bone formation and bone resorption include bisphosphonates such as sodium alendronate, risedronate and ibandronate, raloxifene, calcitonin, teriparatide, strontium ranelate or calcium supplements.

Examples of drugs used to treat conditions characterized by neuronal hypersensitivity, such as irritable bowel syndrome, include 5HT$_3$ receptor antagonists such as alosetron (Lotronex®).

The AT$_2$ receptor antagonists of the invention are also useful in combination with radiotherapy in cancer patients.

Compositions of the Invention

While it is possible that, for use in therapy, a compound of the invention may be administered as a neat chemical, it is preferable to present the active ingredient as a pharmaceutical composition.

Thus, in a further aspect of the invention, there is provided a pharmaceutical composition comprising a compound of formula (I) or a pharmaceutically acceptable salt thereof and at least one pharmaceutically acceptable carrier.

The carrier(s) must be "acceptable" in the sense of being compatible with the other ingredients of the composition and not deleterious to the recipient thereof.

Pharmaceutical formulations include those suitable for oral, rectal, nasal, topical (including buccal and sub-lingual), vaginal or parenteral (including, intramuscular, sub-cutaneous and intravenous) administration or in a form suitable for administration by inhalation or insufflation. The compounds of the invention, together with a conventional adjuvant, carrier, excipient, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to two hundred (200) milligrams, per tablet, are accordingly suitable representative unit dosage forms. The compounds of the present invention can be administered in a wide variety of oral and parenteral dosage forms. It will be obvious to those skilled in the art that the following dosage forms may comprise, as the active component, either a compound of the invention or a pharmaceutically acceptable salt or derivative of the compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomizing spray pump. To improve nasal delivery and retention the compounds according to the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example, dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP).

Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 1 to 10 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compositions of the invention may comprise further active ingredients such as therapies for treating neuropathic or inflammatory pain or the underlying condition causing the neuropathic or inflammatory pain or therapies for treating impaired nerve conduction velocity, conditions characterized by neuronal hypersensitivity, disorders associated with aberrant nerve regeneration, proliferation disorders or disorder associated with an imbalance between bone resorption and bone formation.

The invention will now be described with reference to the following Examples which illustrate some preferred aspects of the present invention. However, it is to be understood that the particularity of the following description of the invention is not to supersede the generality of the preceding description of the invention.

EXAMPLES

Abbreviations

| | |
|---|---|
| DCM | dichloromethane |
| DBAD | dibenzyl azodicarboxylate |
| RT | room temperature |
| PE | petroleum ether |
| EA or EtOAc | ethyl acetate |
| THF | tetrahydrofuran |
| Et$_2$O | diethyl ether |
| MeOH | methanol |
| DMAP | 4-dimethylaminopyridine |
| Bn | benzyl |
| TLC | thin layer chromatography |
| DCE | 1,2-dichloroethane |
| DMF | dimethylformamide |
| NaH | sodium hydride |
| EDCI | 1-ethyl-3-(3-dimethylaminopropyl)carbodiimide |
| Boc | t-butyloxycarbonyl |
| HCHO | formaldehyde |
| EtOH | Ethanol |
| HMPA | hexamethylphosphoramide |
| BoPhoz ™ | (R)-MethylBoPhoz ™ |
| n-BuLi | n-butyl lithium |
| Rh(COD)$_2$BF$_4$ | Bis(cycloocta-1,5-diene)rhodium (I) tetrafluoroborate |
| AcOH | acetic acid |
| DBU | 1,8-diazabicycloundec-7-ene |

General Methods Used in the Synthesis Examples

LC-MS (Agilent):
1. LC: Agilent Technologies 1200 series, Binary Pump, Diode Array Detector. Ultimate AQ-C18, 3 µm, 2.1×50 mm column. Mobile phase: B (MeOH) and A (0.07% HCOOH aqueous solution). Flow Rate: 0.4 mL/min at 25° C. Detector: 214 nm, 254 nm. Gradient stop time, 5 min. Timetable:

| T (min) | B (%) | A (%) |
|---|---|---|
| 0 | 10 | 90 |
| 0.2 | 10 | 90 |
| 1.2 | 95 | 5 |
| 2.8 | 95 | 5 |
| 3 | 10 | 90 |
| 5 | 10 | 90 |

2. MS: G6110A, Quadrupole LC/MS, Ion Source: ES-API, TIC: 50~900 m/z, Fragmentor: 60, Drying gas flow: 10 L/min, Nebulizer pressure: 35 psi, Drying gas temperature: 350° C., Vcap: 3500V.
3. Sample preparation: samples were dissolved in methanol at 1~10 µg/mL, then filtered through a 0.22 µm filter membrane. Injection volume: 1~10 µL.

LC-MS (Waters):
1. LC: Waters 2695, Quaternary Pump, Waters 2996 Photodiode Array Detector. Xbridge-C18, 3.5 µm, 2.1×50 mm column. Mobile Phase: B (MeOH) and A (0.07% HCOOH aqueous solution). Flow Rate: 0.3 mL/min at 30° C. Detector: 214 nm, 254 nm. Gradient stop time, 10 min. Timetable:

| T (min) | B (%) | A (%) |
|---|---|---|
| 0 | 10 | 90 |
| 2.5 | 75 | 25 |
| 5.0 | 95 | 5 |
| 7.5 | 95 | 5 |
| 7.6 | 10 | 90 |
| 10 | 10 | 90 |

2. MS: Micromass QZ, TIC: 100~900 m/z, Ion Source: ES, Capillary: 3 kV, Cone: 3V, Extractor: 3V, Drying gas flow: 600 L/hr, cone: 50 L/hr, Desolvation temperature: 300° C., Source temperature: 100° C.
3. Sample preparation: samples were dissolved in methanol at 1~10 µg/mL, then filtered through a 0.22 µm filter membrane. Injection volume: 1~10 µL.

LC-MS (Agilent, P-2) (Positive Ion Mode) or LC-MS (Agilent, N-2) (Negative Ion Mode):
1. LC: Agilent Technologies 1200 series, Binary Pump, Diode Array Detector. Xbridge-C18, 2.5 µm, 2.1×30 mm column. Mobile phase: B (MeOH) and A (0.07% HCOOH aqueous solution). Flow Rate: 0.5 mL/min at 30° C. Detector: 214 nm, 254 nm. Gradient stop time, 5 min. Timetable:

| T (min) | B (%) | A (%) |
|---|---|---|
| 0 | 80 | 20 |
| 0.2 | 80 | 20 |
| 0.8 | 5 | 95 |
| 2.8 | 5 | 95 |
| 3 | 80 | 20 |
| 5 | 80 | 20 |

2. MS: G6110A, Quadrupole LC/MS, Ion Source: ES-API, TIC: 50~900 m/z, Fragmentor: 60, Drying gas flow: 10 L/min, Nebulizer pressure: 35 psi, Drying gas temperature: 350° C., Vcap: 3500V.
3. Sample preparation: samples were dissolved in methanol at 1~10 µg/mL, then filtered through a 0.22 µm filter membrane. Injection volume: 1~10 µL.

LC-MS (Agilent, P-1) (Positive Ion Mode) or LC-MS (Agilent, N-1) (Negative Ion Mode) (Low Polarity Samples):
1. LC: Agilent Technologies 1200 series, Binary Pump, Diode Array Detector. Xbridge-C18, 2.5 µm, 2.1×30 mm column. Mobile phase: B (MeOH) and A (0.07% HCOOH aqueous solution). Flow Rate: 0.4 mL/min at 30° C. Detector: 214 nm, 254 nm. Gradient stop time, 6 min. Timetable:

| T (min) | B (%) | A (%) |
|---|---|---|
| 0 | 80 | 20 |
| 0.2 | 80 | 20 |
| 0.8 | 5 | 95 |
| 3.8 | 5 | 95 |
| 4 | 80 | 20 |
| 6 | 80 | 20 |

2. MS: G6110A, Quadrupole LC/MS, Ion Source: ES-API, TIC: 50~900 m/z, Fragmentor: 60, Drying gas flow: 10 L/min, Nebulizer pressure: 35 psi, Drying gas temperature: 350° C., Vcap: 3500V.
3. Sample preparation: samples were dissolved in methanol at 1~10 µg/mL, then filtered through a 0.22 µm filter membrane. Injection volume: 1~10 µL.

Analytical HPLC:
1. (Referred to as "Agilent") Agilent Technologies 1200 series, Quaternary Pump, Diode Array Detector. Ultimate AQ-C18, 5 µm, 4.6×250 mm column. Mobile Phase: B (MeOH) and A (0.07% TFA aqueous solution). Flow Rate: 1.00 mL/min at 30° C. Detector: 214 nm, 254 nm. Gradient stop time: 20 min. Timetable:

| T (min) | B (%) | A (%) |
| --- | --- | --- |
| 0 | 40 | 60 |
| 3 | 40 | 60 |
| 5 | 60 | 40 |
| 7 | 80 | 20 |
| 8 | 95 | 5 |
| 15 | 95 | 5 |
| 17 | 40 | 60 |
| 20 | 40 | 60 |

2. Sample preparation: samples were dissolved in methanol at ~1 mg/mL, then filtered through a 0.22 μm filter membrane. Injection volume: 1~10 μL.

Referred to as "JULY-L" or "SYN-001"

1. Agilent Technologies 1200 series, Quaternary Pump, Diode Array Detector. Waters Nova-pak C18, 4 μm, 3.9×150 mm column. Mobile Phase: C (MeOH) and D (0.07% TFA aqueous solution). Flow Rate: 1.00 mL/min at 30° C. Detector: 214 nm, 254 nm. Gradient stop time: 15 min. Timetables:

| Method name: SYN-001 (high polarity) | | |
| --- | --- | --- |
| T (min) | C (%) | D (%) |
| 0 | 5 | 95 |
| 2 | 5 | 95 |
| 5 | 12 | 88 |
| 6 | 40 | 60 |
| 7 | 95 | 5 |
| 10 | 95 | 5 |
| 12 | 60 | 40 |
| 13 | 5 | 95 |
| 15 | 5 | 95 |

| Method name: JULY-L (average and low polarity) | | |
| --- | --- | --- |
| T (min) | C (%) | D (%) |
| 0 | 20 | 80 |
| 2 | 20 | 80 |
| 4 | 40 | 60 |
| 5 | 70 | 30 |
| 6 | 95 | 5 |
| 10 | 95 | 5 |
| 11 | 70 | 20 |
| 12 | 20 | 80 |
| 15 | 20 | 80 |

2. Sample preparation: samples were dissolved in methanol at ~1 mg/mL, then filtered through a 0.22 μm filter membrane. Injection volume: 1~10 μL.

Referred to as "ZSJ-2"

1. Agilent Technologies 1200 series, Quaternary Pump, Diode Array Detector. Waters Nova-pak C18, 4 μm, 3.9×150 mm column. Mobile Phase: C (MeOH) and D (0.07% TFA aqueous solution). Flow Rate: 1.00 mL/min at 30° C. Detector: 214 nm, 254 nm. Gradient stop time: 30 min. Timetable:

| Method name: ZSJ-2 | | |
| --- | --- | --- |
| T (min) | C (%) | D (%) |
| 0 | 20 | 80 |
| 28 | 95 | 5 |
| 30 | 70 | 30 |

2. Sample preparation: samples were dissolved in methanol at ~1 mg/mL, then filtered through a 0.22 μm filter membrane. Injection volume: 1~10 μL.

Example 1: Compound 1 (S)-5-benzyl-2-(2,2-diphenylacetyl)-2,3,4,5-tetrahydro-1H-pyrido[3,4-b]indole-3-carboxylic acid 1. Procedure for the Preparation of Compound 1b

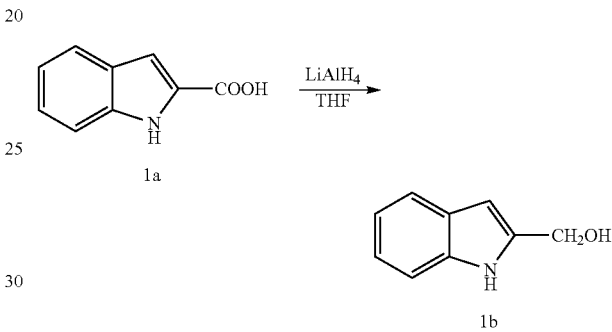

To a stirred suspension of LiAlH$_4$ (0.25 g, 6.5 mmol) in anhydrous THF (10 mL) was added compound 1a (1.0 g, 6.2 mmol) slowly at 0° C. After addition, the mixture was stirred at 25° C. overnight and then heated at reflux for two hours, TLC (MeOH:DCM=1:10) showed the starting material was consumed. The mixture was cooled to −5° C., acidified with a 1 M aqueous HCl solution to pH 3~4 and extracted with EA (10 mL×2). The combined organic layers were washed with brine (10 mL×2), dried over Na$_2$SO$_4$, filtered and concentrated in vacuo to give 1b (0.8 g, 88%) as an off-white solid. LC-MS (Agilent): R$_t$ 4.38 min; m/z calculated for C$_9$H$_9$NO [M+H]$^+$ 148.1, [M+Na]$^+$ 170.1. found [M+H]$^+$ 148.1, [M+Na]$^+$ 170.1.

2. Procedure for the Preparation of Compound 1c

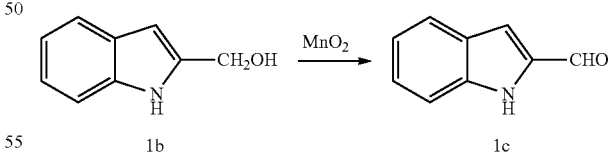

To a stirred solution of compound 1b (0.4 g, 2.7 mmol) in CHCl$_3$ (10 mL) was added MnO$_2$ (0.95 g, 10.9 mmol) slowly at 0° C. After addition, the mixture was heated at reflux overnight, TLC (MeOH:DCM=1:10) showed the starting material was consumed. The mixture was cooled to RT, filtered and the filtrate was concentrated in vacuo. Purification by chromatography (PE:EA=10:1) gave 1c (0.25 g, 62%) as an off-white solid. LC-MS (Agilent): R$_t$ 4.59 min; m/z calculated for C$_9$H$_7$NO [M+H]$^+$ 146.1, [M+Na]$^+$ 168.1. found [M+H]$^+$ 146.1, [M+Na]$^+$ 168.0.

3. Procedure for the Preparation of Compound 1d

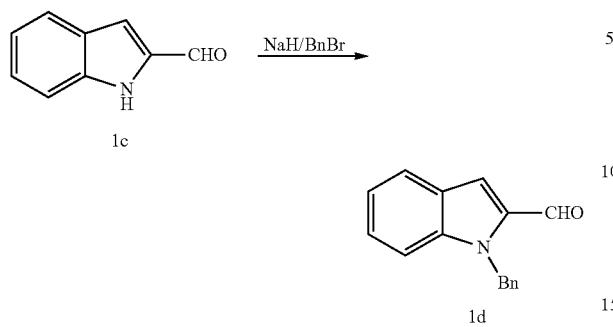

To a stirred solution of compound 1c (1.0 g, 6.9 mmol) in anhydrous DMF (10 mL) was added NaH (60% w/w dispersion in mineral oil, 0.3 g, 7.6 mmol) slowly at 0° C. After addition, the mixture was stirred at 0° C. for 0.5 h, BnBr (1.3 g, 7.6 mmol) was added and stirring was continued at 0° C. for 10 min. TLC (EA:PE=1:10) showed the starting material was consumed. The reaction was quenched with cold water (50 mL) and extracted with EA (20 mL×2). The combined organic layers were washed with brine (20 mL×2), dried over $Na_2SO_4$, filtered and concentrated in vacuo. The residue was purified by chromatography (PE:EA=20:1) to give 1d (1.3 g, 80%) as an off-white solid. LC-MS (Agilent): $R_t$ 5.15 min; m/z calculated for $C_{16}H_{13}NO$ $[M+Na]^+$ 258.1. found $[M+Na]^+$ 258.1.

4. Procedure for the Preparation of Compound 1f

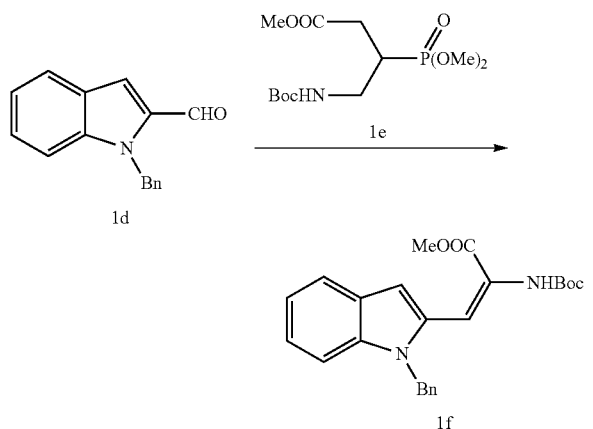

To a stirred solution of compound 1d (1.0 g, 4.25 mmol) and the phosphonate 1e (1.33 g, 4.47 mmol) in anhydrous THF (10 mL) was added tetramethylguanidine (0.59 g, 5.1 mmol) slowly at 0° C. The mixture was then stirred at RT overnight, TLC (EA:PE=1:4) showed the starting material was consumed. The reaction was quenched with cold water (20 mL) and extracted with EA (20 mL×2). The combined organic layers were washed with brine (20 mL×2), dried over $Na_2SO_4$, filtered and concentrated in vacuo. The residue was purified by chromatography (PE:EA=20:1) to give 1f (1.5 g, 86%) as an off-white solid. LC-MS (Agilent): $R_t$ 5.23 min; m/z calculated for $C_{24}H_{26}N_2O_4$ $[M+H]^+$ 407.2, $[M+Na]^+$ 429.2. found $[M+H]^+$ 407.2, $[M+Na]^+$ 429.1.

5. Procedure for the Preparation of Compound 1g

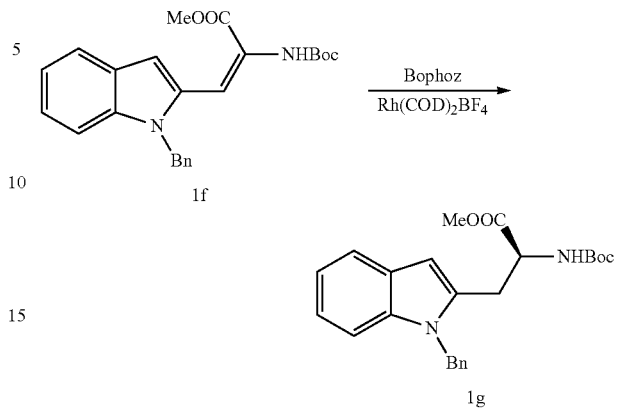

A mixture of Bophoz™ (23 mg, 0.038 mmol) and $Rh(COD)_2BF_4$ (15 mg, 0.037 mmol) in MeOH (15 mL) was stirred for 15 min under $N_2$ atmosphere until a clear solution was obtained. Compound 1f (1.0 g, 2.46 mmol) was then added and the mixture was purged with $H_2$ (×3) and then stirred under a $H_2$ atmosphere (50 psi) at RT for 14 h. TLC (EA:PE=1:4) showed most of the starting material was consumed. The mixture was concentrated in vacuo and the residue was purified by chromatography (PE:EA=20:1) to give 1 g (0.6 g, 60%) as an off-white solid. LC-MS (Agilent): $R_t$ 5.29 min; m/z calculated for $C_{24}H_{28}N_2O_4$ $[M+H]^+$ 409.2, $[M+Na]^+$ 431.2. found $[M+H]^+$ 409.2, $[M+Na]^+$ 431.1.

6. Procedure for the Preparation of Compound 1h

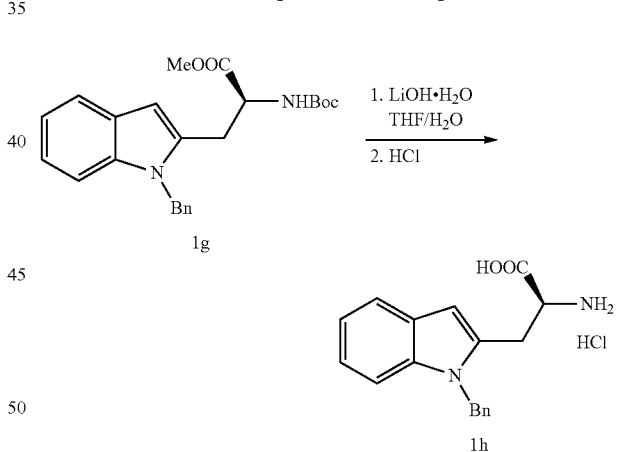

To a stirred solution of Compound 1g (600 mg, 1.47 mmol) in THF (10 mL) was added a solution of $LiOH \cdot H_2O$ (123 mg, 2.94 mmol) in water (4 mL) at 0° C. After addition, the mixture was stirred at RT for 5 h, TLC (EA:PE=1:10) showed the starting material was consumed. The mixture was cooled to 0° C. and acidified with 1 M HCl to pH 3~4. The mixture was extracted with EA (5 mL×2) and the organic phase was washed with brine (5 mL), dried over $Na_2SO_4$ and concentrated in vacuo. The residue was used directly in the next step. 4 M HCl/diox (10 mL) was added to the residue and the resulting solution was stirred at RT overnight, TLC (MeOH:DCM=1:10+1 drop AcOH) showed the reaction was complete. The mixture was evaporated to dryness to give 1h (0.45 g, 93%) as an off-white solid.

LC-MS (Agilent): $R_t$ 4.69 min; m/z calculated for $C_{18}H_{18}N_2O_2$ [M+H]$^+$ 295.1, [M+Na]$^+$ 371.1. found [M+H]$^+$ 295.1, [M+Na]$^+$ 317.1.

7. Procedure for the Preparation of Compound 1i

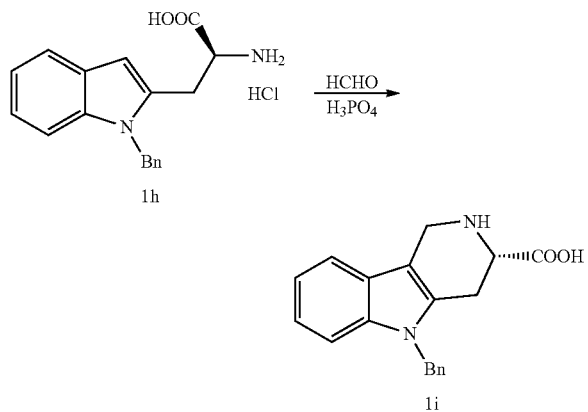

To a stirred suspension of compound 1h (400 mg, 1.36 mmol) in water (6 mL) was added paraformaldehyde (170 mg, 2.04 mmol) and $H_3PO_4$ (251 mg, 2.18 mmol) at RT. After addition, the mixture was stirred at 60° C. overnight, TLC (MeOH:DCM=1:10) showed the starting material was consumed. The mixture was cooled to RT, basified with aq. NaOAc to pH 3~4 and filtered to collect the product. The product was washed with cold water (1 mL×2) and dried to give 1i (350 mg, 83%) as an off-white solid. LC-MS (Agilent): $R_t$ 3.44 min; m/z calculated for $C_{19}H_{18}N_2O_2$ [M+H]$^+$ 307.1. found [M+H]$^+$ 307.1.

8. Procedure for the Preparation of Compound 1

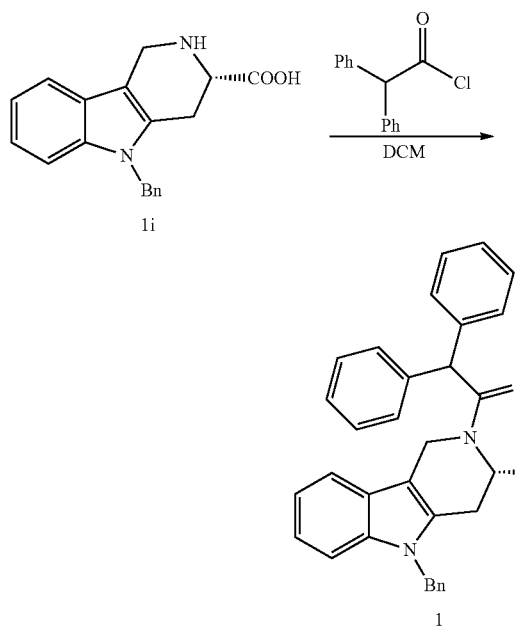

To a stirred solution of compound 1i (40 mg, 0.13 mmol) and $Et_3N$ (27 mg, 0.26 mmol) in DCM (4 mL) was added diphenylacetyl chloride (45 mg, 0.20 mmol) at 0° C. After addition, the mixture was warmed slowly to RT and stirred for 10 min, TLC (MeOH:DCM=1:10) showed the starting material was consumed. The reaction was repeated on a larger batch of compound 1i (150 mg, 0.49 mmol) and the two reaction mixtures were combined and diluted with water (20 mL). The organic layer was separated and washed with brine (3×10 mL), dried over $Na_2SO_4$ then filtered and concentrated in vacuo. The residue was purified by chromatography (DCM:EA=20:1 to 10:1) to give 1 (150 mg, 48%) as a pale yellow solid. LC-MS (Agilent): $R_t$ 3.77 min; m/z calculated for $C_{33}H_{28}N_2O_3$ [M+H]$^+$ 501.2. found [M+H]$^+$ 501.2. HPLC (214 and 254 nm): $R_t$ 14.08 min.

Example 2: Compound 9 (S)-3-(2,2-diphenylacetyl)-1,2,3,4-tetrahydrobenzo[5,6][1,4]dioxino[2,3-f]isoquinoline-2-carboxylic acid 1. Procedure for the Preparation of Compound 9c Compound 9c was prepared according to *J. Chem. Soc.* (Perkin 1) 1990, 1071.

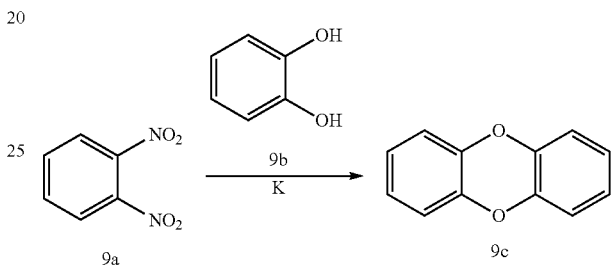

To a stirred suspension of 9b (5.9 g, 53.6 mmol) in anhydrous HMPA (60 mL) was added potassium metal (3.8 g, 96.5 mmol) slowly at 20° C. under a $N_2$ atmosphere. When all the potassium metal dissolved, compound 9a (4.5 g, 26.8 mmol) was added and the mixture was heated at 110° C. for 4 h, TLC (EA:PE=1:4) showed compound 9a was completely consumed. The mixture was cooled to 0° C., quenched with cold water (300 mL) and extracted with EA (50 mL×2). The combined organic extracts were washed with brine (50 mL×2), dried over $Na_2SO_4$, filtered and concentrated in vacuo. The residue was purified by chromatography (PE) to give 9c (2.0 g, 41%) as an off-white solid.

2. Procedure for the Preparation of Compound 9d

Compound 9d was prepared according to *J. Org. Chem.* 1990, 55, 438.

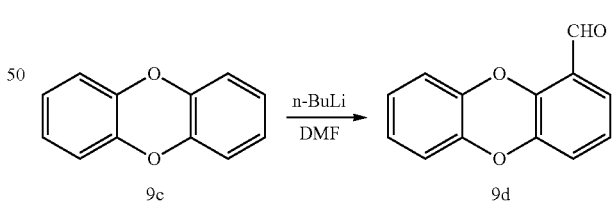

To a stirred solution of compound 9c (1.4 g, 7.6 mmol) in anhydrous $Et_2O$ (30 mL) was added n-BuLi (3.7 mL, 9.1 mmol) slowly at RT. After addition, the mixture was stirred at RT for 1 h. DMF (0.84 g, 11.4 mmol) was added to the mixture and stirring was continued at RT for 10 min, TLC (PE:EA=20:1) showed the starting material was consumed. The reaction was quenched with cold water (30 mL) at 0° C. The organic layer was separated, washed with brine (15 mL×2), dried over $Na_2SO_4$, filtered and concentrated in vacuo. The residue was purified by chromatography (PE) to give 9d (1.1 g, 68%) as an off-white solid. LC-MS (Agilent):

$R_t$ 5.16 min; m/z calculated for $C_{13}H_8O_3$ [M+H]$^+$ 213.1, [M+Na]$^+$ 235.0. found [M+H]$^+$ 213.0, [M+Na]$^+$ 235.0.

3. Procedure for the Preparation of Compound 9f

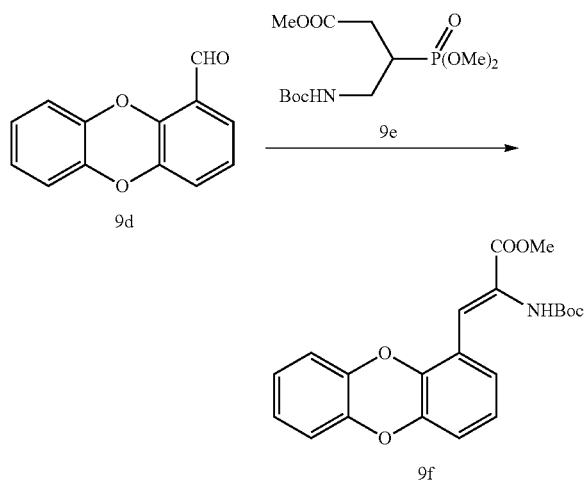

To a stirred solution of compound 9d (1.3 g, 6.13 mmol) and the phosphonate 9e (1.93 g, 6.43 mmol) in anhydrous THF (20 mL) was added tetramethylguanidine (0.85 g, 7.36 mmol) slowly at 0° C. and the mixture was stirred overnight at RT, TLC (EA:PE=1:4) showed the starting material was consumed. The reaction was quenched with cold water (30 mL) at 0° C. and extracted with EA (20 mL×2). The combined organic extracts were washed with brine (20 mL×2), dried over $Na_2SO_4$, filtered and concentrated in vacuo. The residue was purified by chromatography (PE:EA=10:1) to give 9f (1.5 g, 64%) as an off-white solid. LC-MS (Waters): $R_t$ 6.67 min; m/z calculated for $C_{21}H_{21}NO_6$ [M-Boc+H]$^+$ 284.1, [M+Na]$^+$ 406.1. found [M-Boc+H]$^+$ 284.0, [M+Na]$^+$ 405.9.

4. Procedure for the Preparation of Compound 9g

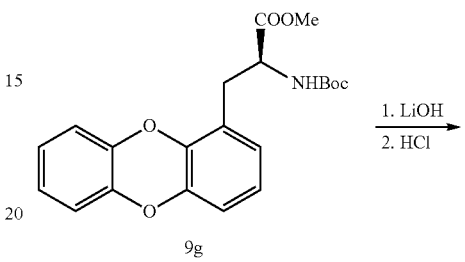

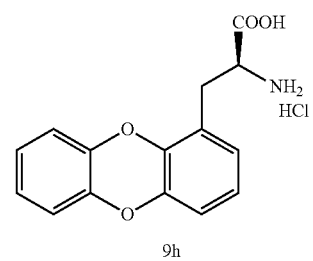

A mixture of Bophoz™ (41 mg, 0.067 mmol) and Rh(COD)$_2$BF$_4$ (23 mg, 0.064 mmol) in MeOH (25 mL) was stirred for 15 min under $N_2$ atmosphere until a clear solution was obtained. Compound 9f (1.7 g, 4.43 mmol) was added and the mixture was purged with $H_2$ (×3). The mixture was then stirred under a $H_2$ atmosphere (50 psi) at RT for 40 h, TLC (EA:PE=1:4) showed most of the starting material was consumed. The mixture was concentrated in vacuo and the residue was purified by chromatography (PE:EA=10:1) to give 9g (1.5 g, 88%) as an off-white solid. LC-MS (Agilent): $R_t$ 3.88 min; m/z calculated for $C_{21}H_{23}NO_6$ [M-Boc+H]$^+$ 286.1, [M+Na]$^+$ 408.1. found [M-Boc+H]$^+$ 286.1, [M+Na]$^+$ 408.1.

5. Procedure for the Preparation of Compound 9h

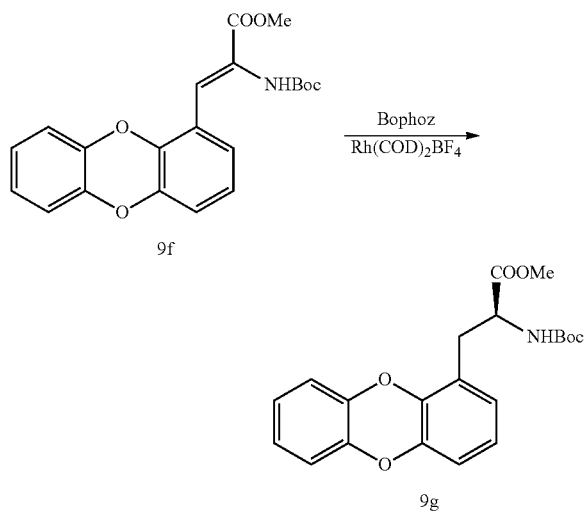

To a stirred solution of compound 9g (1.5 g, 3.89 mmol) in THF (15 mL) was added a solution of LiOH (330 mg, 7.78 mmol) in water (4 mL) at 0° C. and the mixture was stirred at RT for 5 h, TLC (EA:PE=1:10) showed the starting material was consumed. The mixture was concentrated in vacuo, the residue was partitioned between EA/water (10 mL/5 mL) and the aqueous layer was acidified with 1 M HCl to pH 3~4. The organic layer was separated, washed with brine (5 mL×2), dried over $Na_2SO_4$, filtered and concentrated in vacuo. 4 M HCl/dioxane (10 mL) was added to the residue and the mixture was stirred at RT overnight, TLC (MeOH:DCM=1:10) showed the reaction was complete. The mixture was concentrated in vacuo to give 9h (0.95 g, 80%) as an off-white solid. LC-MS (Agilent): $R_t$ 3.88 min; m/z calculated for $C_{15}H_{13}NO_4$ [M+H]$^+$ 272.1. found [M+H]$^+$ 272.1.

6. Procedure for the Preparation of Compound 9i

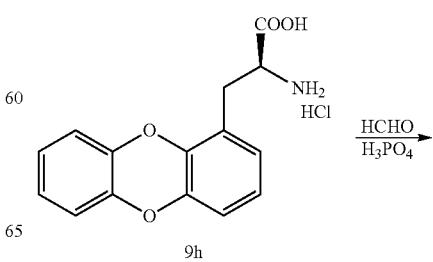

-continued

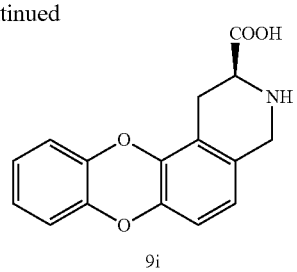

9i

To a stirred suspension of compound 9h (500 mg, 1.63 mmol) in water (8 mL) was added paraformaldehyde (200 mg, 2.44 mmol) and $H_3PO_4$ (300 mg, 2.61 mmol) at RT and the mixture was heated at 60° C. overnight, TLC (MeOH:DCM=1:10) showed the starting material was consumed. The mixture was cooled to RT, basified with aqueous NaOAc to pH 3~4 and the product was collected by filtration, washed with cold water (1 mL×2) and dried to give 9i (380 mg, 82%) as a white solid. LC-MS (Agilent): $R_t$ 3.00 min; m/z calculated for $C_{16}H_{13}NO_4$ [M+H]+ 284.1. found [M+H]+ 284.1.

7. Procedure for the Preparation of Compound 9

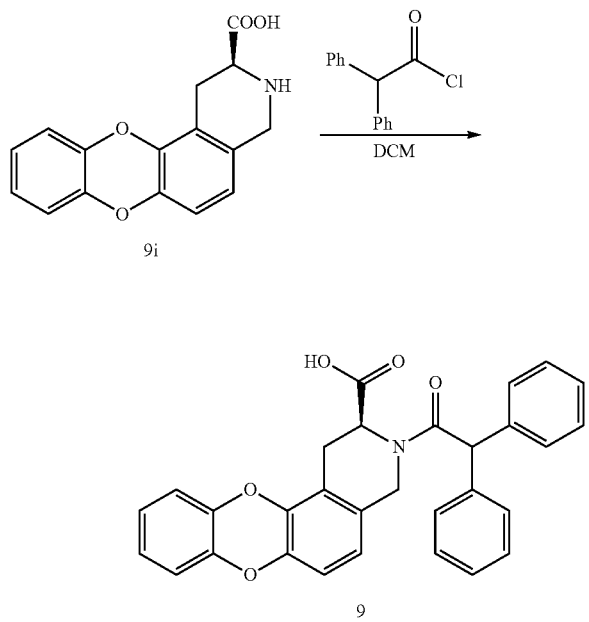

To a stirred solution of compound 9i (40 mg, 0.14 mmol) and $Et_3N$ (28 mg, 0.28 mmol) in DCM (4 mL) was added diphenylacetyl chloride (48 mg, 0.21 mmol) at 0° C. The mixture was then warmed slowly to RT and stirred for 10 min, TLC (MeOH:DCM=1:10) showed the starting material was consumed. The reaction was repeated on a larger batch of compound 9i (200 mg, 0.71 mmol) and the reaction mixtures were combined and diluted with water. The organic layer was separated, washed with brine, dried over $Na_2SO_4$, filtered and concentrated in vacuo. The residue was purified by chromatography (DCM:EA=20:1 to 10:1) to give 9 (100 mg, 45%) as an off-white solid. LC-MS (Agilent): $R_t$ 3.60 min; m/z calculated for $C_{30}H_{23}NO_5$ [M+H]+ 478.2, [M+Na]+ 500.1. found [M+H]+ 478.1, [M+Na]+ 500.1. HPLC (214 and 254 nm): $R_t$ 14.27 min.

Example 3: Compound 26 (2S)-4-(benzyloxy)-1-(2,2-diphenylacetyl)piperidine-2-carboxylic acid 1. Procedure for the Preparation of Compound 26b

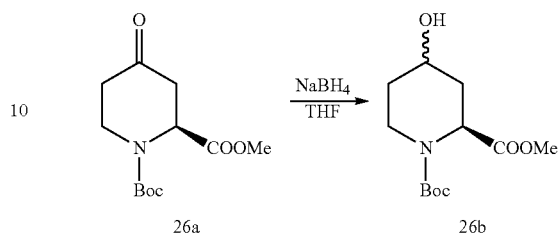

Ketopiperidine 26a was made according to *Tetrahedron*, 1997, 53(46), 15671-15680. To a stirred solution of compound 26a (500 mg, 1.93 mmol) in THF (10 mL) at 0° C. was added $NaBH_4$ (80 mg, 2.13 mmol) and the mixture was stirred at 0° C. for 1 h, TLC (PE:EA=4:1) showed the reaction was complete. The reaction was quenched with a saturated aqueous $NH_4Cl$ solution (10 mL) followed by a 0.5 M aqueous HCl solution (5 mL) and extracted with EA (20 mL×2). The combined organic extracts were washed with brine, dried over $Na_2SO_4$, filtered and concentrated in vacuo to give 26b (450 mg, 90%) as a colorless oil, which was used directly in next step.

2. Procedure for the Preparation of Compound 26c

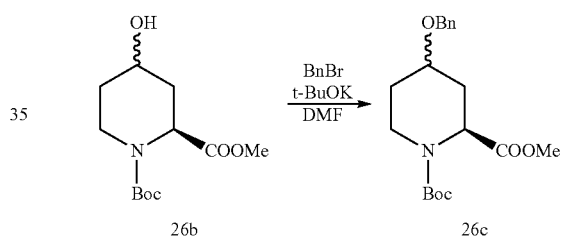

A stirred solution of compound 26b (440 mg, 1.69 mmol) and BnBr (347 mg, 2.03 mmol) in DMF (10 mL) was cooled to −30° C. under a $N_2$ atmosphere. t-BuO-K+ (225 mg, 1.09 mmol) was added in portions and the mixture was then allowed to warm slowly to RT and stirred overnight. Water (20 mL) was added followed by a 0.5 M aqueous HCl solution (10 mL) and the mixture was extracted with EA (30 mL×2). The combined organic extracts were washed with brine, dried over $Na_2SO_4$, filtered and concentrated in vacuo. The residue was purified by chromatography (PE:EtOAc=1:0 to 10:1) to give 26c (100 mg, 17%) as a viscous colorless oil.

3. Procedure for the Preparation of Compound 26d

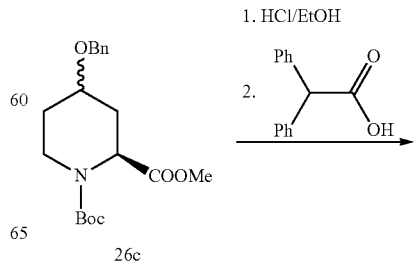

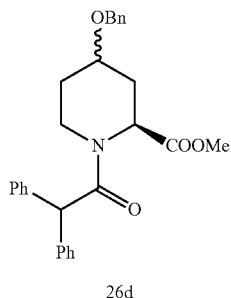

26d

To a stirred solution of compound 26c (200 mg, 0.57 mmol) in MeOH (2 mL) was added a 4 M HCl/EtOH solution (10 mL) and the mixture was stirred at RT for 7 hours, TLC (PE:EA=4:1) showed the reaction was complete. The mixture was concentrated in vacuo and the residue was partitioned between DCM (20 mL) and water (20 mL). The aqueous layer was basified to pH 7-8 with a saturated aqueous $K_2CO_3$ solution and the organic layer was separated, washed with brine (20 mL×1), dried over $Na_2SO_4$, filtered and concentrated in vacuo. The residue was dissolved in DCM (10 mL), diphenyl acetic acid (131 mg, 0.61 mmol), EDCI.HCl (128 mg, 0.67 mmol) and a catalytic amount of DMAP were added. The mixture was then stirred at RT overnight, TLC (DCM:MeOH=10:1) showed the reaction was complete. The mixture was washed with water (20 mL) and the aqueous layer was extracted with DCM (20 mL×2). The combined organic extracts were washed with brine, dried over $Na_2SO_4$, filtered and concentrated in vacuo. The residue was purified by chromatography (PE:EA=100:1 to 10:1) to give 26d (170 mg, 67%) as a colorless oil. LC-MS (Agilent): $R_t$ 3.52 min; m/z calculated for $C_{28}H_{29}NO_4$ [M+H]$^+$ 444.2. found [M+H]$^+$ 444.2.

4. Procedure for the Preparation of Compound 26

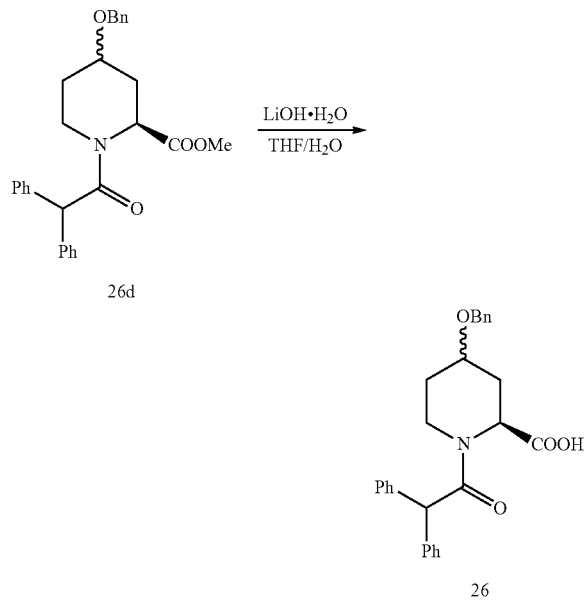

To a mixture of compound 26d (160 mg, 0.36 mmol) in THF/water (10 mL/3 mL) was added LiOH.H$_2$O (15 mg, 0.72 mmol) and the mixture was stirred at RT overnight, TLC (PE:EA=4:1) showed that the starting material was consumed. Most of the THF was removed in vacuo and the residue was dissolved in water (20 mL) and washed with hexane (20 mL). The aqueous layer was cooled to 0° C. and acidified to pH 4 with a 1 M aqueous HCl solution. The resulting precipitate was collected by filtration, washed with water and dried at 45° C. overnight to give 26 (105 mg, 68%) as a white solid. Analytical HPLC analysis revealed a ~9:1 mixture of trans/cis isomers 29 and 30. LC-MS (Agilent): $R_t$ 3.43 min; m/z calculated for $C_{27}H_{27}NO_4$ [M+H]$^+$ 430.2. found [M+H]$^+$ 430.2. HPLC (214 and 254 nm): $R_t$ 8.26 min. HPLC (ZSJ-2) (214 nm) $R_t$ 20.97 min (major) and 21.38 min (minor).

Example 4: Compound 30 (2S,4R)-4-benzyloxy-1-(2,2-diphenylacetyl)piperidine-2-carboxylic acid (major isomer)

1. Procedure for the Preparation of 30b

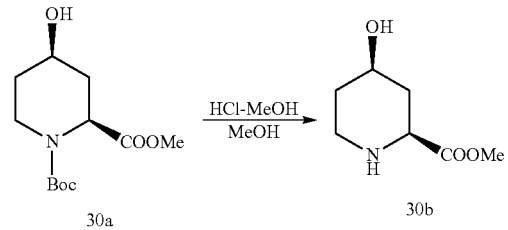 [SMILES: "MeOH" ; COC(=O)[C@@H]1C[C@H](O)CCN1C(=O)OC(C)(C)C ; COC(=O)[C@@H]1C[C@H](O)CCN1 ; "HCl-MeOH"]

To a solution of 30a (1.00 g, 3.86 mmol) in MeOH (5 mL) was added a 4 M HCl/MeOH solution (10 mL) and the mixture was stirred at RT overnight, TLC (PE:EA=2:1) showed the starting material was consumed completely. The mixture was concentrated in vacuo to give 30b (730 mg) as grey solid, which was used directly in the next step without purification. LC-MS (Agilent): $R_t$ 0.70 min; m/z calculated for $C_7H_{13}NO_3$ [M+Na]$^+$ 182.1. found [M+H]$^+$ 182.1.

2. Procedure for the Preparation of 30c

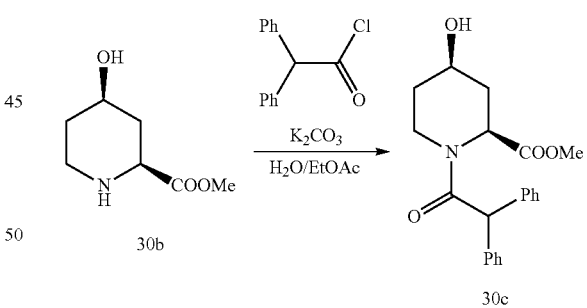

To a mixture of 30b (0.73 g, 3.86 mmol) and $K_2CO_3$ (0.9 g, 6.56 mmol) in water/EA (10 mL/10 mL) at to 0° C. was added a solution of diphenylacetyl chloride (1.07 g, 4.63 mmol) in EA (10 mL) and the mixture was stirred at RT for 1.5 h, TLC (PE:EA=2:1) showed that a major new product was formed. The layers were separated and the aqueous layer was extracted with EA (15 mL). The combined organic extracts were washed with brine (20 mL), dried over $Na_2SO_4$, filtered and concentrated in vacuo. The residue was purified by chromatography (PE:EA=1:0 to 2:1) to give 30c (830 mg, 60%) as a white solid. LC-MS (Agilent): $R_t$ 4.07 min; m/z calculated for $C_{21}H_{23}NO_4$ [M+H]$^+$ 354.2, [M+Na]$^+$ 376.2. found [M+H]$^+$ 354.2, [M+Na]$^+$ 376.2.

3. Procedure for the Preparation of 30d

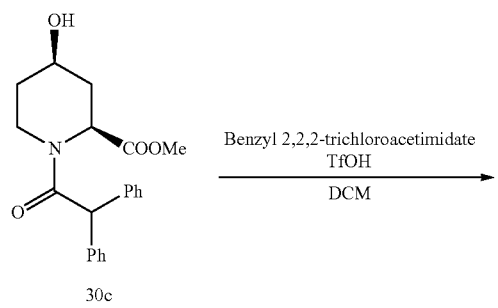

To a solution of 30c (220 mg, 0.62 mmol) and benzyl 2,2,2-trichloroacetimidate (234 mg, 0.95 mmol) in DCM (15 mL) was added TfOH (2 drops) and the mixture was stirred at RT overnight, TLC (PE:EA=2:1) showed that most of the starting material was consumed. The mixture was washed with brine (10 mL×2), dried over Na$_2$SO$_4$, filtered and concentrated in vacuo. The residue was purified by chromatography (PE:EA=1:0 to 4:1) to give 30d (130 mg, 47%) as a colorless oil. LC-MS (Agilent): R$_t$ 4.46 min; m/z calculated for C$_{28}$H$_{29}$NO$_4$ [M+H]$^+$ 444.2, [M+Na]$^+$ 466.2. found [M+H]$^+$ 444.2, [M+Na]$^+$ 466.2.

4. Procedure for the Preparation of 30

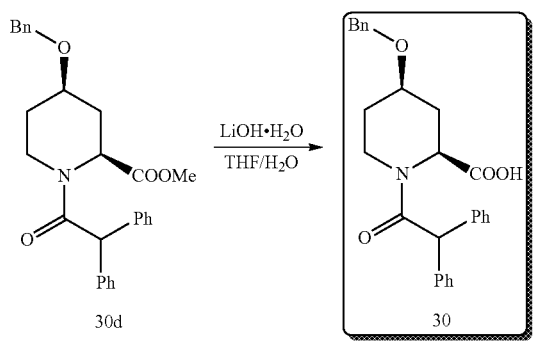

A mixture of 30d (130 mg, 0.29 mmol) and LiOH·H$_2$O (37 mg, 0.88 mmol) in THF/water (8 mL/2 mL) was stirred at RT overnight, TLC (PE:EA=1:1) showed that the starting material was consumed. Most of the THF was removed in vacuo and the residue was dissolved in water (15 mL), acidified to pH 4~5 with a 3 M aqueous HCl solution and extracted with EA (10 mL×2). The combined organic extracts were washed with brine, dried over Na$_2$SO$_4$, filtered and concentrated in vacuo. The residue was purified by preparative HPLC to give the product (70 mg, 56%) as a white solid. Analytical HPLC analysis revealed a ~7:3 mixture of cis/trans isomers 30 and 29. LC-MS (Agilent): R$_t$ 4.17 min; m/z calculated for C$_{27}$H$_{27}$NO$_4$ [M+H]$^+$ 430.2, [M+Na]$^+$ 452.2. found [M+H]$^+$ 430.2, [M+Na]$^+$ 452.2. HPLC (JULY-L) (214 and 254 nm): R$_t$ 9.21 min. HPLC (ZSJ-2) (214 nm): R$_t$ 20.97 min (minor) and 21.37 min (major).

Example 5: Compound 31 (2S,4R)-1-(2,2-diphenylacetyl)-4-(methyl(phenylpropyl)amino)piperidine-2-carboxylic acid 1. Procedure for the Preparation of 31b

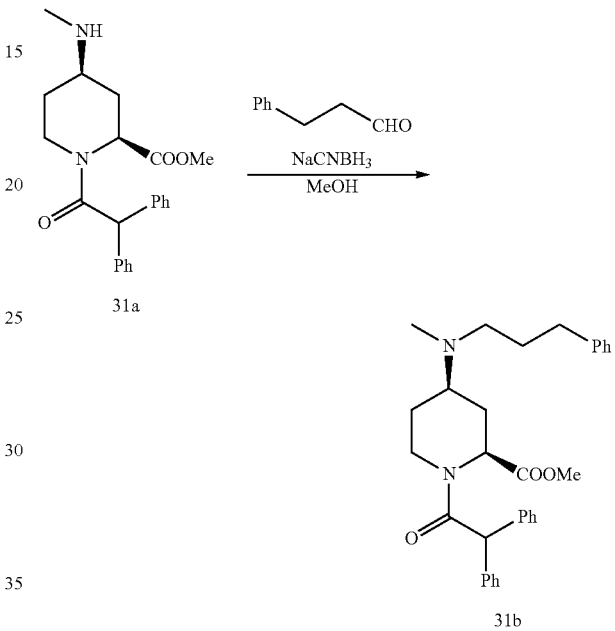

To a stirred solution of 31a (100 mg, 0.27 mmol) and 3-phenylpropanal (55 mg, 0.40 mmol) in MeOH (10 mL) was added 1 drop of AcOH and the mixture was stirred at RT for 1 h. NaCNBH$_3$ (25 mg, 0.40 mmol) was added and stirring was continued at RT overnight, TLC (DCM: MeOH=20:1) showed that the starting material was consumed. Most of the MeOH was removed in vacuo and the residue was dissolved in water (20 mL) and extracted with EA (15 mL×2). The combined organic extracts were washed with brine, dried over Na$_2$SO$_4$, filtered and concentrated in vacuo. The residue was purified by chromatography (DCM: MeOH=150:1 to 50:1) to give 31b (80 mg, 61%) as a yellow oil. LC-MS (Agilent): R$_t$ 3.75 min; m/z calculated for C$_{31}$H$_{36}$N$_2$O$_3$ [M+H]$^+$ 485.3. found [M+H]$^+$ 485.3.

2. Procedure for the Preparation of 31

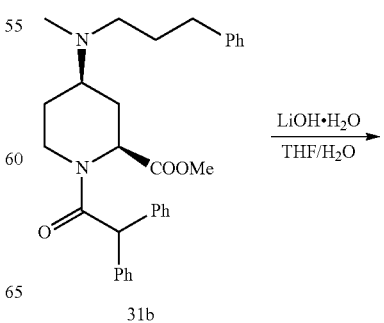

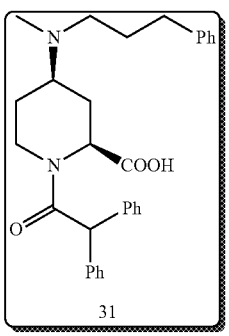

A mixture of 31b (80 mg, 0.16 mmol) and LiOH·H$_2$O (14 mg, 0.32 mmol) in THF/water (6 mL/2 mL) was stirred at RT overnight, TLC (DCM:MeOH=20:1) showed that the starting material was consumed. Most of the THF was removed in vacuo and the residue was dissolved in water (20 mL) and washed with Et$_2$O (15 mL). DCM (15 mL) was added and the aqueous layer was acidified to pH 2~3 with a 1 M aqueous HCl solution. The layers were separated and the aqueous layer was further extracted with DCM (15 mL). The combined organic extracts were washed with brine, dried over Na$_2$SO$_4$, filtered and concentrated in vacuo. The residue was purified by preparative HPLC to give 31 (35 mg, 46%) as a white solid. LC-MS (Agilent): R$_t$ 3.84 min; m/z calculated for C$_{30}$H$_{34}$N$_2$O$_3$ [M+H]$^+$ 471.3. found [M+H]$^+$ 471.3. HPLC (JULY-L) (214 and 254 nm): R$_t$ 8.83 min.

Example 6: Compound 32 (2S,4R)-4-(2,2-diphenylacetyl)-4-(methyl(3-phenylprop-2-yn-1-yl)amino)piperidine-2-carboxylic acid 1. Procedure for the Preparation of 32a

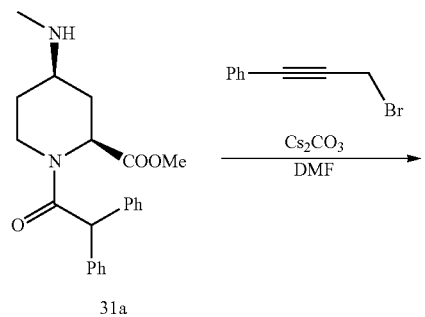

A mixture of 31a (240 mg, 0.66 mmol), 1-(3-bromoprop-1-ynyl)benzene (153 mg, 0.78 mmol) and Cs$_2$CO$_3$ (255 mg, 0.78 mmol) in DMF (15 mL) was stirred at 35° C. overnight, TLC (PE:EA=1:1) showed most of the starting material was consumed. Water (50 mL) was added and the mixture was extracted with EA (20 mL×2). The combined organic extracts were washed with brine, dried over Na$_2$SO$_4$, filtered and concentrated in vacuo. The residue was purified by chromatography (PE:EA=10:1 to 5:1) to give 32a (120 mg, 39%) as a yellow oil. LC-MS (Agilent): R$_t$ 3.97 min; m/z calculated for C$_{31}$H$_{32}$N$_2$O$_3$ [M+H]$^+$ 481.2. found [M+H]$^+$ 481.2.

2. Procedure for the Preparation of 32

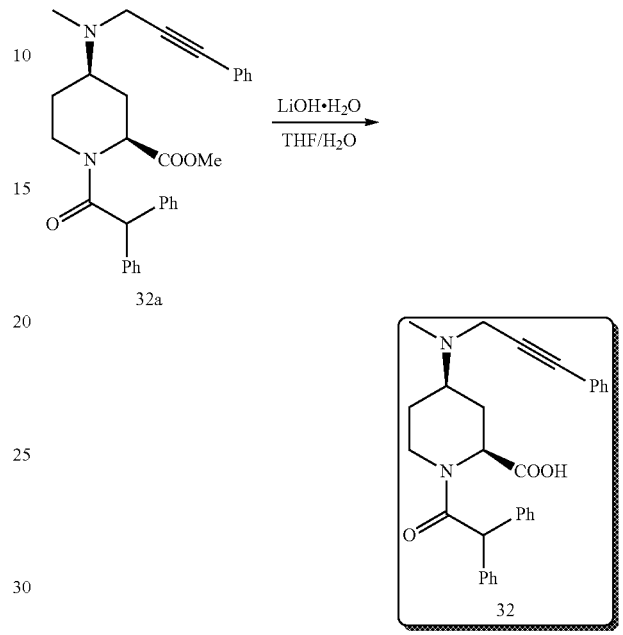

To a mixture of 32a (120 mg, 0.25 mmol) in THF/water (6 mL/2 mL) was added LiOH·H$_2$O (21 mg, 0.5 mmol) and the mixture was stirred at RT overnight, TLC (PE:EA=1:1) showed that the starting material was consumed. Most of the THF was removed in vacuo and the residue was dissolved in water (15 mL) and washed with ether (10 mL). DCM (15 mL) was added and the aqueous layer was acidified to pH 2-3 with a 1 M aqueous HCl solution. The layers were separated and the aqueous layer was further extracted with DCM (15 mL). The combined organic layers were washed with brine, dried over Na$_2$SO$_4$, filtered and concentrated in vacuo. The residue was purified by preparative HPLC to give 32 (70 mg, 60%) as a white solid. LC-MS (Agilent): R$_t$ 3.91 min; m/z calculated for C$_{30}$H$_{30}$N$_2$O$_3$ [M+H]$^+$467.2. found [M+H]$^+$ 467.2. HPLC (214 and 254 nm): R$_t$ 8.28 min.

Example 7: Compound 33 (2S,4S)-1-(2,2-diphenylacetyl)-4-(methyl(3-phenylprop-2-yn-1yl)amino)piperidine-2-carboxylic acid 1. Procedure for the Preparation of 33b

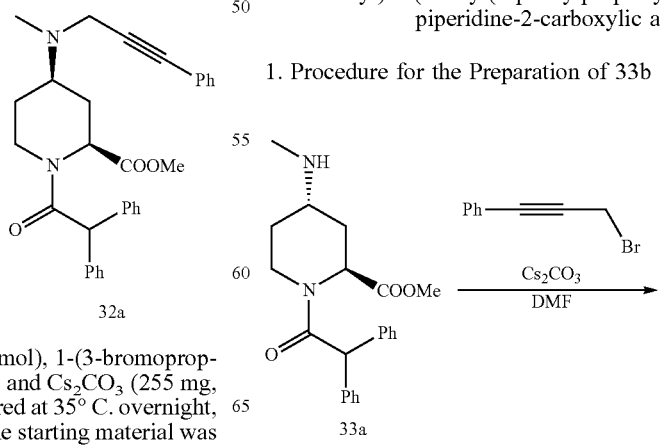

-continued

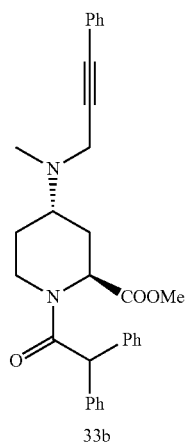

33b

A mixture of 33a (170 mg, 0.46 mmol), 1-(3-bromoprop-1-ynyl)benzene (109 mg, 0.57 mmol) and $Cs_2CO_3$ (181 mg, 0.57 mmol) in DMF (10 mL) was stirred at RT overnight, TLC (DCM:MeOH=10:1) showed that the starting material was consumed. The mixture was poured into ice-water (200 mL) and extracted with EA (30 mL×2). The combined organic extracts were washed with brine (40 mL×2), dried over $Na_2SO_4$, filtered and concentrated in vacuo. The residue was purified by chromatography (PE:EA=8:1 to 1:1) to give 33b (94 mg, 42%) as a pale yellow oil. LC-MS (Agilent): $R_t$ 4.28 min; m/z calculated for $C_{31}H_{32}N_2O_3$ $[M+H]^+$ 481.2. found $[M+H]^+$ 481.2.

2. Procedure for the Preparation of 33

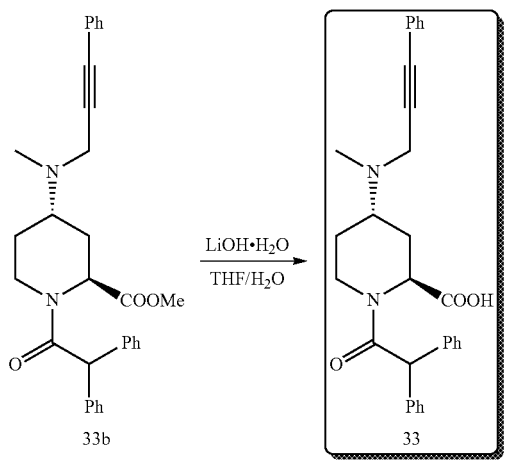

A mixture of 33b (94 mg, 0.20 mmol) and $LiOH·H_2O$ (25 mg, 0.59 mmol) in THF/water (6 mL/2 mL) was stirred at RT overnight, TLC (DCM:MeOH=10:1) showed the starting material was consumed. Most of the THF was removed in vacuo and residue was dissolved in water (10 mL) and washed with $Et_2O$ (10 mL). The aqueous layer was acidified to pH 4~5 with a 3 M aqueous HCl solution and extracted with EA (15 mL×3). The combined organic extracts were washed with brine (30 mL×2), dried over $Na_2SO_4$, filtered and concentrated in vacuo. The residue was purified by preparative HPLC to give 33 (23 mg, 57%) as a white solid. LC-MS (Agilent): $R_t$ 3.81 min; m/z calculated for $C_{30}H_{30}N_2O_3$ $[M+H]^+$ 467.2. found $[M+H]^+$ 467.2. HPLC (JULY-L) (214 and 254 nm): $R_t$ 8.74 min.

Example 8: Compound 34 (2S,4R)-1-(2,2-diphenylacetyl)-4-(methyl(3-phenethyl)amino)piperidine-2-carboxylic acid 1. Procedure for the Preparation of 31a

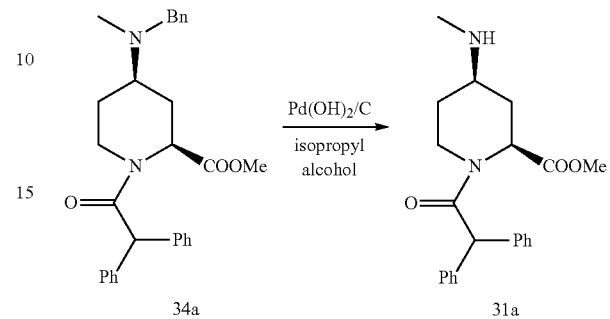

To a solution of 34a (250 mg, 0.55 mmol) in isopropanol (10 mL) was added 10% $Pd(OH)_2$/C (25 mg) and the mixture was stirred at 30° C. under a $H_2$ atmosphere (1 atm) overnight, TLC (PE:EA=1:1) showed that the starting material was consumed. The mixture was filtered and the filtrate was concentrated in vacuo to give 31a (200 mg, 99%) as a colorless oil, which was used in next step without further purification. LC-MS (Agilent): $R_t$ 3.39 min; m/z calculated for $C_{22}H_{26}N_2O_3$ $[M+H]^+$ 367.2. found $[M+H]^+$ 367.2.

2. Procedure for the Preparation of 34b

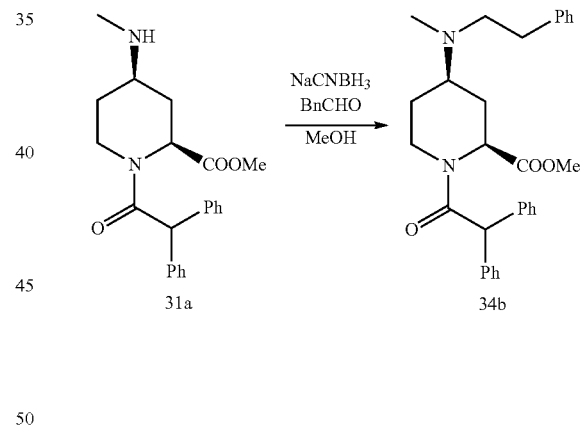

To a stirred solution of 31a (100 mg, 0.27 mmol) and phenylacetaldehyde (50 mg, 0.40 mmol) in MeOH (10 mL) was added 2 drops of AcOH and the mixture was stirred at RT for 40 min. $NaCNBH_3$ (25 mg, 0.40 mmol) was added and stirring was continued at RT for two days, TLC (DCM:MeOH=20:1) showed that the starting material was consumed. Most of the MeOH was removed in vacuo and the residue was partitioned between water (15 mL) and EA (15 mL). The layers were separated and the aqueous layer was further extracted with EA (20 mL). The combined organic extracts were washed with brine, dried over $Na_2SO_4$, filtered and concentrated in vacuo. The residue was purified by chromatography (DCM:MeOH=120:1 to 50:1) to give 34b (80 mg, 63%) as a yellow oil. LC-MS (Agilent): $R_t$ 3.70 min; m/z calculated for $C_{30}H_{34}N_2O_3$ $[M+H]^+$ 471.3. found $[M+H]^+$ 471.3.

3. Procedure for the Preparation of 34

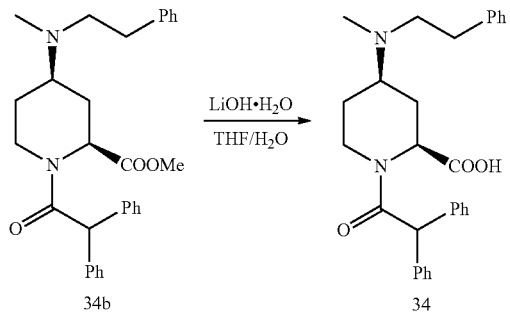 [SMILES: COC(=O)[C@@H]1C[C@H](N(C)CCc2ccccc2)CCN1C(=O)C(c1ccccc1)c1ccccc1 ; "LiOH·H2O" ; CN(CCc1ccccc1)[C@@H]1CCN(C(=O)C(c2ccccc2)c2ccccc2)[C@H](C(=O)O)C1]

To a mixture of 34b (80 mg, 0.17 mmol) in THF/water (6 mL/2 mL) was added LiOH.H$_2$O (14 mg, 0.34 mmol) and the mixture was stirred at RT overnight, TLC (DCM: MeOH=20:1) showed that the starting material was consumed. Most of the THF was removed in vacuo and the residue was dissolved in water (20 mL) and washed with ether (15 mL). DCM (15 mL) was added and the aqueous layer was acidified to pH 2-3 with a 1 M aqueous HCl solution. The layers were separated and the aqueous layer was further extracted with DCM (15 mL). The organic phase was washed with brine, dried over Na$_2$SO$_4$, filtered and concentrated in vacuo. The residue was purified by preparative HPLC to give 34 (40 mg, 52%) as a white solid. LC-MS (Agilent): R$_t$ 3.77 min; m/z calculated for C$_{29}$H$_{32}$N$_2$O$_3$ [M+H]$^+$ 457.3. found [M+H]$^+$ 457.3. HPLC (214 and 254 nm): R$_t$ 8.72 min.

Example 9: Compound 35 (2S,4S)-1-(2,2-diphenylacetyl)-4-(methyl(3-phenethyl)amino)piperidine-2-carboxylic acid 1. Procedure for the Preparation of 33a

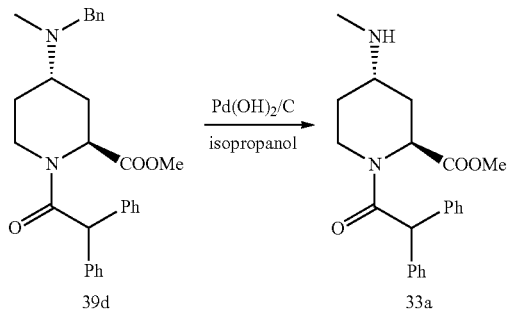 [SMILES: COC(=O)[C@@H]1C[C@@H](N(C)Cc2ccccc2)CCN1C(=O)C(c1ccccc1)c1ccccc1 ; CN[C@H]1CCN(C(=O)C(c2ccccc2)c2ccccc2)[C@H](C(=O)OC)C1]

To a solution of 39d (320 mg, 0.70 mmol) in isopropanol (20 mL) was added 10% Pd(OH)$_2$/C (25 mg) and the mixture was stirred at RT under a H$_2$ atmosphere (1 atm) overnight, TLC (PE:EA=1:1) showed that some of the starting material remained. The mixture was then heated at 30° C. overnight, TLC (PE:EA=1:1) showed that the starting material was consumed. The mixture was filtered and the filtrate was concentrated in vacuo to give 33a (290 mg, >100%) as a colorless oil, which was used in next step without purification. LC-MS (Agilent): R$_t$ 3.39 min; m/z calculated for C$_{22}$H$_{26}$N$_2$O$_3$ [M+H]$^+$ 367.2. found [M+H]$^+$ 367.2.

2. Procedure for the Preparation of 35a

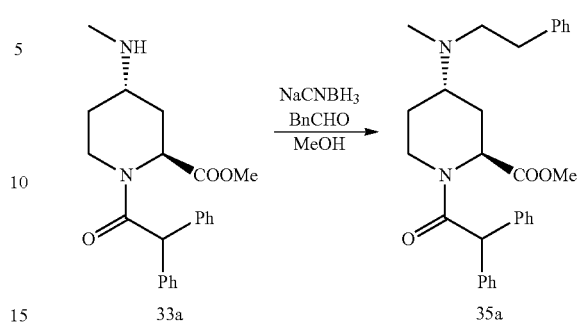

To a stirred solution of 33a (88 mg, 0.24 mmol) and phenylacetaldehyde (43 mg, 0.36 mmol) in MeOH (5 mL) at 0° C. was added 2 drops of AcOH and the mixture was stirred at 0° C. for 1 h. NaCNBH$_3$ (23 mg, 0.36 mmol) was added and the mixture was allowed to warm to RT and stirred overnight, TLC (DCM:MeOH=10:1) showed that the starting material was consumed. Most of the MeOH was removed in vacuo and the residue was dissolved in water (10 mL) and extracted with EA (15 mL×2). The combined organic extracts were washed with brine (10 mL×2), dried over Na$_2$SO$_4$, filtered and concentrated in vacuo. The residue was purified by chromatography (DCM:MeOH=1:0 to 10:1) to give 35a (60 mg, 53%) as a yellow oil. LC-MS (Agilent): R$_t$ 3.34 min; m/z calculated for C$_{30}$H$_{34}$N$_2$O$_3$ [M+H]$^+$ 471.3. found [M+H]$^+$ 471.3.

3. Procedure for the Preparation of 35

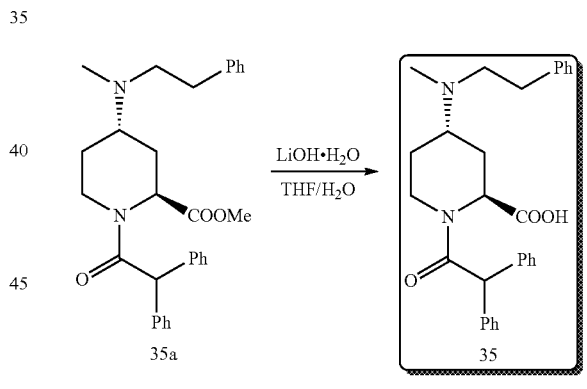

To a mixture of 35a (60 mg, 0.13 mmol) in THF/water (5 mL/1.5 mL) was added LiOH.H$_2$O (16 mg, 0.38 mmol) and the mixture was stirred at RT overnight, TLC (DCM: MeOH=10:1) showed that the starting material was consumed. Most of the THF was removed in vacuo and the residue was dissolved in water (15 mL) and washed with Et$_2$O (10 mL). The aqueous layer was acidified to pH 4-5 with a 3 M aqueous HCl solution and extracted with DCM (15 mL×2). The combined organic extracts were washed with brine, dried over Na$_2$SO$_4$, filtered and concentrated in vacuo. The residue was purified by preparative HPLC to give 35 (25 mg, 43%) as a white solid. LC-MS (Agilent): R$_t$ 3.77 min; m/z calculated for C$_{29}$H$_{32}$N$_2$O$_3$ [M+H]$^+$ 457.2. found [M+H]$^+$ 457.2. HPLC (214 and 254 nm): R$_t$ 8.68 min.

Example 10: Compound 38 (2S,4R)-4-(benzyl(methyl)amino)-1-(2,2-diphenylacetyl)piperidine-2-carboxylic acid

1. Procedure for the Preparation of 38b

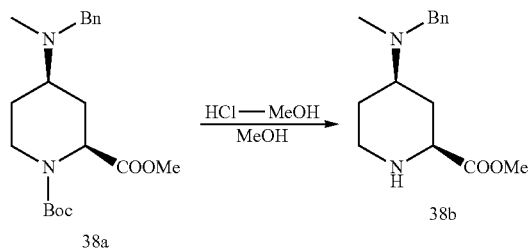

To a solution of 38a (800 mg, 2.2 mmol) in MeOH (3 mL) at RT was added a 4 M HCl/MeOH solution (5 mL) and the mixture was stirred overnight, TLC (PE:EA=2:1) showed that the starting material was consumed. The mixture was concentrated in vacuo, the residue was dissolved with water (20 mL) and washed with Et$_2$O (15 mL). DCM (15 mL) was added and the aqueous layer was basified to pH 8 with K$_2$CO$_3$ and extracted with DCM (15 mL). The combined organic extracts were washed with brine, dried over Na$_2$SO$_4$, filtered and concentrated in vacuo to give 38b (400 mg, 69%) as a yellow oil. LC-MS (Agilent): R$_t$ 0.55 min; m/z calculated for C$_{15}$H$_{22}$N$_2$O$_2$ [M+H]$^+$ 263.2. found [M+H]$^+$ 263.2.

2. Procedure for the Preparation of 34a

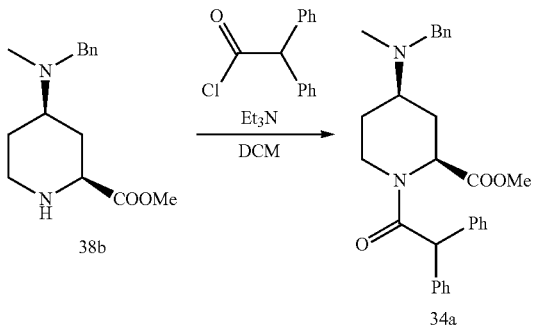 [SMILES: "Et3N" ; COC(=O)[C@@H]1C[C@H](N(C)Cc2ccccc2)CCN1 ; O=C(Cl)C(c1ccccc1)c1ccccc1 ; COC(=O)[C@@H]1C[C@H](N(C)Cc2ccccc2)CCN1C(=O)C(c1ccccc1)c1ccccc1]

To a solution of 38b (400 mg, 1.5 mmol) and Et$_3$N (187 mg, 1.8 mmol) in DCM (10 mL) at 0° C. was added diphenylacetyl chloride (421 mg, 1.8 mmol) and the mixture was stirred at 0° C. for 15 min, TLC (PE:EA=1:1) showed that the starting material was consumed. The mixture was washed with brine, dried over Na$_2$SO$_4$ filtered and concentrated in vacuo. The residue was purified by chromatography (PE:EA=10:1 to 3:1) to give 34a (600 mg, 87%) as a white solid. LC-MS (Agilent): R$_t$ 3.61 min; m/z calculated for C$_{29}$H$_{32}$N$_2$O$_3$ [M+H]$^+$ 457.2. found [M+H]$^+$ 457.2.

3. Procedure for the Preparation of 38

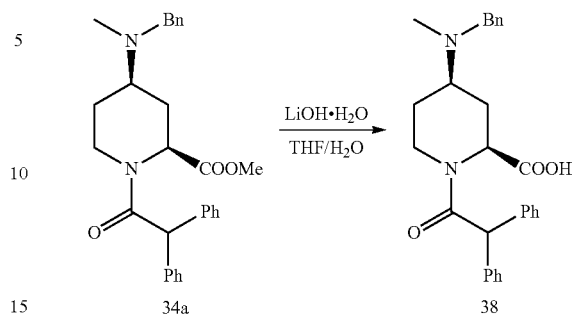

To a mixture of 34a (50 mg, 0.1 mmol) in THF/water (6 mL/2 mL) was added LiOH.H$_2$O (10 mg, 0.2 mmol) and the mixture was stirred at RT overnight, TLC (PE:EA=1:1) showed that the starting material was consumed. Most of the THF was removed in vacuo and the residue was dissolved in water (20 mL) and washed with Et$_2$O (15 mL). DCM (15 mL) was added and the aqueous layer was acidified to pH 2~3 with a 1 M aqueous HCl solution. The organic layer was separated and washed with brine, dried over Na$_2$SO$_4$, filtered and concentrated in vacuo. Purification by preparative HPLC gave 38 (10 mg, 23%) as a white solid. LC-MS (Agilent): R$_t$ 3.73 min; m/z calculated for C$_{28}$H$_{30}$N$_2$O$_3$ [M+H]$^+$ 443.2. found [M+H]$^+$ 443.2. HPLC (214 and 254 nm): R$_t$ 8.57 min.

Example 11: Compound 39 (2S,4S)-4-(benzyl(methyl)amino)-1-(2,2-diphenylacetyl)piperidine-2-carboxylic acid

1. Procedure for the Preparation of 26a

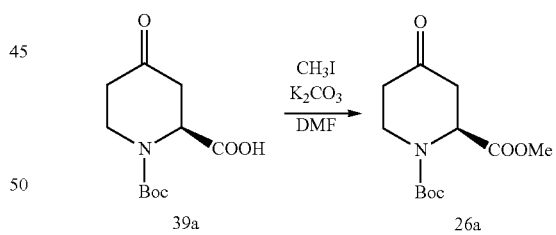

To a solution of 39a (16.0 g, 65.8 mmol) in DMF (130 mL) at 0° C. was added K$_2$CO$_3$ (13.6 g, 98.7 mmol) followed by CH$_3$I (11.4 g, 78.9 mmol) and the mixture was allowed to warm slowly to RT and stirred overnight, TLC (DCM:MeOH=10:1) showed that the starting material was consumed. The mixture was poured into ice-water (600 mL) and extracted with ether (100 mL×4). The combined organic extracts were washed with brine (200 mL×2), dried over Na$_2$SO$_4$, filtered and concentrated in vacuo. The residue was purified by chromatography (PE:EA=1:0 to 4:1) to give 26a (8.0 g, 47%) as a colorless oil. LC-MS (Agilent): R$_t$ 3.20 min; m/z calculated for C$_{12}$H$_{19}$NO$_5$ [M+H-boc]$^+$ 158.1. found[M+H-boc]$^+$ 158.1.

2. Procedure for the Preparation of 39b

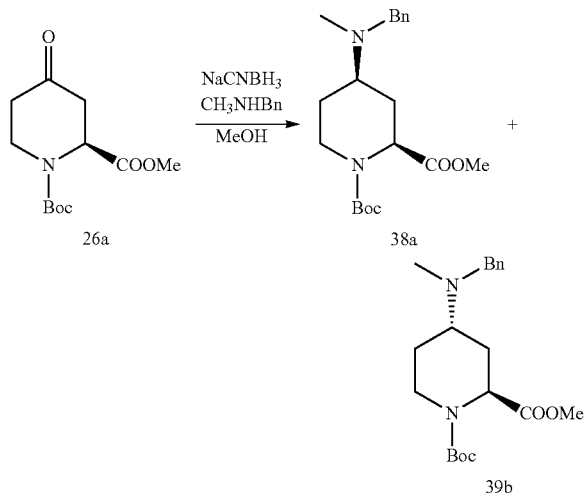

To a solution of 26a (4.00 g, 15.5 mmol) in MeOH (50 mL) was added CH$_3$NHBn (2.06 g, 17.1 mmol) followed by 2 drops of AcOH and the mixture was stirred at RT for 1 hour then cooled to 0° C. NaCNBH$_3$ (1.17 g, 18.6 mmol) was added and the mixture was allowed to warm slowly to RT and stirred overnight, TLC (PE:EA=2:1) showed that the starting material was consumed. Most of the MeOH was removed in vacuo and the residue was partitioned between EA (60 mL) and brine (60 mL). The organic layer was separated, dried over Na$_2$SO$_4$, filtered and concentrated in vacuo. The residue was purified by chromatography (PE:EA=1:0 to 4:1) to give 38a (0.82 g, 15%) followed by 39b (1.3 g, 23%) as colorless oils. LC-MS for 38a (Agilent): R$_t$ 3.47 min; m/z calculated for C$_{20}$H$_{30}$N$_2$O$_4$ [M+H]$^+$ 363.2. found [M+H]$^+$ 363.2. LC-MS for 39b (Agilent): R$_t$ 3.47 min; m/z calculated for C$_{20}$H$_{30}$N$_2$O$_4$ [M+H]$^+$ 363.2. found [M+H]$^+$ 363.2.

3. Procedure for the Preparation of 39c

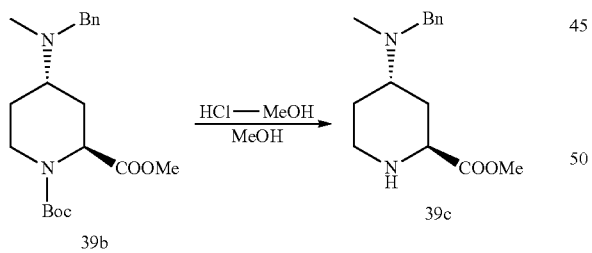

To a solution of 39b (1.00 g, 2.76 mmol) in MeOH (4 mL) was added a 4 M HCl/MeOH solution (5 mL) and the mixture was stirred at RT overnight, TLC (DCM:MeOH=10:1) showed that the starting material was consumed. Most of the MeOH was removed in vacuo and the residue was dissolved in water and washed with ether. The aqueous layer was basified to pH 7-8 with K$_2$CO$_3$ and extracted three times with DCM. The combined organic extracts were washed with brine, dried over Na$_2$SO$_4$, filtered and concentrated in vacuo to give 39c (220 mg, 30%) as a yellow oil. LC-MS (Agilent): R$_t$ 0.61 min; m/z calculated for C$_{15}$H$_{22}$N$_2$O$_2$ [M+H]$^+$ 263.2. found [M+H]$^+$ 263.2.

4. Procedure for the Preparation of 39d

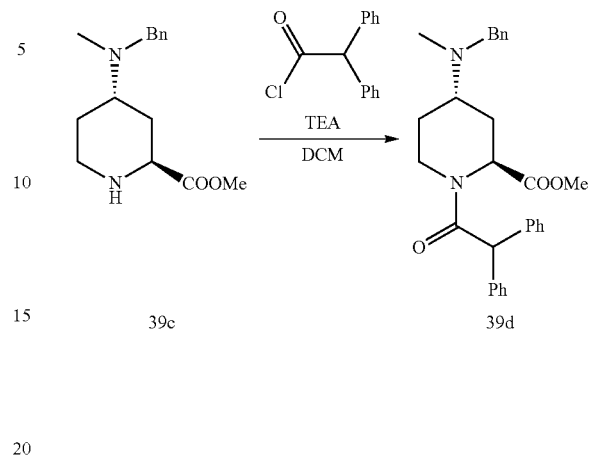

A solution of 39c (310 mg, 1.18 mmol), diphenylacetyl chloride (326 mg, 1.42 mmol) and TEA (144 mg, 1.42 mmol) in DCM (15 mL) was stirred at 0° C. for 20 min, TLC (DCM:MeOH=10:1) showed that the starting material was consumed. The mixture was washed with brine (15 mL×2) and the organic layer was dried over Na$_2$SO$_4$, filtered and concentrated in vacuo. The residue was purified by chromatography (PE:EA=6:1 to 3:1) to give 39d (420 mg, 78%) as a yellow oil. LC-MS (Agilent): R$_t$ 3.31 min; m/z calculated for C$_{29}$H$_{32}$N$_2$O$_3$ [M+H]$^+$ 457.2. found [M+H]$^+$ 457.2.

5. Procedure for the Preparation of 39

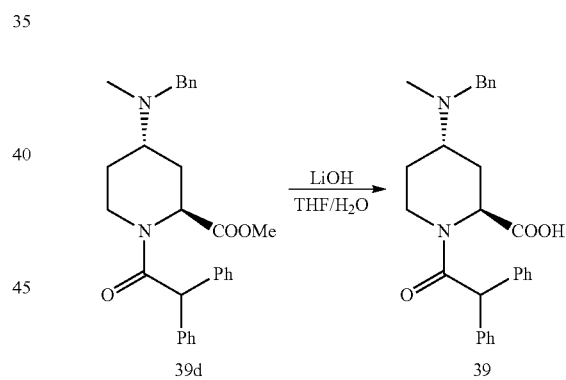

To a mixture of 39d (46 mg, 0.10 mmol) in THF/water (7 mL/2 mL) was added LiOH.H$_2$O (13 mg, 0.30 mmol) and the mixture was stirred at RT overnight, TLC (DCM:MeOH=10:1) showed that the starting material was consumed. Most of the THF was removed in vacuo and the residue was dissolved in water (10 mL), acidified to pH 5-6 with a 3 M aqueous HCl solution and extracted with EA (10 mL×2). The combined organic extracts were washed with brine, dried over Na$_2$SO$_4$, filtered and concentrated in vacuo. The white solid obtained was purified by preparative HPLC to give 39 (15 mg, 34%) as white solid. LC-MS (Agilent): R$_t$ 3.68 min; m/z calculated for C$_{28}$H$_{30}$N$_2$O$_3$ [M+H]$^+$ 443.2. found [M+H]$^+$ 443.2. HPLC (214 and 254 nm): R$_t$ 8.52 min.

Example 12: Compound 40 (2S,4R)-1-(2,2-diphenylacetyl)-4-((3-phenylprop-2-yn-yl)oxy)piperidine-2-carboxylic acid 1. Procedure for the Preparation of 30a

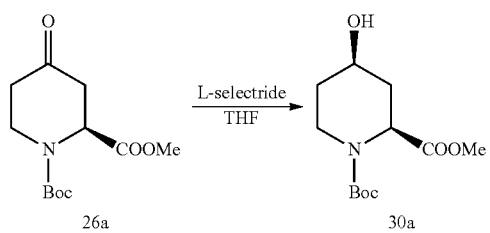 [SMILES: COC(=O)[C@@H]1CC(=O)CCN1C(=O)OC(C)(C)C ; COC(=O)[C@@H]1C[C@H](O)CCN1C(=O)OC(C)(C)C ; "THF"]

To a solution of 26a (2.00 g, 7.77 mmoL) in THF (15 mL) at −78° C. was added L-selectride (1 M solution in THF, 11.7 mL, 11.7 mmol) dropwise and the mixture was stirred at −78° C. for 1 h, TLC (PE:EA=2:1) showed that the starting material was consumed. The reaction was quenched with a saturated aqueous $NH_4Cl$ solution then partitioned between water (20 mL) and EA (30 mL). The organic layer was separated and washed with brine (20 mL×2), dried over $Na_2SO_4$, filtered and concentrated in vacuo to give 30a (1.80 g, 89%) as a colorless oil. LC-MS (Agilent, P-2): $R_t$ 3.84 min; m/z calculated for $C_{12}H_{21}NO_5$ $[M+H]^+$ 260.1 found $[M+H]^+$ 260.1.

2. Procedure for the Preparation of 30c

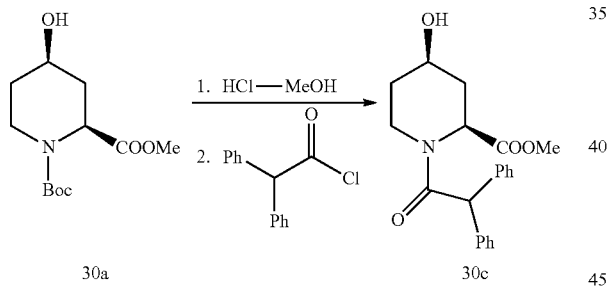

To a solution of 40a (1.80 g, 6.94 mmol) in MeOH (2 mL) was added a 4 M HCl/MeOH solution (10 mL) and the mixture was stirred at RT overnight, TLC (PE:EA=2:1) showed the starting material was consumed. The mixture was concentrated in vacuo and the residue was dissolved in water (15 mL) and cooled to 0° C. $K_2CO_3$ (1.92 g) was added followed by a solution of diphenylacetyl chloride (1.92 g, 8.33 mmol) in EA (15 mL) dropwise and the mixture was stirred at RT overnight. The layers were separated and the organic phase was washed with brine, dried over $Na_2SO_4$, filtered and concentrated in vacuo. The residue was purified by chromatography (PE:EA=1:0 to 3:2) to give the product (254 mg, 10%) as a colorless oil. LC-MS (Agilent, P-2): $R_t$ 2.75 min; m/z calculated for $C_{21}H_{23}NO_4$ $[M+H]^+$ 354.2, $[M+Na]^+$ 376.1. found $[M+H]^+$ 354.2, $[M+Na]^+$ 376.1.

3. Procedure for the Preparation of 40a

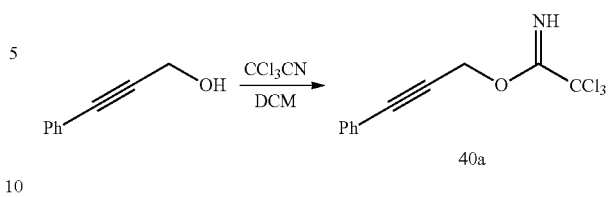

To a solution of 3-phenylprop-2-yn-1-ol (1.00 g, 7.57 mmol) in DCM (20 mL) was added DBU (115 mg, 0.757 mmol) and the mixture was stirred at RT for 10 min then cooled to 0° C. Trichloroacetonitrile (2.20 g, 15.1 mmol) was added and the mixture was then heated at reflux for 10 min, TLC (PE:EA=10:1) showed that the starting material was consumed. The mixture was concentrated in vacuo and the residue was purified by chromatography (PE:EA=1:0 to 20:1) to give 40a (1.50 g, 72%) as a colorless oil.

4. Procedure for the Preparation of 40b

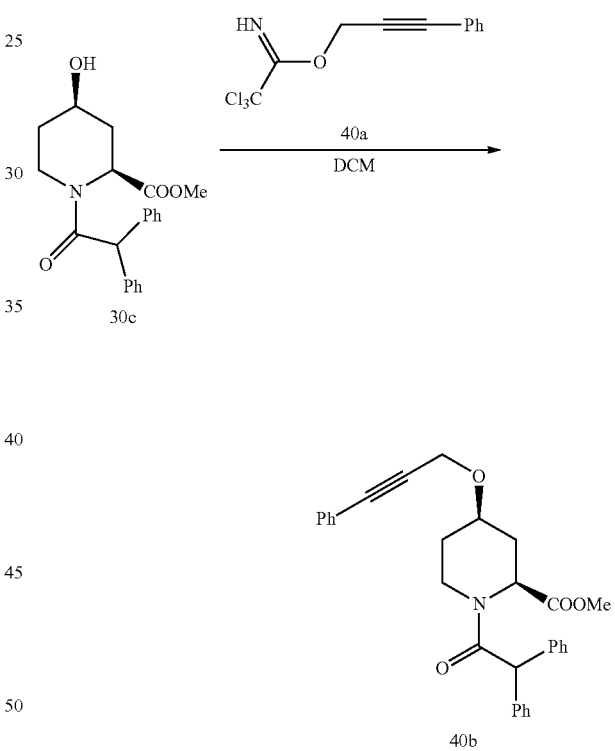

To a solution of 30c (254 mg, 0.72 mmol) and 40a (298 mg, 1.08 mmol) in DCM (15 mL) was added $CF_3SO_3H$ (1 drop) and the mixture was stirred at RT overnight, TLC (PE:EA=2:1) showed some of the starting material remained and a new product was formed. The mixture was washed with brine (10 mL), dried over $Na_2SO_4$, filtered and concentrated in vacuo. The residue was purified by chromatography (PE:EA=1:0 to 5:1) to give 40b (54 mg, 16%) as a colorless oil. LC-MS (Agilent, P-2): $R_t$ 2.83 min; m/z calculated for $C_{30}H_{29}NO_4$ $[M+H]^+$ 468.2, $[M+Na]^+$ 490.2. found $[M+H]^+$ 468.2, $[M+Na]^+$ 490.2.

5. Procedure for the Preparation of 40

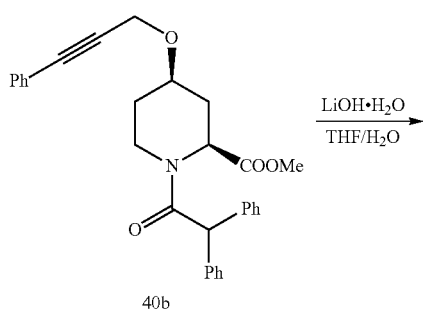

40b

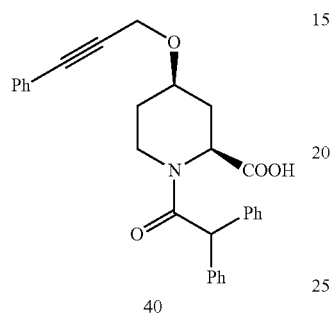

40

A mixture of 40b (54 mg, 0.12 mmol) and LiOH·H$_2$O (15 mg, 0.35 mmol) in THF/water (10 mL/2 mL) was stirred at RT for 48 h, TLC (PE:EA=2:1) showed that the starting material was consumed. Most of the THF was removed in vacuo and the residue was dissolved in water (5 mL) and washed with Et$_2$O (8 mL×2). The aqueous layer was acidified to pH 4~5 with a 4 M aqueous HCl solution, extracted with DCM (10 mL×2) and the combined organic extracts were washed with brine, dried over Na$_2$SO$_4$, filtered and concentrated in vacuo, The residue was purified by preparative HPLC to give 40 (15 mg, 29%) as a white solid. Analytical HPLC and NMR analysis revealed the presence of a ~87:13 mixture of cis/trans isomers. LC-MS (Agilent, P-2): R$_t$ 3.03 min; m/z calculated for C$_{29}$H$_{27}$NO$_4$ [M+H]$^+$ 454.2, [M+Na]$^+$ 476.2. found [M+H]$^+$ 454.2, [M+Na]$^+$ 476.2. HPLC (ZSJ-2) (214 and 254 nm): R$_t$ 21.88 min (minor) and 22.35 min (major).

Example 13: Compound 41 (2S,4R)-1-(2,2-diphenylacetyl)-4-((3-phenylpropyl)oxy)piperidine-2-carboxylic acid

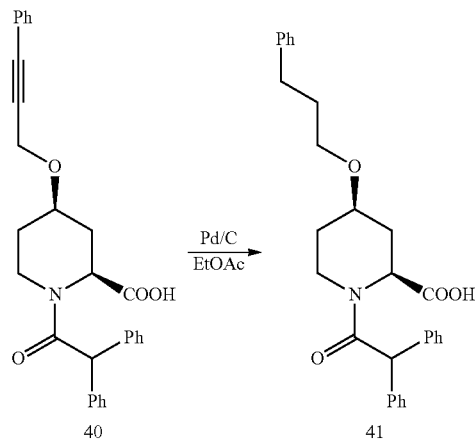 [SMILES: "EtOAc" ; O=C(O)[C@@H]1C[C@H](OCC#Cc2ccccc2)CCN1C(=O)C(c1ccccc1)c1ccccc1 ; O=C(O)[C@@H]1C[C@H](OCCCc2ccccc2)CCN1C(=O)C(c1ccccc1)c1ccccc1]

A mixture of 40 (10 mg, 0.02 mmol) and 10% Pd/C (3 mg) in EA (10 mL) was stirred at RT under a H$_2$ atmosphere (1 atm) for 2 h, TLC (DCM:MeOH=10:1) showed that the starting material was consumed. The mixture was filtered and the filtrate was concentrated in vacuo to give 41 (8 mg, 80%) as a white solid. LC-MS (Agilent, P-2): R$_t$ 2.99 min; m/z calculated for C$_{29}$H$_{31}$NO$_4$ [M+H]$^+$ 471.3, [M+Na]$^+$ 480.2. found [M+H]$^+$ 471.3, [M+Na]$^+$ 480.2. HPLC (JULY-L) (214 and 254 nm): R$_t$ 9.37 min.

Example 14: Compound 42 (2S,4R)-4-((but-2-yn-1-yl)methyl)amino)-1-(2,2-diphenylacetyl)piperidine-2-carboxylic acid 1. Procedure for the Preparation of 42a

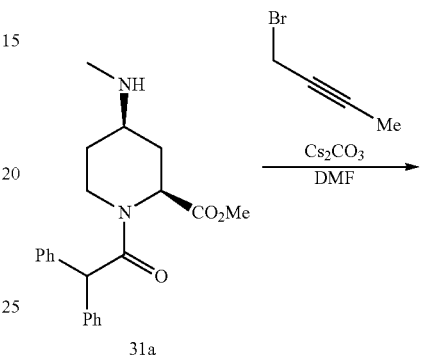

31a

42a

A mixture of 31a (300 mg, 0.81 mmol), 1-bromo-2-butyne (130 mg, 0.98 mmol) and Cs$_2$CO$_3$ (320 mg, 0.98 mmol) in DMF (10 mL) was heated at 50° C. in a sealed tube overnight, TLC (DCM:MeOH=10:1) showed that the starting material was consumed. The mixture was cooled to RT, poured into ice-water (30 mL) and extracted with EA (15 mL×3). The combined organic extracts were washed with brine, dried over Na$_2$SO$_4$, filtered and concentrated in vacuo. The residue was purified by chromatography (PE:EA=1:0 to 4:1) to give 42a (120 mg, 35%) as a white solid. LC-MS (Agilent, P-2): R$_t$ 2.65 min; m/z calculated for C$_{26}$H$_{30}$N$_2$O$_3$ [M+H]$^+$ 419.2. found [M+H]$^+$ 419.2.

2. Procedure for the Preparation of 42

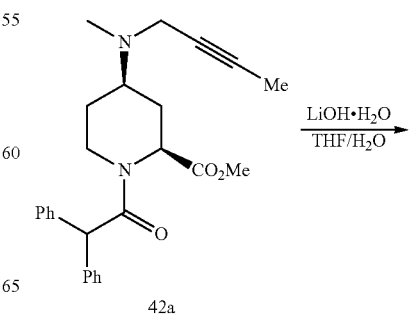

42a

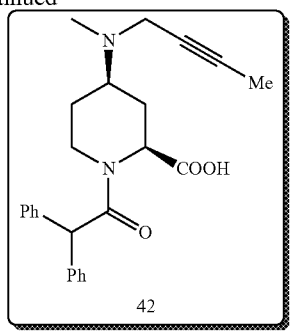

A mixture of 42a (120 mg, 0.28 mmol) and LiOH·H$_2$O (36 mg, 0.86 mmol) in THF/water (3 mL/1 mL) was stirred at RT overnight, TLC (PE:EA=2:1) showed that the starting material was consumed. Most of the THF was removed in vacuo, the residue was dissolved in water (20 mL), acidified to pH 3-4 with a 3 M aqueous HCl solution and extracted with DCM (15 mL×3). The combined organic extracts were washed with brine, dried over Na$_2$SO$_4$, filtered and concentrated in vacuo. The residue was purified by preparative HPLC to give 42 (80 mg, 71%) as a white solid. LC-MS (Agilent, P-2): R$_t$ 2.72 min; m/z calculated for C$_{25}$H$_{28}$N$_2$O$_3$ [M+H]$^+$ 405.2. found [M+H]$^+$ 405.2. HPLC (JULY-L) (214 and 254 nm): R$_t$ 8.38 min.

Example 15: Compound 43 (2S,4S)-4-((but-2-yn-1-yl)methyl)amino)-1-(2,2-diphenylacetyl)piperidine-2-carboxylic acid 1. Procedure for the Preparation of 43a

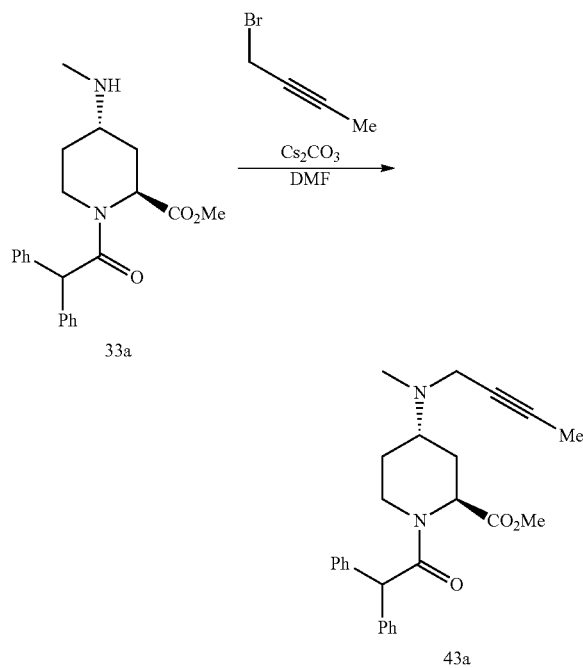

A mixture of 33a (180 mg, 0.49 mmol), 1-bromo-2-butyne (72 mg, 0.54 mmol) and Cs$_2$CO$_3$ (175 mg, 0.54 mmol) in DMF (10 mL) was heated at 40° C. in a sealed tube overnight, TLC (DCM:MeOH=10:1) showed that the starting material was consumed. The mixture was cooled to RT, poured into ice-water (30 mL) and extracted with EA (15 mL×2). The combined organic extracts were washed with brine, dried over Na$_2$SO$_4$, filtered and concentrated in vacuo. The residue was purified by chromatography (PE:EA=1:0 to 2:1) to give 43a (70 mg, 34%) as a colorless oil. LC-MS (Agilent, P-2): R$_t$ 2.94 min; m/z calculated for C$_{26}$H$_{30}$N$_2$O$_3$ [M+H]$^+$ 419.2. found [M+H]$^+$ 419.2.

2. Procedure for the Preparation of 43

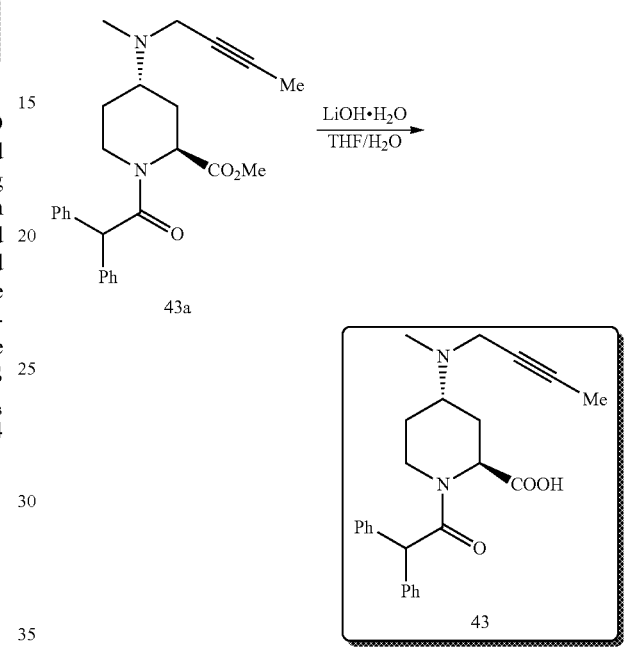

A mixture of 43a (65 mg, 0.15 mmol) and LiOH·H$_2$O (19 mg, 0.45 mmol) in THF/water (3 mL/1 mL) was stirred at RT overnight, TLC (PE:EA=2:1) showed that the starting material was consumed. Most of the THF was removed in vacuo, the residue was dissolved in water (10 mL), acidified to pH 3-4 with a 3 M aqueous HCl solution and extracted with DCM (10 mL×2). The combined organic extracts were washed with brine, dried over Na$_2$SO$_4$, filtered and concentrated in vacuo. The residue was purified by preparative HPLC give 43 (20 mg, 33%) as a white solid. LC-MS (Agilent, P-2): R$_t$ 2.66 min; m/z calculated for C$_{25}$H$_{28}$N$_2$O$_3$ [M+H]$^+$ 405.2. found [M+H]$^+$ 405.2. HPLC (JULY-L) (214 and 254 nm): R$_t$ 9.06 min.

Example 16: Compound 44 (2S,4R)-1-(2,2-diphenylacetyl)-4-((methyl(4-methylpent-2-yn-1-yl)amino)piperidine-2-carboxylic acid 1. Procedure for the Preparation of 44a

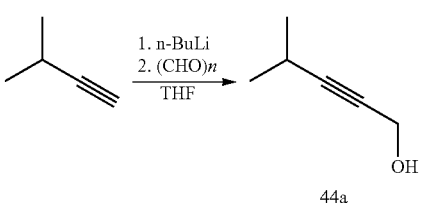

To a solution of 3-methyl-butyne (3.00 g, 43.9 mmol) in THF (30 mL) at −65° C. under $N_2$ was added n-BuLi (2.5 M in hexane, 19.3 mL, 48.2 mmol) and the mixture was stirred at −65° C. for 1 h. Paraformaldehyde (1.97 g, 65.8 mmol) was then added in portions and the mixture was allowed to warm slowly to RT and stirred overnight, TLC (PE:EA=4:1) showed that the starting material was consumed. The mixture was cooled to 0° C. and the reaction was quenched with a saturated aqueous $NH_4Cl$ solution then partitioned between ether and brine. The layers were separated and the organic layer was dried over $Na_2SO_4$, filtered and concentrated in vacuo to give 44a (4.0 g, 93%) as a yellow oil, which was used directly in the next step.

2. Procedure for the Preparation of 44b

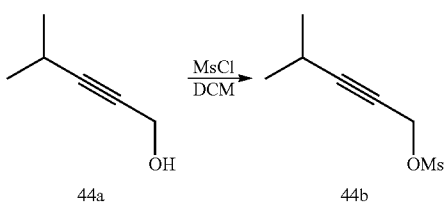

To a solution of 44a (2.5 g, 25.5 mmol) and $Et_3N$ (2.84 g, 28.1 mmol) in DCM (30 mL) at 0° C. under $N_2$ was added MsCl (2.92 g, 25.5 mmol) and the mixture was stirred at 0° C. for 1 h, TLC (PE:EA=4:1) showed that the starting material was consumed. The mixture was washed with brine (20 mL×2), dried over $Na_2SO_4$, filtered and concentrated in vacuo to give 44b (2.0 g, 44%) as a colorless oil. LC-MS (Agilent, P-2): $R_t$ 2.52 min; m/z calculated for $C_7H_{12}O_3S$ [M+Na]$^+$ 199.0. found [M+H]$^+$ 199.0.

3. Procedure for the Preparation of 44c

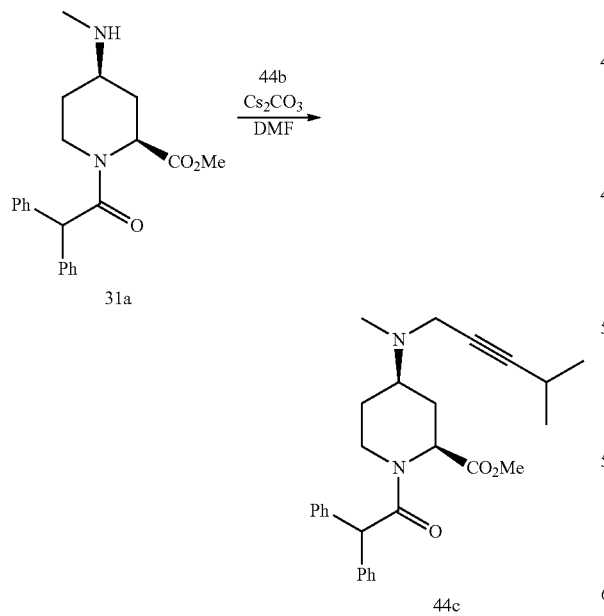

A mixture of 31a (300 mg, 0.82 mmol), 44b (187 mg, 1.06 mmol) and $Cs_2CO_3$ (345 mg, 1.06 mmol) in DMF (5 mL) was heated at 40° C. in a sealed tube overnight, TLC (PE:EA=2:1) showed that most of the starting material was consumed. The mixture was cooled to RT, poured into ice-water (30 mL) and extracted with EA (15 mL×3). The combined organic extracts were washed with brine, dried over $Na_2SO_4$, filtered and concentrated in vacuo. The residue was purified by chromatography (PE:EA=1:0 to 3:1) to give 44c (90 mg, 24%) as a thick, yellow oil. LC-MS (Agilent, P-2): $R_t$ 2.72 min; m/z calculated for $C_{28}H_{34}N_2O_3$ [M+H]$^+$ 447.3. found [M+H]$^+$ 447.3.

4. Procedure for the Preparation of 44

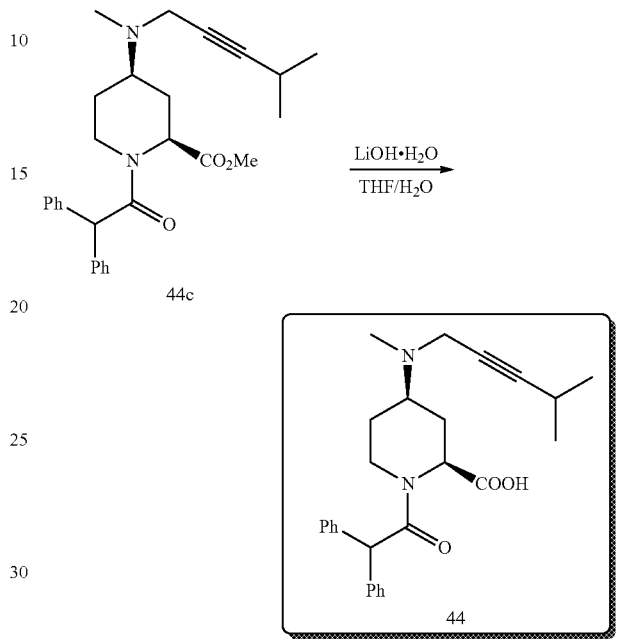

A mixture of 44c (90 mg, 0.20 mmol) and LiOH.$H_2O$ (25 mg, 0.60 mmol) in THF/water (3 mL/1 mL) was stirred at RT overnight, TLC (PE:EA=4:1) showed that the starting material was consumed. Most of the THF was removed in vacuo, the residue was dissolved in water (15 mL), acidified to pH 3 with a 3 M aqueous HCl solution and extracted with DCM (15 mL×3). The combined organic extracts were washed with brine, dried over $Na_2SO_4$, filtered and concentrated in vacuo. The residue was purified by chromatography (DCM:MeOH=1:0 to 50:1) followed by preparative HPLC to give 44 (20 mg, 23%) as a white solid. LC-MS (Agilent, P-2): $R_t$ 2.87 min; m/z calculated for $C_{27}H_{32}N_2O_3$ [M+H]$^+$ 433.2. found [M+H]$^+$ 433.3. HPLC (JULY-L) (214 and 254 nm): $R_t$ 8.71 min.

Example 17: Compound 45 (2S,4S)-1-(2,2-diphenylacetyl)-4-((methyl(4-methylpent-2-yn-1-yl)amino)piperidine-2-carboxylic acid 1. Procedure for the Preparation of 45a

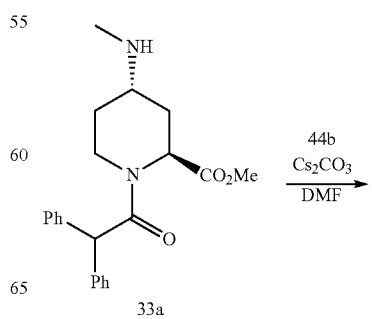

-continued

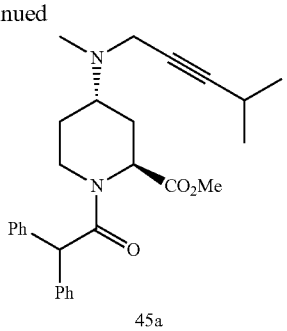

45a

A mixture of 33a (180 mg, 0.49 mmol), 44b (113 mg, 0.63 mmol) and Cs$_2$CO$_3$ (204 mg, 0.63 mmol) in DMF (5 mL) was heated at 40° C. in a sealed tube overnight, TLC (DCM:MeOH=10:1) showed that most of the starting material was consumed. The mixture was cooled to RT, poured into ice-water (30 mL) and extracted with EA (15 mL×2). The combined organic extracts were washed with brine, dried over Na$_2$SO$_4$, filtered and concentrated in vacuo. The residue was purified by chromatography (PE:EA=1:0 to 2:1) to give 45a (50 mg, 23%) as a white solid. LC-MS (Agilent, P-2): R$_t$ 2.73 min; m/z calculated for C$_{28}$H$_{34}$N$_2$O$_3$ [M+H]$^+$ 447.3. found [M+H]$^+$ 447.3.

2. Procedure for the Preparation of 45.

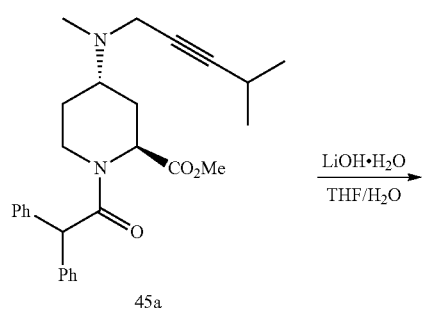

45a

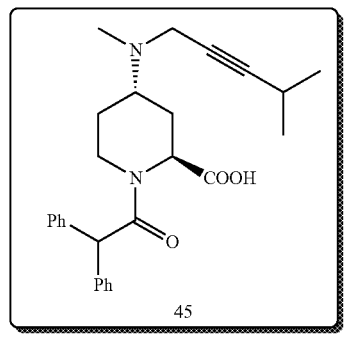

45

A mixture of 45a (50 mg, 0.11 mmol) and LiOH.H$_2$O (14 mg, 0.33 mmol) in THF/water (3 mL/1 mL) was stirred at RT overnight, TLC (PE:EA=1:1) showed that the starting material was consumed. Most of the THF was removed in vacuo, the residue was dissolved in water (15 mL), acidified to pH 5 with a 3 M aqueous HCl solution and extracted with DCM (10 mL×2). The combined organic extracts were washed with brine, dried over Na$_2$SO$_4$, filtered and concentrated in vacuo. The residue was purified by preparative HPLC to give 45 (15 mg, 31%) as a white solid. LC-MS (Agilent, P-2): R$_t$ 2.85 min; m/z calculated for C$_{27}$H$_{32}$N$_2$O$_3$ [M+H]$^+$ 433.2. found [M+H]$^+$ 433.3. HPLC (JULY-L) (214 and 254 nm): R$_t$ 8.63 min.

Example 18: Compound 47 (2S,4S)-1-(2,2-diphenylacetyl)-4-((3-(4-fluorophenyl)prop-2-yn-1-yl)(methyl)amino)piperidine-2-carboxylic acid 1. Procedure for the Preparation of 47a

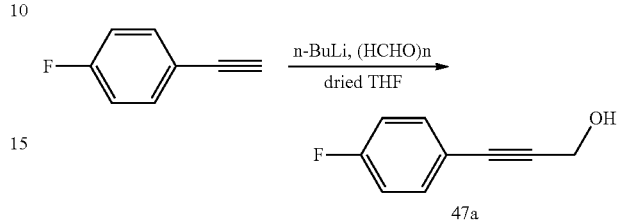

To a stirred solution of 4-fluoro phenylacetylene (5.0 g, 41.7 mmol) in THF (30 mL) at −65° C. under a N$_2$ atmosphere was added n-BuLi (2.5 M in hexane, 18.3 mL, 45.8 mmol) and the mixture was stirred at −65° C. for 1 h. Paraformaldehyde (2.5 g, 83.3 mmol) was added and the mixture was allowed to warm slowly to RT and stirred overnight, TLC (PE:EA=4:1) showed that the starting material was consumed. Water was added and the mixture was extracted with EA (30 mL). The organic extract was washed with water (20 mL×2), brine (20 mL), dried over Na$_2$SO$_4$, filtered and concentrated in vacuo to give 47a (6.5 g, 100%) as a brown oil which was used in next step directly.

2. Procedure for the Preparation of 47b

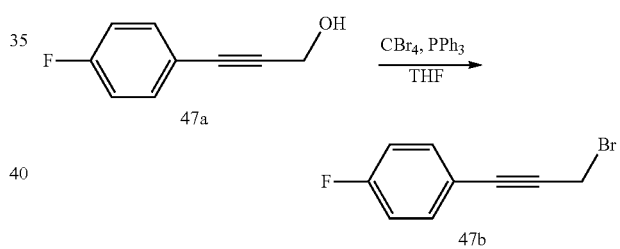

To a solution of 47a (1.0 g, 6.67 mmol) in THF (15 mL) was added PPh$_3$ (1.92 g, 7.34 mmol) then CBr$_4$ (2.21 g, 6.67 mmol) and the mixture was stirred at RT overnight, TLC (PE:EA=4:1) showed that the starting material was consumed. PE (30 mL) was added and the mixture was filtered. The filtrate was concentrated in vacuo and the residue was purified by chromatography (100% PE) to give 47b (1.5 g, 100%) as a colorless oil.

3. Procedure for the Preparation of 47c

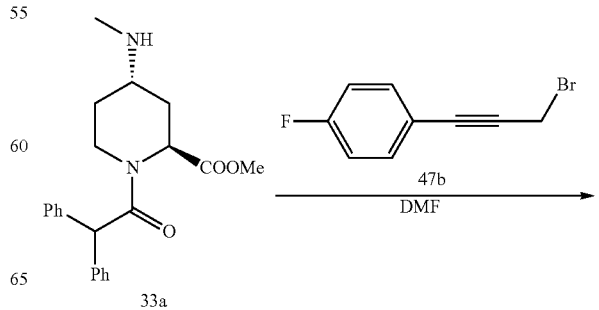

33a

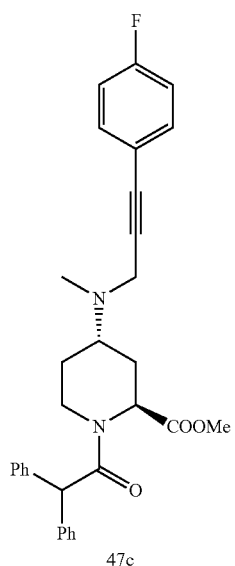

47c

To a solution of 33a (80 mg, 0.22 mmol) in DMF (5 mL) was added K₂CO₃ (46 mg, 0.33 mmol) and 47b (45 mg, 0.22 mmol) and the mixture was stirred at 30° C. overnight, TLC (PE:EA=1:2) showed the starting material was consumed. The mixture was partitioned between EA (30 mL) and H₂O (30 mL), the organic layer was separated, washed with brine, dried over Na₂SO₄, filtered and concentrated in vacuo. The residue was purified by chromatography (PE:EA=10:1 to 1:2) to give 47c (50 mg, 45%) as a colorless oil. LC-MS (Agilent, P-2): R$_t$ 2.964 min; m/z calculated for C$_{31}$H$_{31}$FN$_2$O$_3$ [M+H]$^+$ 499.3. found [M+H]$^+$ 499.3.

4. Procedure for the Preparation of 47

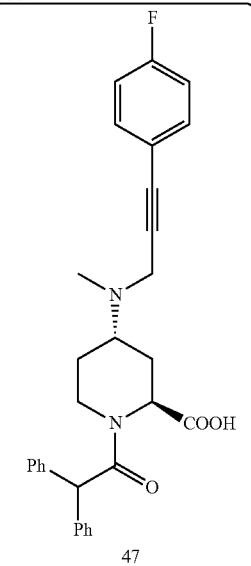

47

A mixture of 47c (50 mg, 0.1 mmol) and LiOH.H₂O (17 mg, 0.4 mmol) in THF/H₂O (5 mL/0.2 mL) was stirred at RT overnight, TLC (PE:EA=1:2) showed that the starting material was consumed. Most of the THF was removed in vacuo and the aqueous residue was acidified to pH 3~4 with a 3 M aqueous HCl solution. The resulting precipitate was collected by filtration then purified by preparative HPLC to give 47 (25 mg, 51%) as a white solid. LC-MS (Agilent, P-2): R$_t$ 2.933 min; m/z calculated for C$_{30}$H$_{29}$FN$_2$O$_3$ [M+H]$^+$ 485.3. found [M+H]$^+$ 485.3. HPLC (JULY-L) (214 and 254 nm): R$_t$ 8.749 min.

Example 19: Compound 46 ((2S,4R)-1-(2,2-diphenylacetyl)-4-((3-(4-fluorophenyl)prop-2-yn-1-yl)(methyl)amino)piperidine-2-carboxylic acid 1. Procedure for the Preparation of 46a

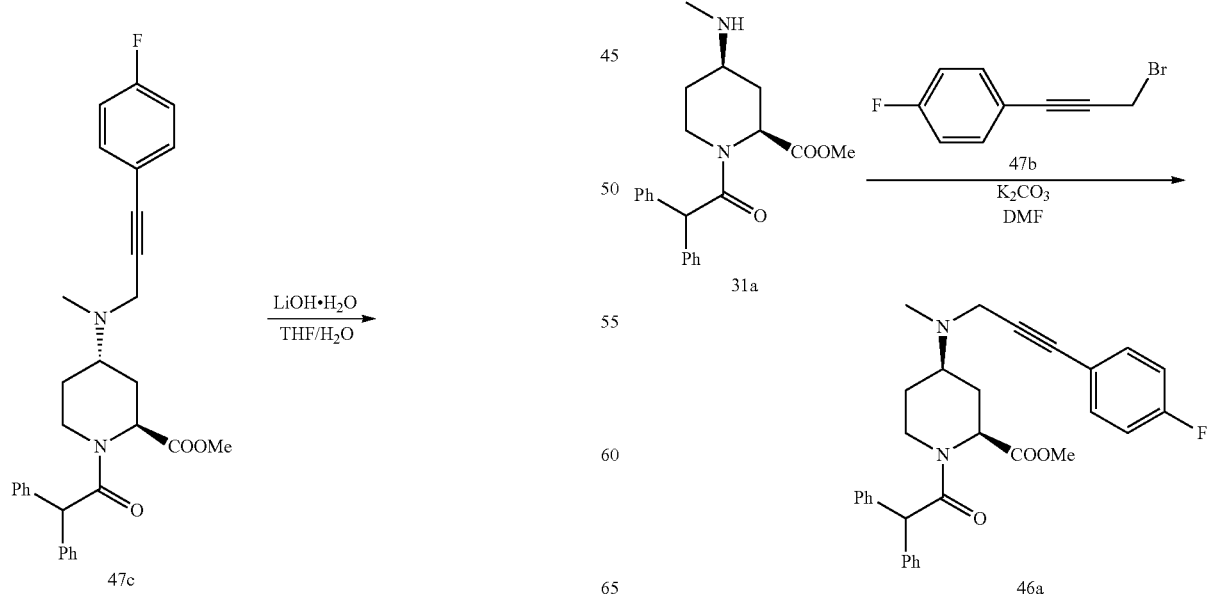

To a stirred solution of 31a (200 mg, 0.54 mmol) in DMF (5 mL) was added K$_2$CO$_3$ (90 mg, 0.65 mmol) then 47b (116 mg, 0.54 mmol) and the mixture was stirred at 30° C. overnight, TLC (DCM:MeOH=10:1) showed that most of the starting material was consumed. The mixture was cooled to 0~5° C., poured into ice-water (40 mL) and extracted with EA (15 mL×3). The combined organic extracts were washed with brine, dried over Na$_2$SO$_4$, filtered and concentrated in vacuo. The residue was purified by chromatography (PE:EA=1:0 to 1:1) to give 46a (84 mg, 31%) as a white solid. LC-MS (Agilent, P-2): R$_t$ 3.08 min; m/z calculated for C$_{31}$H$_{31}$FN$_2$O$_3$[M+H]$^+$ 499.2. found [M+H]$^+$ 499.3.

2. Procedure for the Preparation of 46

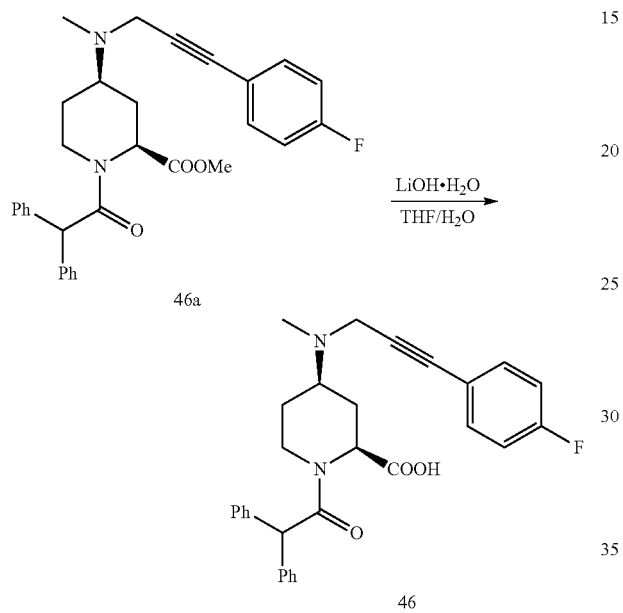

A mixture of 46a (84 mg, 0.17 mmol) and LiOH·H$_2$O (27 mg, 0.64 mmol) in THF/H$_2$O (3 mL/1 mL) was stirred at RT overnight, TLC (PE:EA=1:1) showed the starting material was consumed. The mixture was concentrated in vacuo, the residue was dissolved in water (10 mL), acidified to pH~3 with a 3 M aqueous HCl solution and extracted with DCM (10 mL×3). The organic extracts were washed with brine, dried over Na$_2$SO$_4$, filtered and concentrated in vacuo. The residue was purified by preparative HPLC to give 46 (57 mg, 69%) as a white solid. LC-MS (Agilent, P-2): R$_t$ 3.00 min; m/z calculated for C$_{30}$H$_{29}$FN$_2$O$_3$ [M+H]$^+$ 485.2. found [M+H]$^+$ 485.3. HPLC (JULY-L) (214 and 254 nm): R$_t$ 8.83 min.

Example 20: Compound 52 (2S,4R)-1-(2,2-diphenylacetyl)-4-((3-(4-fluorophenyl)prop-2-yn-1-yl)oxy)piperidine-2-carboxylic acid 1. Procedure for the Preparation of 52a

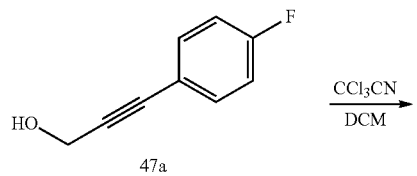

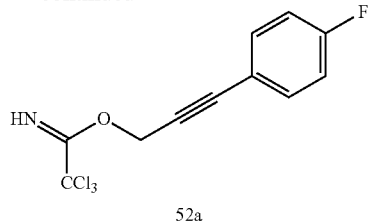

To a solution of 47a (1.00 g, 6.66 mmol) in DCM (20 mL) at 0~5° C. was added DBU (101 mg, 0.66 mmol) and the mixture was stirred at 0~5° C. for 10 min. Trichloroacetonitrile (1.92 g, 13.3 mmol) was then added and stirring was continued for a further 10 min, TLC (PE:EA=10:1) showed that the starting material was consumed. The mixture was washed with brine, dried over Na$_2$SO$_4$, filtered and concentrated in vacuo. The residue was purified by chromatography (PE:EA=1:0 to 20:1) to give 52a (1.2 g, 63%) as a yellow oil.

2. Procedure for the Preparation of 52b

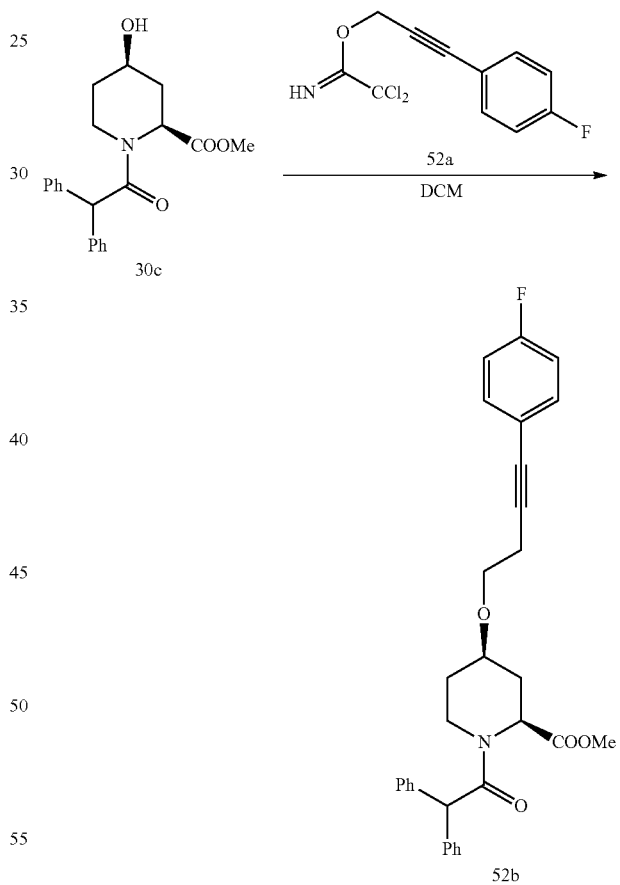

To a solution of 30c (200 mg, 0.56 mmol) and 52a (333 mg, 1.13 mmol) in DCM (10 mL) at −10° C. under a N$_2$ atmosphere was added TMS triflate (37 mg, 0.17 mol) and the mixture was allowed to warm slowly to RT and stirred overnight, TLC (PE:EA=1:1) showed most of the starting material was consumed. The mixture was washed with brine (5 mL×2), dried over Na$_2$SO$_4$, filtered and concentrated in vacuo. The residue was purified by chromatography (PE:EA=1:0 to 4:1) to give 52b (30 mg, 11%) as a colorless oil.

LC-MS (Agilent, P-2): $R_t$ 3.25 min; m/z calculated for $C_{30}H_{28}FNO_4$ [M+H]$^+$ 486.2, [M+Na]$^+$ 508.2. found [M+H]$^+$ 486.2, [M+Na]$^+$ 508.2.

3. Procedure for the Preparation of 52

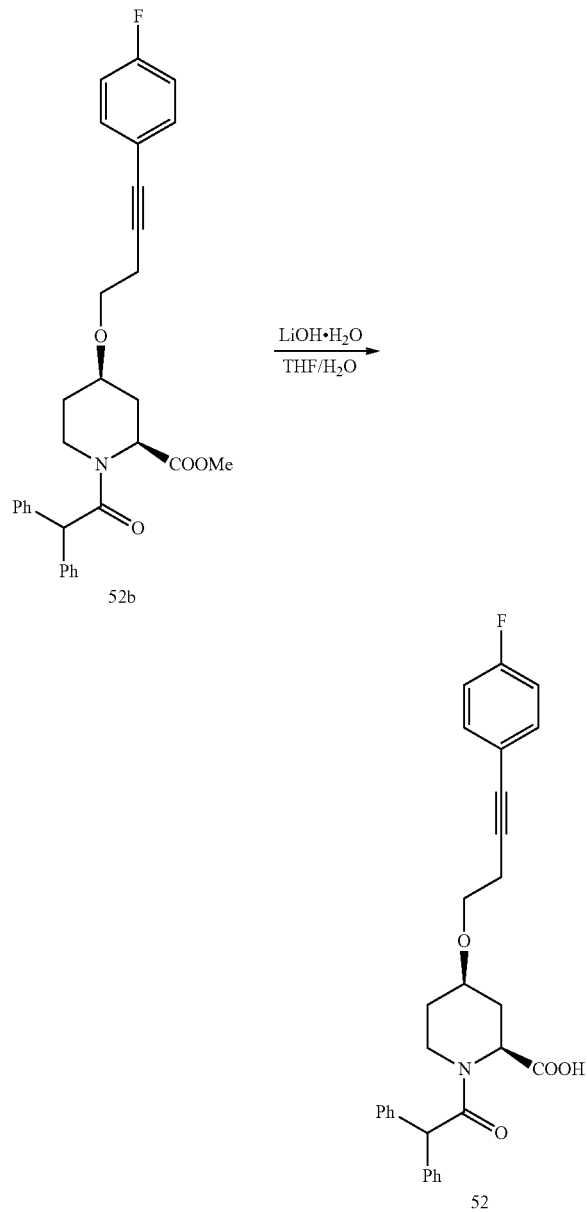

A mixture of 52b (30 mg, 0.062 mmol) and LiOH·H$_2$O (11 mg, 0.25 mmol) in THF/H$_2$O (5 mL/0.5 mL) was stirred at RT for 3 days, TLC (PE:EA=3:1) showed that the starting material was consumed. The mixture was concentrated in vacuo, the residue was dissolved in water (5 mL), acidified to pH 3~4 with a 3 M aqueous HCl solution and extracted with DCM (15 mL×3). The combined organic extracts were dried over Na$_2$SO$_4$, filtered and concentrated in vacuo and the residue was purified by preparative HPLC to give 52 (16 mg, 50%) as a white solid. Analytical HPLC and NMR analysis revealed a ~87:13 mixture of cis/trans isomers. LC-MS (Agilent, P-2): $R_t$ 3.18 min; m/z calculated for $C_{29}H_{26}FNO_4$ [M+H]$^+$ 472.2. found [M+H]$^+$ 472.2. HPLC (JULY-L) (214 and 254 nm): $R_t$ 9.55 min. HPLC (ZSJ-2) (214 and 254 nm): $R_t$ 25.25 min.

Example 21: Compound 57 (2'S,3S,4'R)-1'-(2,2-diphenylacetyl)-3-phenyl-[1,4'-bipiperidine]-2'-carboxylic acid 1. Procedure for the Preparation of 57a

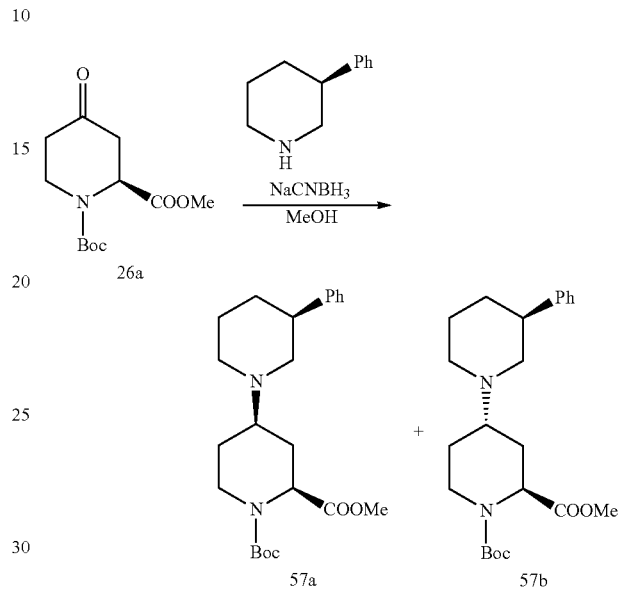

To a solution of 26a (500 mg, 1.94 mmol) and (S)-3-phenylpiperidine (376 mg, 2.33 mmol) in MeOH (10 mL) at 0° C. under N$_2$ was added 2 drops of AcOH and the mixture was stirred at 0° C. for 30 min. NaCNBH$_3$ (158 mg, 2.52 mmol) was added and the mixture was allowed to warm slowly to RT and stirred overnight, TLC (PE:EA=4:1) showed that the starting material was consumed. The solvent was removed in vacuo and the residue was partitioned between EA/brine. The organic layer was separated, dried over Na$_2$SO$_4$, filtered and concentrated in vacuo. The residue was purified by chromatography (PE:EA=1:0 to 1:2) to give 57a (248 mg, 32%) as the first eluting product followed by 57b (191 mg, 24%), each obtained as colorless oils. LC-MS (Agilent, P-2) for 57a: $R_t$ 2.715 min; m/z calculated for $C_{23}H_{34}N_2O_4$ [M+H]$^+$ 403.3. found [M+H]$^+$ 403.3. LC-MS (Agilent, P-2) for 57b: $R_t$ 2.756 min; m/z calculated for $C_{23}H_{34}N_2O_4$ [M+H]$^+$ 403.3, [M+Na]$^+$ 425.3. found [M+H]$^+$ 403.3, [M+Na]$^+$ 425.3.

2. Procedure for the Preparation of 57c

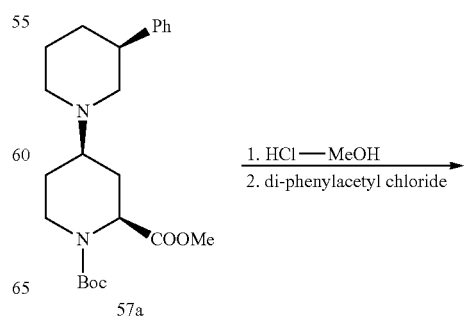

-continued

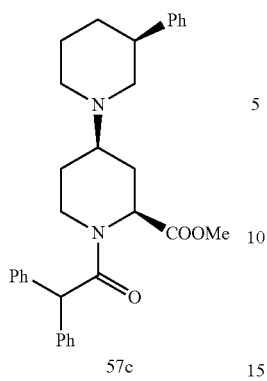

57c

A mixture of 57a (248 mg, 0.62 mmol) in 4 M HCl/MeOH (10 mL) was stirred at RT overnight, TLC (PE:EA=2:1) showed that the starting material was consumed. The mixture was concentrated in vacuo, the residue was dissolved in water (10 mL), washed with ether then basified to pH 9~10 with $K_2CO_3$ and extracted with chloroform/isopropanol (3/1, v/v, 10 mL×6). The combined organic extracts were dried over $Na_2SO_4$, filtered and concentrated in vacuo and the residue was dissolved in DCM (5 mL). $Et_3N$ (102 mg, 0.74 mmol) was added to the obtained DCM solution at 0° C. followed by diphenylacetyl chloride (171 mg, 0.74 mmol) and the mixture was allowed to warm to RT and stirred for 10 min, TLC (DCM:MeOH=10:1) showed that the starting material was consumed. The mixture was washed with brine (5 mL×2), dried over $Na_2SO_4$, filtered and concentrated in vacuo. The residue was purified by chromatography (PE:EA=10:1 to 2:1) to give 57c (93 mg, 30%) as a white solid. LC-MS (Agilent, P-2): $R_t$ 2.75 min; m/z calculated for $C_{32}H_{36}N_2O_3$ $[M+H]^+$ 497.3. found $[M+H]^+$ 497.3.

3. Procedure for the Preparation of 57

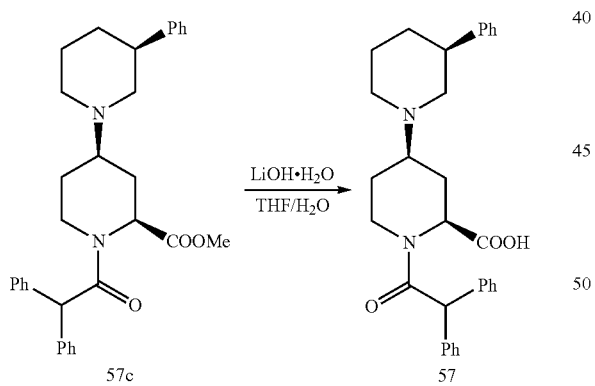

A mixture of 57c (93 mg, 0.187 mmol) and $LiOH·H_2O$ (24 mg, 0.562 mmol) in $THF/H_2O$ (3 mL/1 mL) was stirred at RT overnight, TLC (PE:EA=1:1) showed the starting material was consumed. The mixture was concentrated in vacuo, the residue was dissolved in water (3 mL) and acidified to pH 4~5 with a 4 M aqueous HCl solution. The resulting precipitate was collected by filtration and the filter cake was crystallized from EA/ether to give 57 (38 mg, 42%) as a white solid. LC-MS (Agilent, P-2): $R_t$ 3.05 min; m/z calculated for $C_{31}H_{34}N_2O_3$ $[M+H]^+$ 483.3. found $[M+H]^+$ 483.3. HPLC (JULY-L) (214 and 254 nm): $R_t$ 8.65 min.

Example 22: Compound 58 (2'S,3S,4'S)-1'-(2,2-diphenylacetyl)-3-phenyl-[1,4'-bipiperidine]-2'-carboxylic acid 1. Procedure for the Preparation of 58a

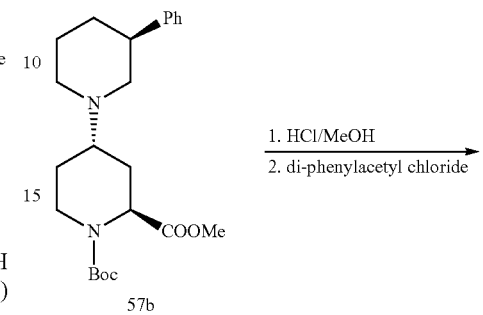

57b

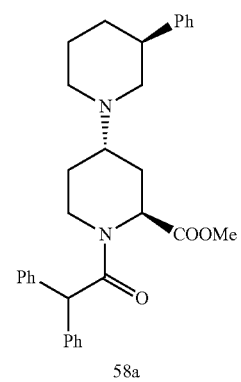

58a

A mixture of 57b (191 mg, 0.47 mmol) in 4 M HCl/MeOH (15 mL) was stirred at RT overnight, TLC (PE:EA=2:1) showed that the starting material was consumed. The mixture was concentrated in vacuo, the residue was dissolved in water (10 mL), washed with ether (10 mL) then basified to pH 9~10 with $K_2CO_3$ and extracted with $IPA/CHCl_3$ (⅓, v/v, 10 mL×5). The combined organic extracts were dried over $Na_2SO_4$, filtered and concentrated in vacuo. The residue was dissolved in DCM (5 mL), cooled to 0° C. and $Et_3N$ (79 mg, 0.57 mmol) then di-phenylacetyl chloride (131 mg, 0.57 mmol) were added. The mixture was allowed to warm to RT and stirred for 10 min, TLC (DCM:MeOH=10:1) showed that the starting material was consumed. The mixture was washed with brine (5 mL×2), dried over $Na_2SO_4$, filtered and concentrated in vacuo. The residue was purified by chromatography (PE:EA-10:1 to 1.5:1) to give 58a (40 mg, 17%) as a colorless oil. LC-MS (Agilent, P-2): $R_t$ 3.05 min; m/z calculated for $C_{32}H_{36}N_2O_3$ $[M+H]^+$ 497.3. found $[M+H]^+$ 497.3.

2. Procedure for the Preparation of 58

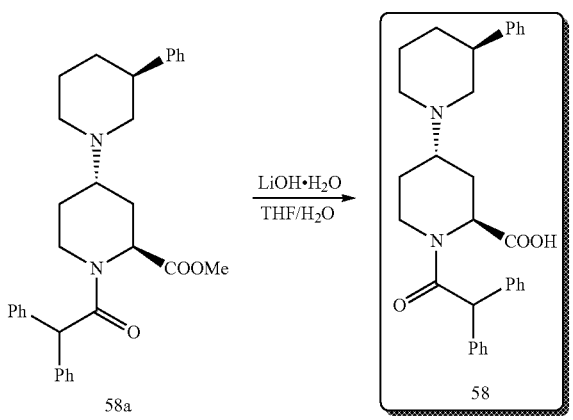

A mixture of 58a (40 mg, 0.080 mmol) and LiOH.H₂O (10 mg, 0.241 mmol) in THF/H₂O (3 mL/1 mL) was stirred at RT overnight, TLC (PE:EA=1:2) showed that the starting material was consumed. The mixture was concentrated in vacuo, the residue was dissolved in water (8 mL), acidified to pH 4~5 with a 4 M aqueous HCl solution and extracted with DCM (10 mL×3). The combined organic extracts were washed with brine (15 mL×2), dried over Na₂SO₄, filtered and concentrated in vacuo. The residue was purified by preparative HPLC to give 58 (30 mg, 78%) as a white solid. LC-MS (Agilent, P-2): $R_t$ 2.83 min; m/z calculated for $C_{31}H_{34}N_2O_3$ [M+H]⁺ 483.3. found [M+H]⁺ 483.3. HPLC (JULY-L) (214 and 254 nm): $R_t$ 8.70 min.

Example 23: Compound 54 (2S,4R)-4-((4,4-dimethylpent-2-yn-1-yl)(methyl)amino)-1-(2,2-diphenylacetyl)piperidine-2-carboxylic acid 1. Procedure for the Preparation of 54a

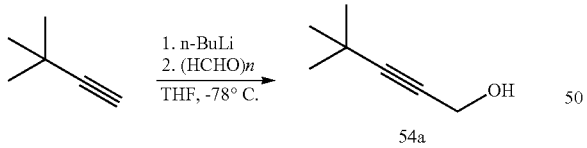

To a solution of 3,3-dimethylbut-1-yne (6.0 g, 24.4 mmol) in THF (30 mL) at −65° C. under a N₂ atmosphere was slowly added n-BuLi (2.5 M in hexane, 10.7 mL, 26.8 mmol) and the mixture was stirred at −65° C. for 1 h. Paraformaldehyde (1.46 g, 48.8 mmol) was then added in portions and the mixture was allowed to warm to RT and stirred overnight, TLC (PE:EA=4:1) showed that the starting material was consumed. The reaction was quenched with water and the mixture was extracted with EA (50 mL×3). The combined organic extracts were washed with water then brine, dried over Na₂SO₄, filtered and concentrated in vacuo to give 54a (6.0 g, 74%) as a colorless oil, which was used directly in the next step.

2. Procedure for the Preparation of 54b

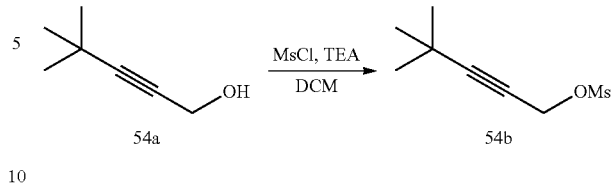

To a solution of 54a (1.0 g, 8.9 mmol) in DCM (10 mL) at 0° C. was added triethylamine (1.08 g, 10.7 mmol) and the mixture was stirred at 0° C. for 10 min. MsCl (1.1 g, 9.8 mmol) was then added and the mixture was stirred at 0° C. for 30 min, TLC (PE:EA=4:1) showed that the starting material was consumed. The reaction was quenched with water, the organic layer was collected, washed with brine, dried over Na₂SO₄, filtered and concentrated in vacuo. The residue was purified by chromatography (PE:EA=20:1 to 5:1) to give 54b (850 mg, 50%) as a colorless oil.

3. Procedure for the Preparation of 54c

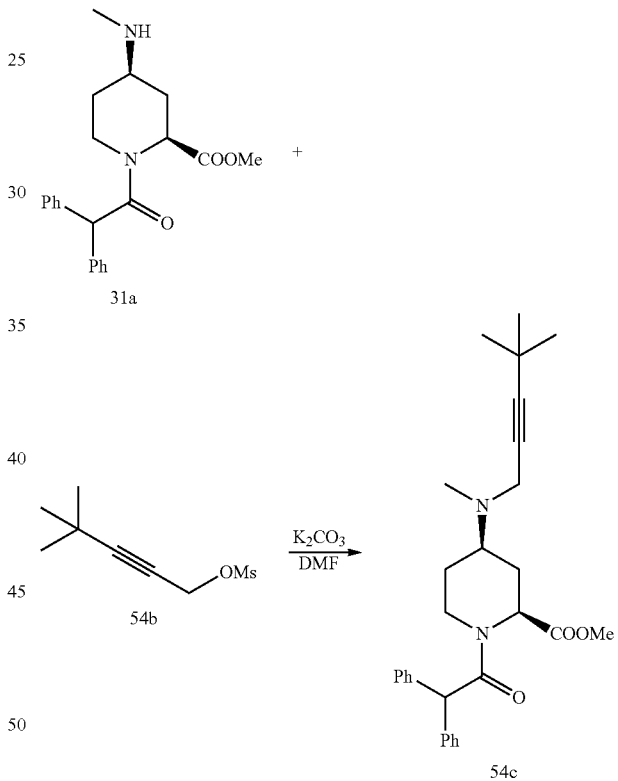

To a solution of 31a (300 mg, 0.82 mmol) in DMF (10 mL) was added K₂CO₃ (226 mg, 1.64 mmol) and 54b (186 mg, 0.98 mmol) and the mixture was heated at 60° C. overnight, TLC (PE:EA=2:1) showed that the starting material was consumed. The mixture was cooled to RT and partitioned between EA (30 mL) and H₂O (40 mL). The layers were separated and the aqueous layer was extracted with EA (20 mL). The combined organic extracts were washed with brine, dried over Na₂SO₄, filtered and concentrated in vacuo. The residue was purified by chromatography (PE:EA=10:1 to 2:1) to give 54c (100 mg, 26%) as a colorless oil. LC-MS (Agilent, P-2): $R_t$ 2.943 min; m/z calculated for $C_{29}H_{36}N_2O_3$ [M+H]⁺ 461.3. found [M+H]⁺ 461.3.

4. Procedure for the Preparation of 54

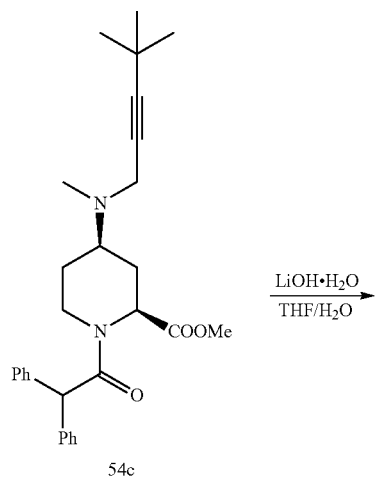

Example 24: Compound 55 (2'S,3R,4'R)-1'-(2,2-diphenylacetyl)-3-phenyl-[1,4'-bipiperidine]-2'-carboxylic acid

1. Procedure for the Preparation of 55b

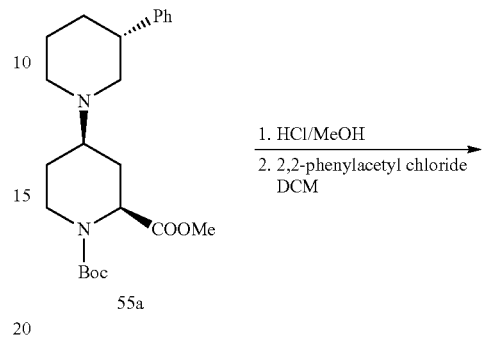

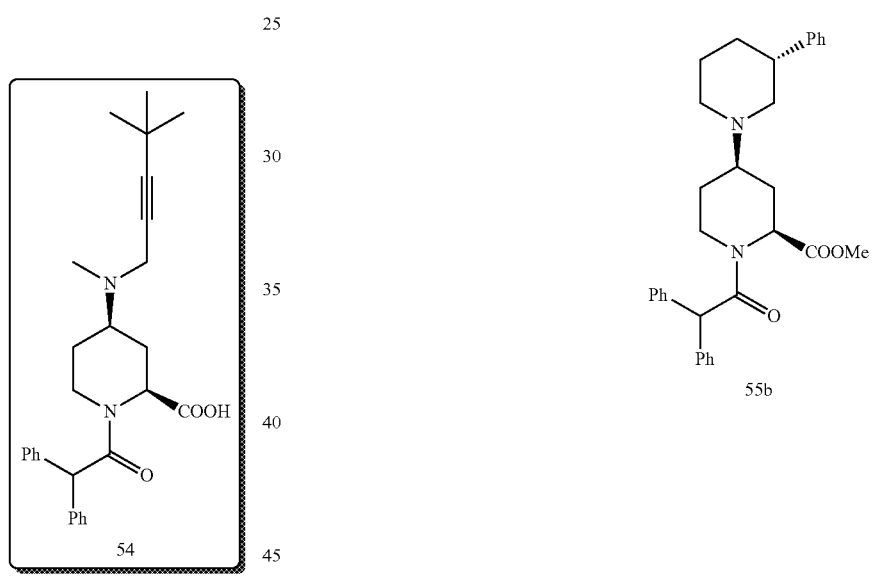

A mixture of 54c (100 mg, 0.22 mmol) and LiOH·H$_2$O (37 mg, 0.87 mmol) in THF/H$_2$O (3 mL/0.5 mL) was stirred at RT overnight, TLC (PE:EA=2:1) showed that the starting material was consumed. The mixture was concentrated in vacuo, the residue was dissolved in water (3 mL) and acidified to pH 3~4 with a 3 M aqueous HCl solution. The resulting precipitate was collected by filtration, re-crystallized from ether/hexane then purified by preparative HPLC to give 54 (40 mg, 41%) as a white solid. LC-MS (Agilent, P-2): R$_t$ 2.92 min; m/z calculated for C$_{28}$H$_{34}$N$_2$O$_3$ [M+H]$^+$ 447.3. found [M+H]$^+$ 447.3. HPLC (JULY-L) (214 and 254 nm): R$_t$ 9.06 min.

A mixture of 55a (350 mg, 0.87 mmol) in 4 M HCl/MeOH (5 mL) was stirred at RT overnight, TLC (PE:EA=2:1) showed that the starting material was consumed. The mixture was concentrated in vacuo, the residue was dissolved in water, basified to pH 9-10 with K$_2$CO$_3$ and extracted with DCM (30 mL×3). The combined organic extracts were dried over Na$_2$SO$_4$, filtered and concentrated in vacuo. The residue was dissolved in DCM (10 mL), triethylamine (0.13 g, 1.31 mmol) and 2,2-diphenylacetyl chloride (0.24 g, 1.04 mmol) were added and the mixture was stirred at RT for 10 min, TLC (DCM:MeOH=10:1) showed that the starting material was consumed. The reaction was quenched with water, the DCM layer was separated, washed with brine, dried over Na$_2$SO$_4$, filtered and concentrated in vacuo. The residue was purified by chromatography (PE:EA=5:1 to 1:2) to give 55b (250 mg, 57%) as a brown oil. LC-MS (Agilent, P-2): R$_t$ 2.84 min; m/z calculated for C$_{32}$H$_{36}$N$_2$O$_3$ [M+H]$^+$ 497.3. found [M+H]$^+$ 497.3.

2. Procedure for the Preparation of 55

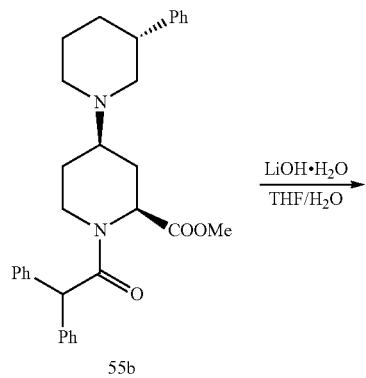

55b

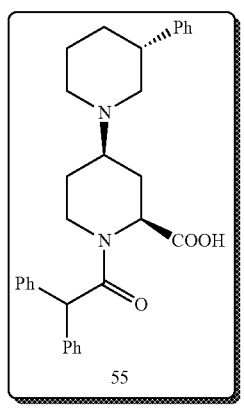

55

A mixture of 55b (250 mg, 0.5 mmol) and LiOH.H₂O (84 mg, 2.0 mmol) in THF/H₂O (5 mL/0.5 mL) was stirred at RT overnight, TLC (DCM:MeOH=20:1) showed that the starting material was consumed. The mixture was concentrated in vacuo, the residue was dissolved in water and acidified to pH 3~4 with a 3 M aqueous HCl solution. The resulting precipitate was collected by filtration and re-crystallized from EA/ether to give 55 (105 mg, 43%) as a white solid. LC-MS (Agilent, P-2): $R_t$ 2.82 min; m/z calculated for $C_{31}H_{34}N_2O_3$ $[M+H]^+$ 483.3. found $[M+H]^+$ 483.3. HPLC (JULY-L) (214 and 254 nm): $R_t$ 8.59 min.

Example 25: Compound 56 (2'S,3R,4'R)-1-(2,2-diphenylacetyl)-3-phenyl-[1,4'-bipiperidine]-2'-carboxylic acid 1. Procedure for the Preparation of 56a

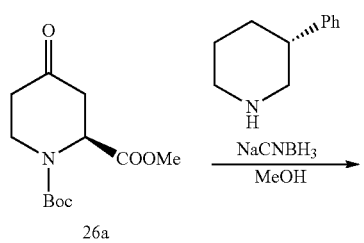

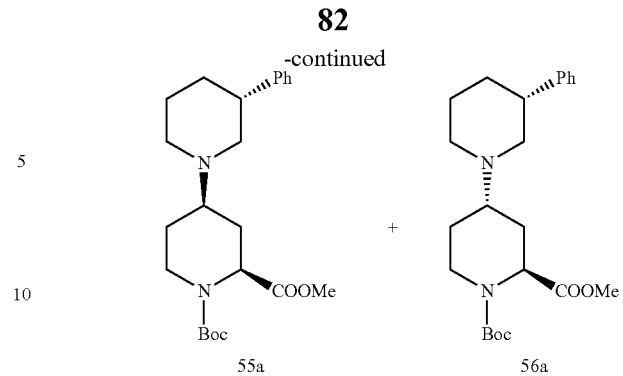

55a + 56a

To a solution of 26a (500 mg, 1.94 mmol) and (R)-3-phenyl-piperidine (376 mg, 2.33 mmol) in MeOH (10 mL) at 0° C. under N₂ was added 2 drops of AcOH and the mixture was stirred at 0° C. for 30 min. NaCNBH₃ (158 mg, 2.52 mmol) was added and the mixture was allowed to warm slowly to RT and stirred overnight, TLC (PE:EA=2:1) showed that the starting material was consumed. The solvent was removed in vacuo, the residue was diluted with water (30 mL) and the mixture was extracted with DCM (20 mL×3). The combined organic extracts were washed with brine, dried over Na₂SO₄, filtered and concentrated in vacuo. The residue was purified by chromatography (PE:EA=1:0 to 1:1) to give 55a (340 mg, 43%) as the first eluting product followed by 56a (113 mg, 14%), each obtained as colorless oils. LC-MS (Agilent, P-2) for 55a: $R_t$ 2.742 min; m/z calculated for $C_{23}H_{34}N_2O_4$ $[M+H]^+$ 403.3, $[M+Na]^+$ 425.3. found $[M+H]^+$ 403.3, $[M+Na]^+$ 425.3. LC-MS (Agilent, P-2) for 56a: $R_t$ 2.749 min; m/z calculated for $C_{23}H_{34}N_2O_4$ $[M+H]^+$ 403.3, $[M+Na]^+$ 425.3. found $[M+H]^+$ 403.3, $[M+Na]^+$ 425.3.

2. Procedure for the Preparation of 56b

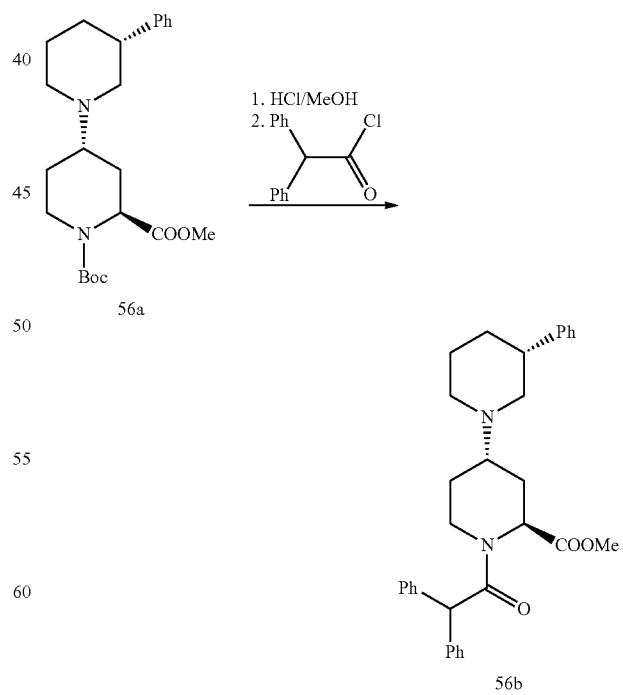

A mixture of 56a (113 mg, 0.28 mmol) in 4 M HCl/MeOH (10 mL) was stirred at RT overnight, TLC (PE:EA=1:1)

showed that the starting material was consumed. The mixture was concentrated in vacuo, the residue was dissolved in water (30 mL), basified to pH 10 with K$_2$CO$_3$ and extracted with DCM (20 mL×2) followed by chloroform/isopropanol (3/1, v/v, 15 mL). The combined organic extracts were dried over Na$_2$SO$_4$, filtered and concentrated in vacuo and the residue was dissolved in DCM (20 mL). Et$_3$N (42 mg, 0.42 mmol) was added to the obtained DCM solution followed by diphenyl acetyl chloride (71 mg, 0.31 mmol) and the mixture was stirred at RT for 30 min, TLC (DCM:MeOH=10:1) showed that the starting material was consumed. The mixture was washed with brine, dried over Na$_2$SO$_4$, filtered and concentrated in vacuo. The residue was purified by chromatography (PE:EA=1:0 to 1:2) to give 56b (70 mg, 50%) as a white solid. LC-MS (Agilent, P-2): R$_t$ 2.79 min; m/z calculated for C$_{32}$H$_{36}$N$_2$O$_3$ [M+H]$^+$ 497.3. found [M+H]$^+$ 497.3.

3. Procedure for the Preparation of 56

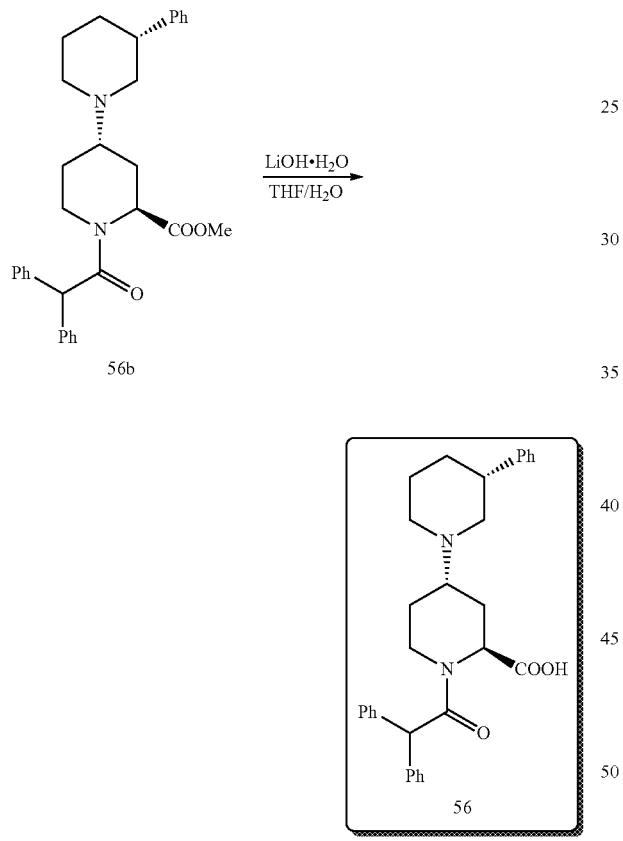

Example 26: Compound 59 (2S,4R)-1-(2,2-diphenylacetyl)-4-(methyl(3-phenylprop-2-yn-1-yl)amino)piperidine-2-carboxamide

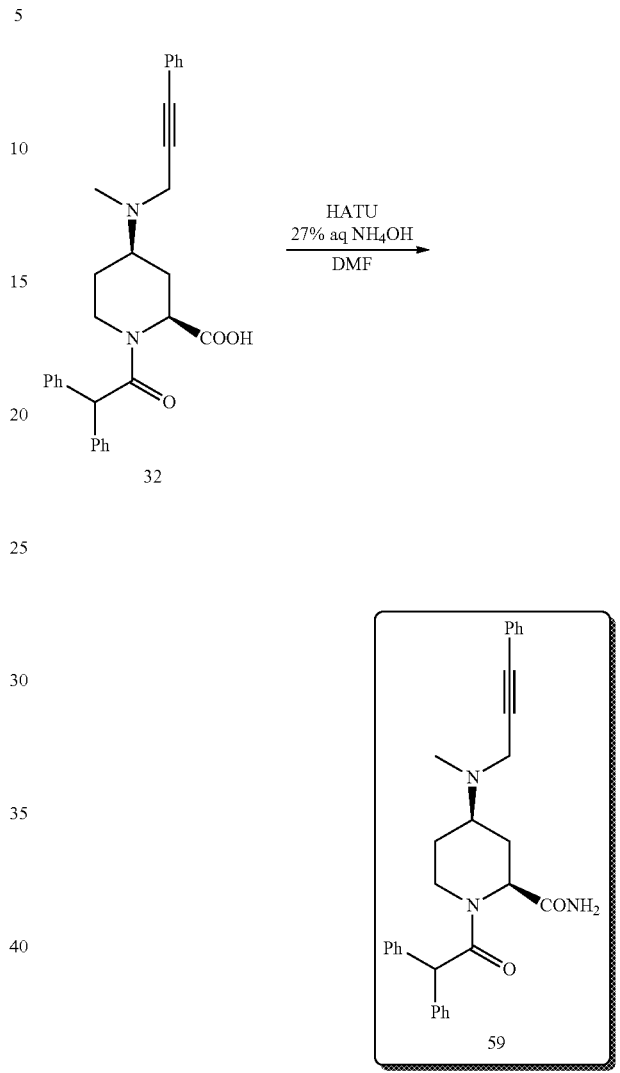

A mixture of 56b (70 mg, 0.14 mmol) and LiOH.H$_2$O (23 mg, 0.56 mmol) in THF/H$_2$O (3 mL/1 mL) was stirred at RT overnight, TLC (DCM:MeOH=10:1) showed that the starting material was consumed. The mixture was concentrated in vacuo, the residue was dissolved in water (15 mL), acidified to pH~3 with a 3 M aqueous HCl solution and extracted with DCM. The combined organic extracts were washed with brine, dried over Na$_2$SO$_4$, filtered and concentrated in vacuo. The residue was purified by preparative HPLC to give 56 (40 mg, 59%) as a white solid. LC-MS (Agilent, P-2): R$_t$ 2.85 min; m/z calculated for C$_{31}$H$_{34}$H$_2$O$_3$ [M+H]$^+$ 483.3. found [M+H]$^+$ 483.3. HPLC (JULY-L) (214 and 254 nm): R$_t$ 8.68 min.

To a solution of 32 (550 mg, 1.17 mmol) in DMF (10 mL) was added Et$_3$N (141 mg, 1.40 mmol) and HATU (530 mg, 1.40 mmol) and the mixture was stirred at RT for 30 min. A 27% aqueous NH$_4$OH solution (110 mg, 1.75 mmol) was then added and stirring was continued at RT overnight, TLC (DCM:MeOH=10:1) showed that the starting material was consumed. The mixture was poured into ice-water (80 mL), extracted with EA (30 mL×3) and the combined organic extracts were washed with brine, dried over Na$_2$SO$_4$, filtered and concentrated in vacuo to give crude 59 (530 mg) as a yellow oil. A portion (150 mg) of this crude product was purified twice by chromatography (DCM:MeOH=1:0 to 50:1) to give pure 59 (50 mg, 33%) as a white solid. LC-MS (Agilent, P-2): R$_t$ 2.84 min; m/z calculated for C$_{30}$H$_{31}$N$_3$O$_2$ [M+H]$^+$ 466.2. found [M+H]$^+$ 466.3. HPLC (JULY-L) (214 and 254 nm): R$_t$ 8.87 min.

Example 27: Compound 60 (2S,4R)-1-(2,2-diphenylacetyl)-4-(methyl(3-phenylprop-2-yn-1-yl)amino)piperidine-2-carbonitrile

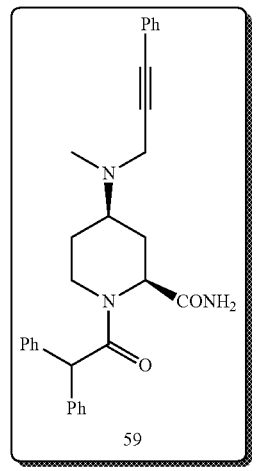

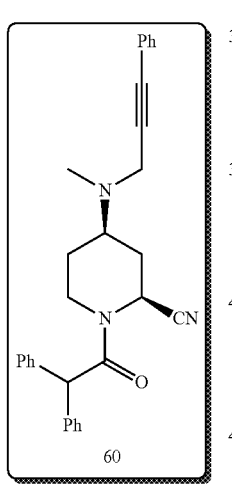

To a solution of crude 59 (350 mg, 0.75 mmol) in DCM (10 mL) at 0~5° C. under a $N_2$ atmosphere was added $Et_3N$ (114 mg, 1.13 mmol) then triflic anhydride (296 mg, 1.05 mmol) and the mixture was allowed to warm slowly to RT and stirred overnight, TLC (DCM:MeOH=20:1) showed that the starting material was consumed. The reaction was quenched with brine (10 mL) and the organic layer was separated, dried over $Na_2SO_4$, filtered and concentrated in vacuo. The residue was purified by chromatography (PE:EA=1:0 to 2:1) to give 60 (140 mg, 41% over two steps) as a white solid. LC-MS (Agilent, P-2): $R_t$ 2.57 min; m/z calculated for $C_{30}H_{29}N_3O$ [M+H]$^+$ 448.2. found [M+H]$^+$ 448.2. HPLC (JULY-L) (214 and 254 nm): $R_t$ 9.05 min.

Example 28: Compound 61 (2S,4R)-4-(methyl(3-phenylprop-2-yn-1-yl)amino)-2-(1H-tetrazol-5-yl)piperidin-1-yl)-2,2-diphenylethanone

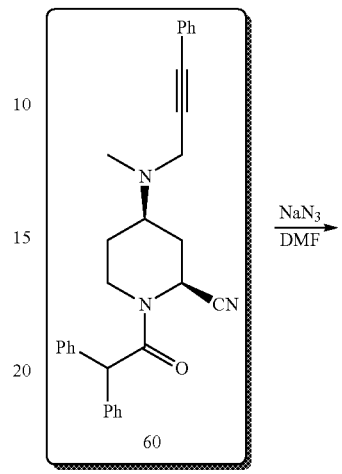

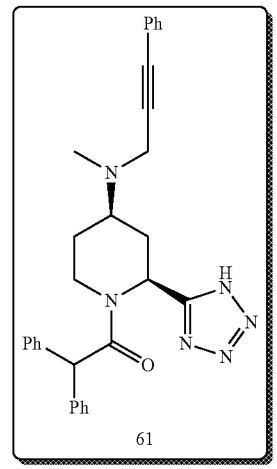

To a solution of 60 (78 mg, 0.17 mmol) in DMF (1 mL) was added $NaN_3$ (56.6 mg, 0.87 mmol) and $NH_4Cl$ (62.5 mg, 1.17 mmol). The reaction vessel was sealed and the mixture was heated at 100° C. overnight, TLC (DCM:MeOH=50:1) showed that the starting material was consumed. The mixture was cooled to RT, dissolved in water (15 mL) and adjusted to pH 4-5 with a 3 M aqueous HCl solution, then extracted with EA (10 mL×3). The combined organic extracts were washed with brine (10 mL), dried over $Na_2SO_4$, filtered and concentrated in vacuo. The residue was purified by chromatography (DCM:MeOH=100:1 to 10:1) followed by preparative HPLC to give 61 (36 mg, 43%) as a white solid. LC-MS (Agilent, P-2): $R_t$ 2.951 min; m/z calculated for $C_{30}H_{30}N_6O$ [M+H]$^+$ 491.3. found [M+H]$^+$ 491.3. HPLC (JULY-L) (214 and 254 nm): $R_t$ 8.947 min.

Example 29: Compound 62 (2S,4R)—N—(N,N-dimethylsulfamoyl)-1-(2,2-diphenylacetyl)-4-(3-phenylprop-2-yn-1-yl)amino)piperidine-2-carboxamide

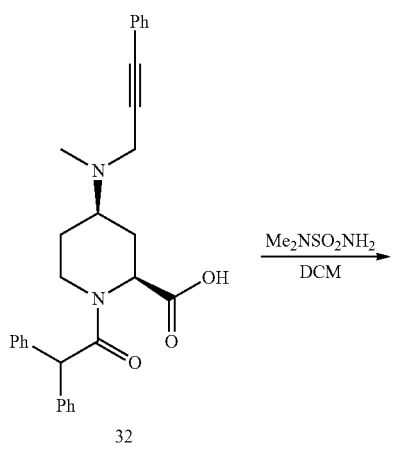

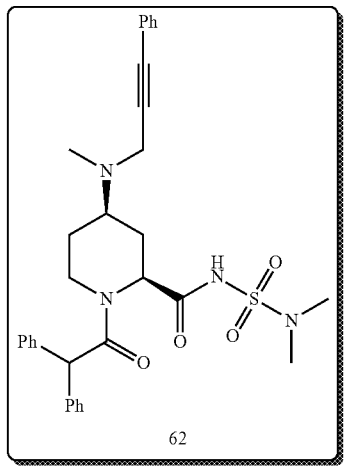

A mixture of 32 (50 mg, 0.107 mmol), N,N-dimethylsulfamide (16 mg, 0.128 mmol), DMAP (4 mg, 0.032 mmol) and DCC (26 mg, 0.128 mmol) in DCM (1 mL) was stirred at RT overnight, TLC (DCM:MeOH=20:1) showed that the starting material was consumed. The mixture was diluted with DCM (20 mL), washed with brine, dried over $Na_2SO_4$, filtered and concentrated in vacuo. The residue was purified by chromatography (DCM:MeOH=1:0 to 50:1) to give 62 (36 mg, 59%) as a white solid. LC-MS (Agilent, P-2): $R_t$ 2.66 min; m/z calculated for $C_{32}H_{33}N_4O_4S$ $[M+H]^+$ 573.2. found $[M+H]^+$ 573.3. HPLC (JULY-L) (214 and 254 nm): $R_t$ 9.12 min.

Biological Example 1: $AT_2$ Receptor Binding

Media and Solutions
1. Trypsin-EDTA (for preparation of 100 mL)
   Trypsin 0.25 g
   2% EDTA 2 mL
   PBS 98 mL
   Dissolve trypsin in 2% EDTA and PBS completely; sterilize the solution by passing through a 0.20 μM membrane filter; store at 4° C.
2. DMEM medium (for preparation of 1 L)
   The powder was dissolved into 950 mL of distilled water with gentle stirring until the solution becomes clear.
   Add $NaHCO_3$ 1.176 g for DMEM medium.
   Adjust pH of medium to 0.2-0.3 below final working pH using 1 M NaOH or 1 M HCl. Add slowly with stirring.
   Dilute to 1 liter with $ddH_2O$.
   Sterilize the medium immediately by filtration.
   Store at 4° C.
3. TE buffer
   20 mM Tris-HCl, pH 7.4,
   5 mM EDTA
4. Binding Assay Buffer
   50 mM Hepes, pH 7.4
   5 mM $MgCl_2$
   1 mM $CaCl_2$
   0.2% BSA
5. Wash Buffer
   50 mM Hepes, pH 7.4

Procedures for HEK293/$AT_2$ Receptor Transient Cell Transfection
   Cells were plated into 150 mm dish at 50% density for transient transfection. Cells were ready for transfection after overnight incubation (the confluence reaches around 80%).
   75 μL Lipofectamine™2000 diluted in 6.25 mL OptiMEM I Reduced Serum Medium, was mixed gently, and incubated at room temperature for 5 minutes.
   50 μg expression plasmid DNA diluted in 6.25 mL OptiMEM I Reduced Serum Medium without serum was mixed gently.
   After the 5 minute incubation, the diluted DNA was combined with the diluted Lipofectamine™2000 (total volume is 12.5 mL). The mixture was mixed gently and incubated for 30 minutes at room temperature to allow the DNA-Lipofectamine™2000 complexes to form.
   The 12.5 mL DNA-Lipofectamine™2000 complexes were added into the 150 mm dish and mixed gently by rocking the dish back and forth.
   The cells were incubated at 37° C. with 5% $CO_2$ for 48 hours.
   Cells were collected and stored frozen at –80° C.

Procedures for HEK293/$AT_2$ Receptor Cell Membrane Preparation
   Frozen HEK293/$AT_2$ receptor (transient transfected) cells were homogenized in ice cold TE buffer for 10 s.
   The homogenate was centrifuged at 25,000 g for 30 minutes.
   The pellet was resuspended in ice cold tissue buffer.
   Protein concentrations were determined using Bradford assay method with BSA as standard.
   The membrane protein was frozen under –80° C.

Compound Preparation
   Solutions of all compounds were prepared by microplate liquid handling equipment such as Janus or Precision 2000. Compounds, dissolved in DMSO were stored in a Freezer. Compounds were prepared from 30 mM in 100% DMSO.

Step 1: Dose Plate Preparation (96 Well Plate)
   Add the 3 μL [30 mM] compound stock to column 1 on the plate.
   Add 15 μL of 100% DMSO to column 1.
   Add 10.81 μL of 100% DMSO to column 2-12.
   Transfer 5 μL from column 1 into column 2 (half log dilution).
   Transfer 5 μL from column 2 into column 3 (half log dilution).

Transfer 5 μL from column 3 into column 4 (half log dilution).
Transfer 5 μL from column 4 into column 5 (half log dilution).
Transfer 5 μL from column 5 into column 6 (half log dilution).
Transfer 5 μL from column 6 into column 7 (half log dilution).
Transfer 5 μL from column 7 into column 8 (half log dilution).
Transfer 5 μL from column 8 into column 9 (half log dilution).
Transfer 5 μL from column 9 into column 10 (half log dilution)
Transfer 5 μL from column 10 into column 11 (half log dilution)
Transfer 5 μL from column 11 into column 12 (half log dilution).

All the compounds were diluted using Precision 2000 microplate liquid handling equipment. The top concentration of compound was 5 mM with 100% DMSO.

Step 2: Working Plate Preparation (96 Well Plate)
Compounds were diluted 50-fold with buffer.
49 μL buffer was added to the well of 96 well plate.
1 μL compound solution from dose plate was transferred to the corresponding well of working plate.
The top concentration of compound was 100 μM with 2% DMSO.

Step 3: Assay Plate Preparation (96 Well Plate)
15 μL of compound solution was transferred from each well of working plate to the well of assay plate by Janus. Each compound was assayed in duplicate in each plate and there were 4 compounds per plate.

Procedures for $AT_2$ Receptor Binding Assay
120 μL membrane (5 mg protein/well) was incubated with 15 μL of [$^{125}$I]-CGP42112A and 15 μL of compound at RT for 1.5 hrs.
The binding reaction was stopped by rapid filtration through Unifilter GF/C plates (presoaked in 0.3% (v:v) BSA).
Plate was washed three times with ice cold wash buffer.
The filtration plates were dried at 37° C. overnight.
50 μL of scintillation cocktail was added to each well.
Radioactivity was determined using MicroBetaTriluxmicroplate scintillation counter.

Data Analysis
Data was analyzed through 4 parameter logic using Prism 5.0 software.
The results are shown in the following Table:

| Compound | IC$_{50}$ (nM) |
| --- | --- |
| 1 | 209.8 |
| 9 | 159.1 |
| 26 | 217.6 |
| 30 | 76.65 |
| 31 | 5091 |
| 32 | 108.2 |
| 33 | 2710 |
| 34 | 917.8 |
| 35 | 100.9 |
| 38 | 854.1 |
| 39 | 648.2 |
| 40 | 227.5 |
| 41 | 100.7 |
| 42 | 852.3 |
| 43 | 2051 |
| 44 | 153.4 |
| 45 | 354.3 |
| 46 | 55.88 |
| 47 | 1038 |
| 52 | 228.5 |
| 54 | 33.86 |
| 55 | 294.3 |
| 56 | 110.6 |
| 57 | 1444 |
| 58 | 169.5 |

Biological Example 2: $AT_1$ Receptor Binding

Evaluation of the affinity of the test compounds for the human angiotensin-II $AT_1$ receptor in transfected HEK-293 cells was determined in a radioligand assay (Le, et al., Eur. J. Pharmacol., 2005, 513:35).

Cell membrane homogenates (8 μg protein) were incubated for 120 min at 37° C. with 0.005 nM [$^{125}$I][Sar1-Ile8] angiotensin-II in the absence or presence of the test compound in a buffer containing 50 mM Tris-HCl (pH 7.4), 5 mM MgCl$_2$, 1 mM EDTA and 0.1% BSA. Nonspecific binding was determined in the presence of 10 mM angiotensin-II.

Following incubation, the samples were filtered rapidly under vacuum through glass fibre filters (GF/B, Packard) presoaked with 0.3% PEI and rinsed several times with ice-cold 50 mM Tris-HCl using a 96-sample cell harvester (Unifilter, Packard). The filters were dried then counted for radioactivity in a scintillation counter (Topcount, Packard) using a scintillation cocktail (Microscint 0, Packard). The results were expressed as a percent inhibition of the control radioligand specific binding.

The standard reference compound was saralasin, which was tested in each experiment at several concentrations to obtain a competition curve from which its IC$_{50}$ was calculated.

The assay was performed in a volume of 200 μL in a 96 well plate. Test compounds used were compounds 26, 30, 32 and 33.

Neither compound had sufficient binding activity for the $AT_1$ receptor to allow an IC$_{50}$ to be determined. The maximum concentration of test compound used was 10 μM.

REFERENCES

Chakrabarty et al., 2008, Estrogen elicits dorsal root ganglion axon sprouting via a rennin-angiotensin system. Endocrinology, 149(7):3452-3460.
Clere et al., 2010, Deficiency or blockade of angiotensin II type 2 receptor delays tumorigenesis by inhibiting malignant cell proliferation and angiogenesis. Int. J. Cancer, 127: 2279-2291.
Izu et al., 2009, Angiotensin II Type 2 receptor blockade increases bone mass. J. Biol. Chem., 284(8):4857-4864.
Steckelings et al., 2005, The $AT_2$ receptor—A matter of love and hate. Peptides, 26:1401-1409.
Wallinder et al., 2008, Selective angiotensin II $AT_2$ receptor agonists: Benzamide structure-activity relationships. Bioorganic & Medicinal Chemistry, 16:6841-6849.
Wan et al., 2004, Design, Synthesis and biological evaluation of the first selective nonpeptide $AT_2$ receptor agonist. J. Med. Chem., 47:5995-6008.

Wexler et al., 1996, Nonpeptide angiotensin II receptor antagonists: The next generation in antihypertensive therapy. *J. Med. Chem.*, 39(3):325-656.

The invention claimed is:

1. A compound of formula (I):

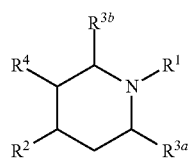

wherein R¹ is —C(=O)CH(aryl)(aryl), —C(=O)CH(aryl)(cycloalkyl), —C(=O)CH(cycloalkyl)(cycloalkyl), —C(=O)N(aryl)(aryl), —C(=O)N(aryl)(cycloalkyl) or —C(=O)N(cycloalkyl)(cycloalkyl);

R² is —CH₂phenyl, —CH₂CH₂phenyl, —CH₂CH₂CH₂phenyl, —OCH₂phenyl, —OCH₂CH₂phenyl, —OCH₂CH₂CH₂phenyl, —CH₂CH=CHphenyl, —OCH₂CH=CHphenyl, —OCH₂C≡Cphenyl, —CH₂C≡Cphenyl, —CH₂OCH₂phenyl, —CH₂Ophenyl, —N(CH₃)(2-phenypropyl), —N(CH₃)(3-phenylpropyn-1-yl), —N(CH₃)(phenethyl), -3-benzylmorpholine, —N(CH₃)(benzyl), —N(CH₃)(CH₂C≡CCH₃), —N(CH₃)(CH₂C≡CCH(CH₃)₂, —N(CH₃)(CH₂C≡C-4-fluorophenyl), —N(CH₃)(CH₂-4-phenyl-5-tetrazolyl), —N(CH₃)(CH₂-2-phenyl-1-cyclopent-1-enyl), —OCH₂C≡C-4-fluorophenyl, —N(CH₃)(CH₂C≡CCF₃), —N(CH₃)(CH₂C≡C—C(CH₃)₃, -3-phenylpiperidine, —N(CH₃)(CH₂C≡Cphenyl); 2-(5-phenyl)oxazolyl or 2-(5-benzyl)oxazolyl)

R³ᵇ is hydrogen and R³ᵃ is —CO₂H, —CH₂CO₂H, —C(=O)C(=O)OH, —C(=O)NH₂, —CN, tetrazolyl —C(=O)NHSO₂N(C₁₋₆alkyl)₂, —C(=O)NHSO₂C₁₋₆alkyl, —C(=O)NHSO₂phenyl, —C(=O)NHSO₂CF₃—SO₃H or —PO₃H₂;

R⁴ is hydrogen;

or a pharmaceutically acceptable salt thereof.

2. A compound according to claim 1 wherein R² is —OCH₂phenyl, —OCH₂CH₂CH₂phenyl, —OCH₂C≡Cphenyl, —N(CH₃)(3-phenylpropyn-1-yl), —N(CH₃)(phenethyl), —N(CH₃)(benzyl), —N(CH₃)(CH₂C≡CCH₃), —N(CH₃)(CH₂C≡CCH(CH₃)₂, —N(CH₃)(CH₂C≡C-4-fluorophenyl), —OCH₂C≡C-4-fluorophenyl, —N(CH₃)(CH₂C≡C—C(CH₃)₃, or -3-phenylpiperidine; or a pharmaceutically acceptable salt thereof.

3. A compound according to claim 1 wherein R³ᵃ is —CO₂H; or a pharmaceutically acceptable salt thereof.

4. A pharmaceutical composition comprising a compound of formula (I) according to claim 1 or a pharmaceutically acceptable salt thereof and a pharmaceutically acceptable carrier.

5. The compound according to claim 1, or a pharmaceutically acceptable salt thereof, wherein R¹ is —C(=O)CH(phenyl)(phenyl).

6. The compound according to claim 1, or a pharmaceutically acceptable salt thereof, wherein the said compound is selected from:

(2S)-4-(benzyloxy)-1-(2,2-diphenylacetyl)piperidine-2-carboxylic acid;

(2S,4S)-4-benzyloxy-1-(2,2-diphenylacetyl)piperidine-2-carboxylic acid;

(2S,4R)-1-(2,2-diphenylacetyl)-4-(methyl(phenylpropyl)amino)piperidine-2-carboxylic acid;

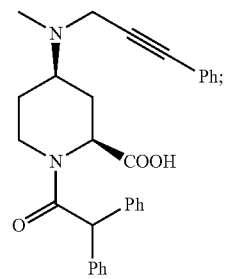 [SMILES: CN(CC#Cc1ccccc1)[C@@H]1CCN(C(=O)C(c2ccccc2)c2ccccc2)[C@H](C(=O)O)C1]

(2S,4S)-1-(2,2-diphenylacetyl)-4-(methyl(3-phenylprop-2-yn-1yl)amino)piperidine-2-carboxylic acid;

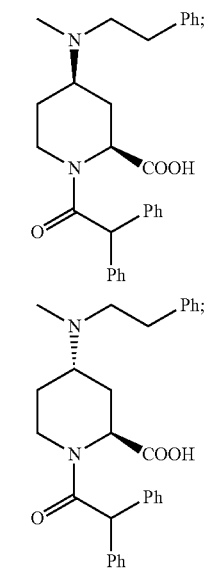

(2S,4R)-4-(benzyl(methyl)amino)-1-(2,2-diphenylacetyl)piperidine-2-carboxylic acid;

(2S,4S)-4-(benzyl(methyl)amino)-1-(2,2-diphenylacetyl)piperidine-2-carboxylic acid;

(2S,4R)-1-(2,2-diphenylacetyl)-4-((3-phenylprop-2-yn-yl)oxy)piperidine-2-carboxylic acid;

(2S,4R)-1-(2,2-diphenylacetyl)-4-((3-phenylpropyl)oxy)piperidine-2-carboxylic acid;

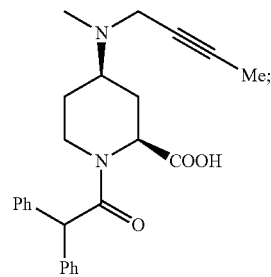

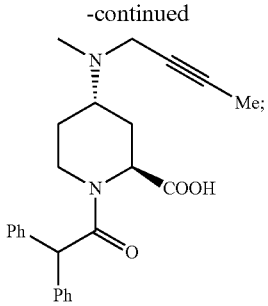

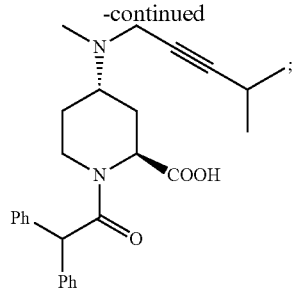

(2S,4R)-1-(2,2-diphenylacetyl)-4-((3-(4-fluorophenyl)prop-2-yn-1-yl)(methyl)amino)piperidine-2-carboxylic acid;
(2S,4S)-1-(2,2-diphenylacetyl)-4-((3-(4-fluorophenyl)prop-2-yn-1-yl)(methyl)amino)piperidine-2-carboxylic acid;
(2S,4R)-1-(2,2-diphenylacetyl)-4-((3-(4-fluorophenyl)prop-2-yn-1-oxy)piperidine-2-carboxylic acid;
(2S,4R)-4-((4,4-dimethylpent-2-yn-1-yl)(methyl)amino)-1-(2,2-diphenylacetyl)piperidine-2-carboxylic acid;
(2'S,3R,4'R)-1'-(2,2-diphenylacetyl)-3-phenyl-[1,4'-bipiperidine]-2'-carboxylic acid;
(2'S,3S,4'R)-1'-(2,2-diphenylacetyl)-3-phenyl-[1,4'-bipiperidine]-2'-carboxylic acid; and
(2'S,3S,4'S)-1'-(2,2-diphenylacetyl)-3-phenyl-[1,4'-bipiperidine]-2'-carboxylic acid.

\* \* \* \* \*